US009238679B2

(12) United States Patent
Weiner et al.

(10) Patent No.: US 9,238,679 B2
(45) Date of Patent: *Jan. 19, 2016

(54) NUCLEIC ACID MOLECULE ENCODING HEPATITIS B VIRUS CORE PROTEIN AND SURFACE ANTIGEN PROTEIN AND VACCINE COMPRISING THE SAME

(71) Applicant: THE TRUSTEES OF THE UNIVERSITY OF PENNSYLVANIA, Philadelphia, PA (US)

(72) Inventors: David B Weiner, Merion, PA (US); Jian Yan, Havertown, PA (US); Nyamekye Obeng-Adjei, Upper Darby, PA (US)

(73) Assignee: The Trustees of the University of Pennslyvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/622,965

(22) Filed: Sep. 19, 2012

(65) Prior Publication Data
US 2013/0209395 A1 Aug. 15, 2013

Related U.S. Application Data

(63) Continuation-in-part of application No. PCT/US2012/024905, filed on Feb. 13, 2012.

(60) Provisional application No. 61/442,162, filed on Feb. 11, 2011.

(51) Int. Cl.
*A61K 39/29* (2006.01)
*C07K 14/005* (2006.01)
*A61K 39/00* (2006.01)

(52) U.S. Cl.
CPC .......... *C07K 14/005* (2013.01); *A61K 39/29* (2013.01); *A61K 2039/51* (2013.01); *A61K 2039/53* (2013.01); *A61K 2039/555* (2013.01); *A61K 2039/55527* (2013.01); *C07K 2319/02* (2013.01); *C07K 2319/50* (2013.01); *C12N 2730/10122* (2013.01); *C12N 2730/10134* (2013.01); *C12N 2810/60* (2013.01)

(58) Field of Classification Search
CPC ............... A61K 2039/51; A61K 2039/555; A61K 39/29; C12N 2810/60; C12N 2730/10134
USPC ........................................................ 424/229
See application file for complete search history.

(56) References Cited

U.S. PATENT DOCUMENTS

| 4,510,245 | A | 4/1985 | Cousens et al. |
|---|---|---|---|
| 4,554,101 | A | 11/1985 | Hopp et al. |
| 4,722,848 | A | 2/1988 | Paoletti et al. |
| 4,790,987 | A | 12/1988 | Compans et al. |
| 4,797,368 | A | 1/1989 | Carter et al. |
| 4,920,209 | A | 4/1990 | Davis et al. |
| 4,945,050 | A | 7/1990 | Sanford et al. |
| 5,017,487 | A | 5/1991 | Stunnenberg et al. |
| 5,036,006 | A | 7/1991 | Sanford et al. |
| 5,077,044 | A | 12/1991 | Stocker et al. |
| 5,110,587 | A | 5/1992 | Paoletti et al. |
| 5,112,749 | A | 5/1992 | Brey, III et al. |
| 5,174,993 | A | 12/1992 | Paoletti et al. |
| 5,223,424 | A | 6/1993 | Cochran et al. |
| 5,225,336 | A | 7/1993 | Paoletti et al. |
| 5,240,703 | A | 8/1993 | Cochran et al. |
| 5,242,829 | A | 9/1993 | Panicali et al. |
| 5,273,525 | A | 12/1993 | Hofmann et al. |
| 5,294,441 | A | 3/1994 | Curtiss et al. |
| 5,294,548 | A | 3/1994 | McLinden et al. |
| 5,310,668 | A | 5/1994 | Ellis et al. |
| 5,387,744 | A | 2/1995 | Curtiss et al. |
| 5,389,368 | A | 2/1995 | Curtiss et al. |
| 5,424,065 | A | 6/1995 | Curtiss et al. |
| 5,451,499 | A | 9/1995 | Cochran et al. |
| 5,453,364 | A | 9/1995 | Paoletti et al. |
| 5,462,734 | A | 10/1995 | Letchworth et al. |
| 5,470,734 | A | 11/1995 | Sondermeijer et al. |
| 5,474,935 | A | 12/1995 | Chatterjee et al. |
| 5,482,713 | A | 1/1996 | Paoletti et al. |

(Continued)

FOREIGN PATENT DOCUMENTS

| CN | 1832956 A | 9/2006 |
|---|---|---|
| CN | 101502650 | 8/2009 |

(Continued)

OTHER PUBLICATIONS

Frelin et al., "Codon optimization and mRNA amplication effectively enhances the immunogenicity of the hepatitis C virus nonstructural 3/4A gene," Gene Ther., 2004, 11(6):522-33.

Hirao et al., "Instradermal/subcutaneous immunization by electroporation improves plasmid vaccine delivery and potency in pigs and rhesus macaques," Vaccine, 2008, 26(3):440-8.

Luckay et al., "Effect of plasmid DNA vaccine design and in vivo electroporation on the resulting vaccine-specific immune responses in rhesus macaques," J. Virol., 2007, 81(10):5257-69.

Ahlen et al., "In vivo electroporation enhances the immunogenicity of hepatitis C virus nonstructural 3/4A DNA by increased local DNA uptake, protein expression, inflammation, and infiltration of CD3+ T cells," J. Immunol., 2007, 179(7):4741-53.

(Continued)

*Primary Examiner* — Zachariah Lucas
*Assistant Examiner* — Barry A Chestnut
(74) *Attorney, Agent, or Firm* — Riverside Law LLP

(57) ABSTRACT

Provided herein are nucleic acid sequences encoding hepatitis B virus (HBV) core proteins, surface antigen proteins, fragments and combinations thereof as well as genetic constructs/vectors and vaccines that express said protein sequences. These vaccines are able to induce an immune response peripherally and in the liver by recruiting both cellular and humoral agents. Also provided are methods for prophylactically and/or therapeutically immunizing individuals against HBV. The combination vaccine can also be used for particular design vaccines for particular levels of immune responses to HBV challenge.

9 Claims, 56 Drawing Sheets

(56) References Cited

U.S. PATENT DOCUMENTS

| | | | |
|---|---|---|---|
| 5,580,859 | A | 12/1996 | Felgner et al. |
| 5,591,439 | A | 1/1997 | Plotkin et al. |
| 5,593,972 | A | 1/1997 | Weiner et al. |
| 5,643,579 | A | 7/1997 | Hung et al. |
| 5,650,309 | A | 7/1997 | Wong-Staal et al. |
| 5,676,594 | A | 10/1997 | Joosten et al. |
| 5,698,202 | A | 12/1997 | Ertl et al. |
| 5,703,055 | A | 12/1997 | Felgner et al. |
| 5,739,118 | A | 4/1998 | Carrano et al. |
| 5,817,637 | A | 10/1998 | Weiner et al. |
| 5,830,876 | A | 11/1998 | Weiner et al. |
| 5,955,088 | A | 9/1999 | Ghiasi et al. |
| 5,962,428 | A | 10/1999 | Carrano et al. |
| 5,981,505 | A | 11/1999 | Weiner et al. |
| 6,034,298 | A | 3/2000 | Lam et al. |
| 6,042,836 | A | 3/2000 | Berman et al. |
| 6,110,161 | A | 8/2000 | Mathiesen et al. |
| 6,156,319 | A | 12/2000 | Cohen et al. |
| 6,261,281 | B1 | 7/2001 | Mathiesen et al. |
| 6,589,529 | B1 | 7/2003 | Choi et al. |
| 6,697,669 | B2 | 2/2004 | Dev et al. |
| 6,939,862 | B2 | 9/2005 | Bureau et al. |
| 7,238,522 | B2 | 7/2007 | Hebel et al. |
| 7,245,963 | B2 | 7/2007 | Draghia-Akli et al. |
| 7,328,064 | B2 | 2/2008 | Mathiesen et al. |
| 7,964,196 | B2 | 6/2011 | de los Rios et al. |
| 8,298,820 | B2 | 10/2012 | Weiner |
| 2003/0099668 | A1 | 5/2003 | Bachmann et al. |
| 2004/0146529 | A1 | 7/2004 | Selby et al. |
| 2004/0175727 | A1 | 9/2004 | Draghia-Akli et al. |
| 2005/0052630 | A1 | 3/2005 | Smith et al. |
| 2005/0129712 | A1 | 6/2005 | Reimann et al. |
| 2009/0004716 | A1 | 1/2009 | Draghia-Akli et al. |
| 2009/0214593 | A1 | 8/2009 | Sallberg et al. |
| 2010/0291144 | A1 | 11/2010 | Ramanathan et al. |
| 2011/0293726 | A1 | 12/2011 | de los Rios et al. |
| 2012/0034256 | A1 | 2/2012 | Weiner et al. |

FOREIGN PATENT DOCUMENTS

| | | |
|---|---|---|
| WO | 93/24640 | 4/1994 |
| WO | 94/16737 | 8/1994 |
| WO | 98/12332 | 3/1998 |
| WO | 01/85208 | 11/2001 |
| WO | WO2005023293 | * 3/2005 |
| WO | 2004/026899 | 5/2005 |
| WO | 2005/000235 | 6/2005 |
| WO | 2005/116270 | 12/2005 |
| WO | WO2006033679 | * 3/2006 |
| WO | 2008/089144 | 7/2008 |
| WO | 2008/093976 | 8/2008 |
| WO | 2010/016071 | 2/2010 |
| WO | 2009/130588 | 3/2010 |
| WO | 2010/127115 | 11/2010 |

OTHER PUBLICATIONS

Yan et al., "Enhanced cellular immune responses elicited by an engineered HIV-1 subtype B consensus-based envelope DNA vaccine," Mol Ther, 2007, 15(2):411-21.

Rolland et al., "Reconstruction and function of ancestral center-of-tree human immunodeficiency virus type 1 proteins," J. Virol., 2007, 81(16):8507-14.

Kyte et al., "A simple method for displaying the hydropathic character of a protein," J. Mol. Biol., 1982, 157(1):105-32.

Chisari et al., "Rous-Whipple Aware Lecture. Viruses, immunity, and cancer: lessons from hepatitis B," Am J Pathol, 2000, 156(4):1117-32.

Pumpens et al., "HBV core particles as a carrier for B cell/T cell epitopes," Intervirology, 2001, 44(2-3):98-114.

Deny et al., "Hepatitis B virus: from diagnosis to treatment," Pathol Biol (Paris), 2010, 54(4):245-53.

Michel et al., "Hepatitis B vaccines: protective efficacy and therapeutic potential," Pathol Biol (Paris), 2010, 58(4):288-95.

G6VBP1, UniProtKB/TrEMBL entry Q6VBP_1HBV. Retrieved from the internet <URL: http://www.uniprot.org/uniprot/Q6VBP1.txt?version=54>.

JF439753, GenBank Accession No. JF439753, Hepatitis B virus isolate MAU95A2 polymerase (p) gene, complete cds. Retreived from the Internet <URL: http://www.ncbi.nlm.nih.gov/nuccore/JF439753>.

GenBank: ADH82159.1, Hepatitis B virus core protein.

Yin et al., "Hepatitis B virus core protein as an epitope vaccine carrier," Chinese J of Biotech, 2010, pp. 431-438.

Sendi et al., "CTL escape mutations of core protein are more frequent in strains of HBeAg negative patients with low levels of HBV DNA," J Clin Virol., 2009, 46(3):259-264.

* cited by examiner

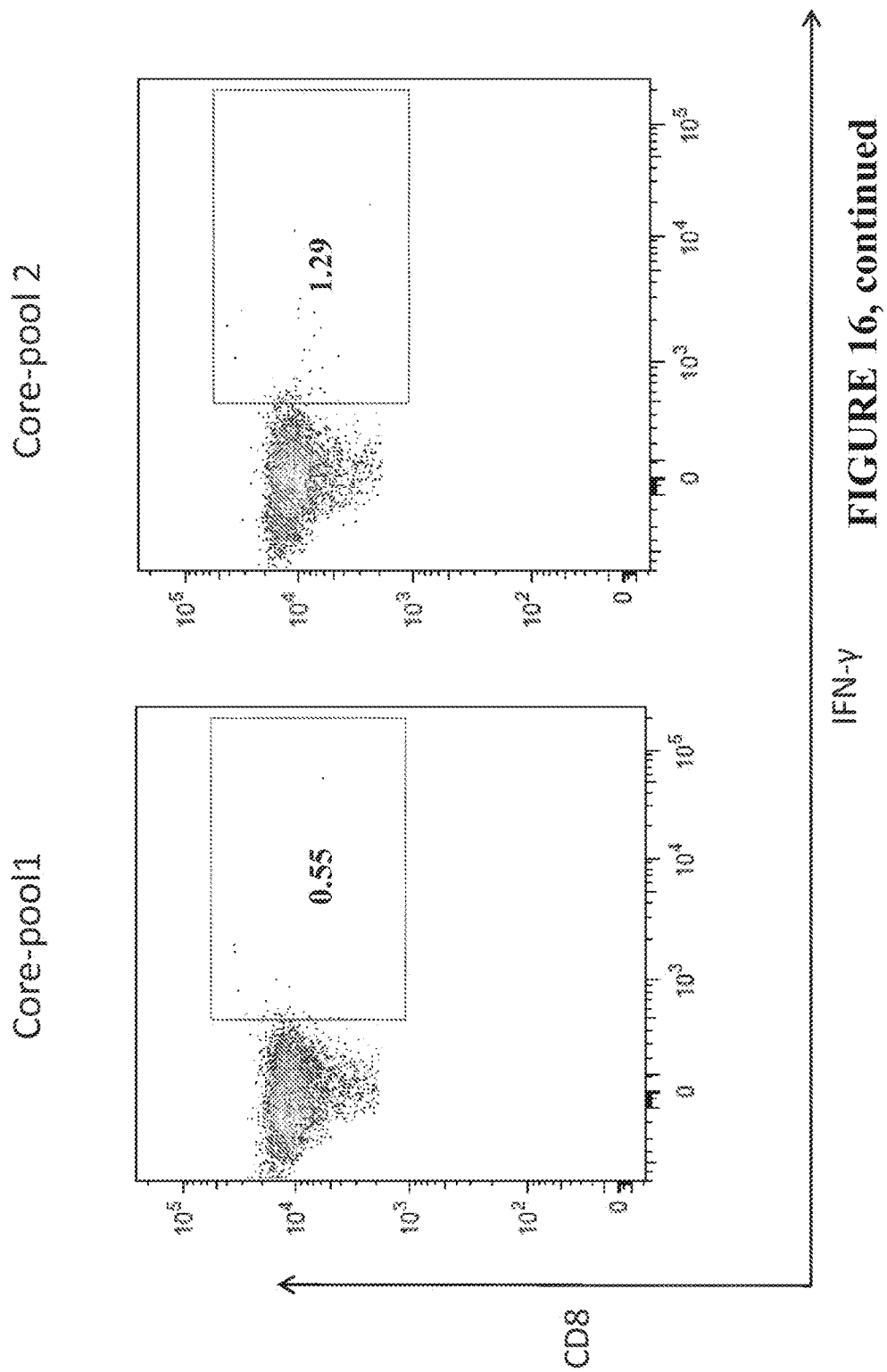
FIGURE 16, continued

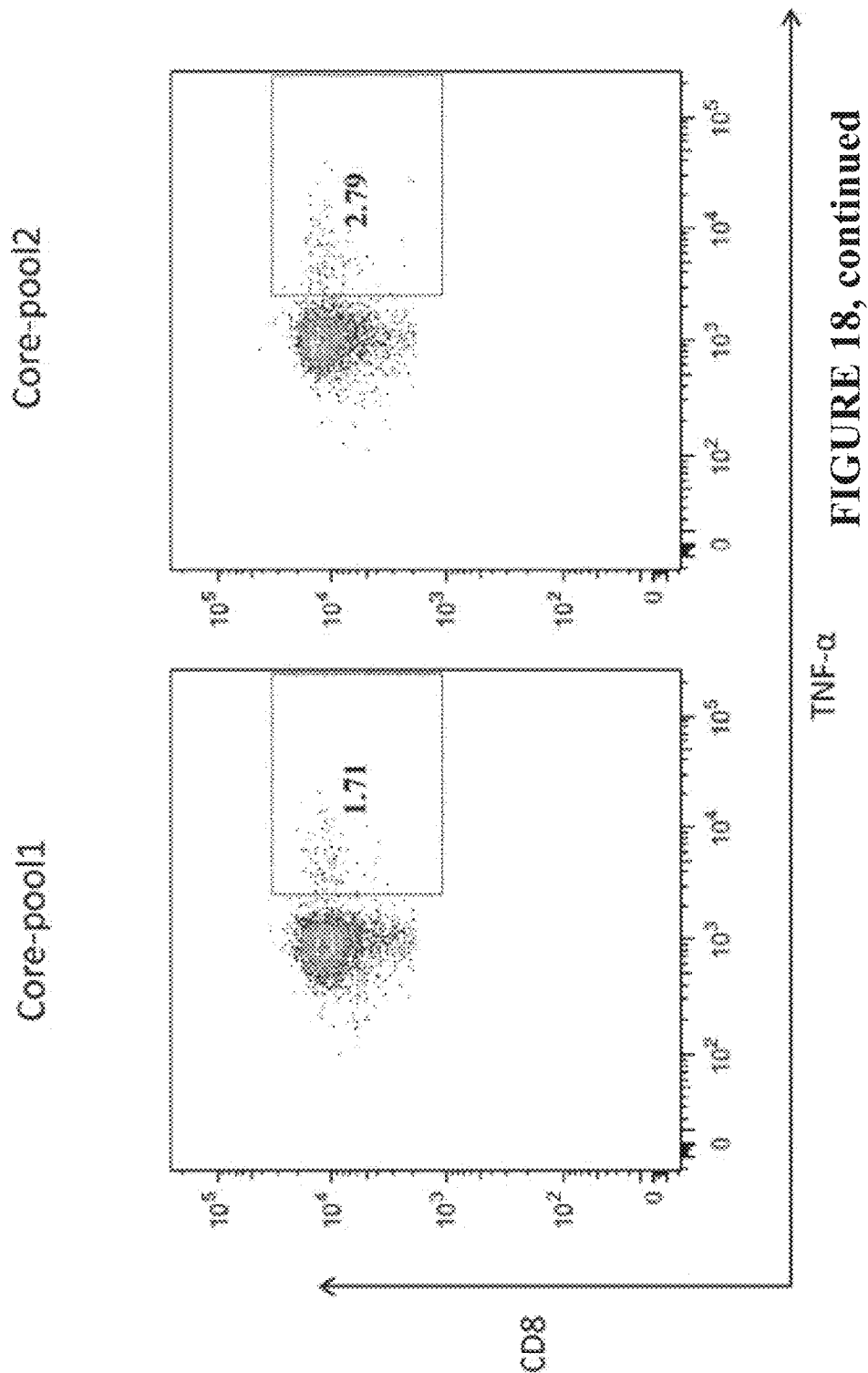
FIGURE 18, continued

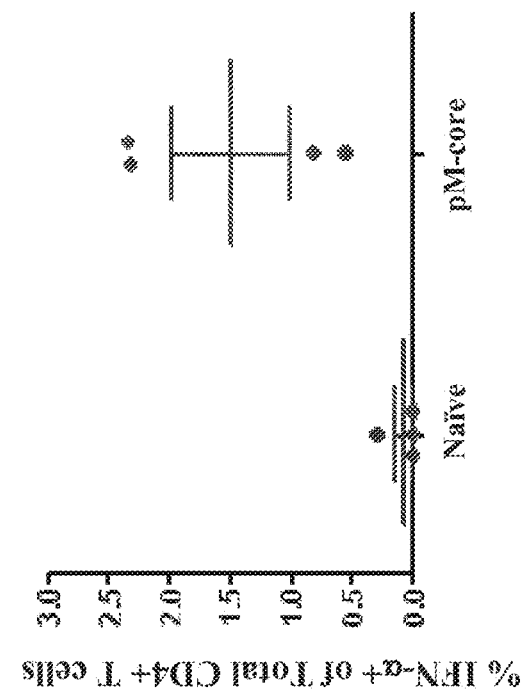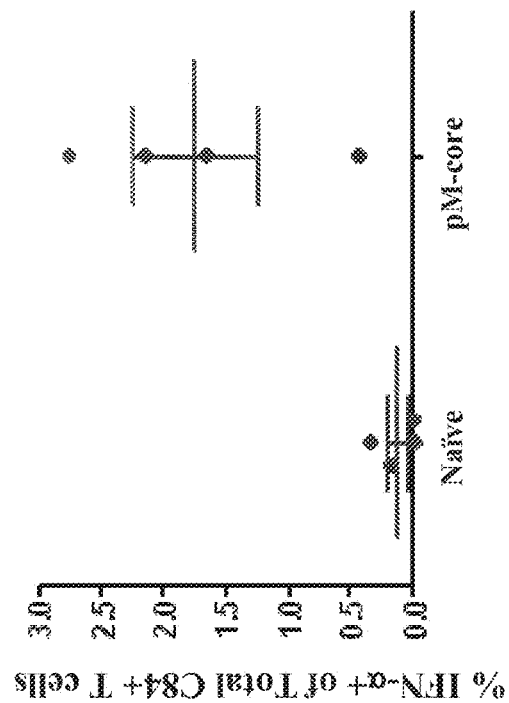
FIGURE 19

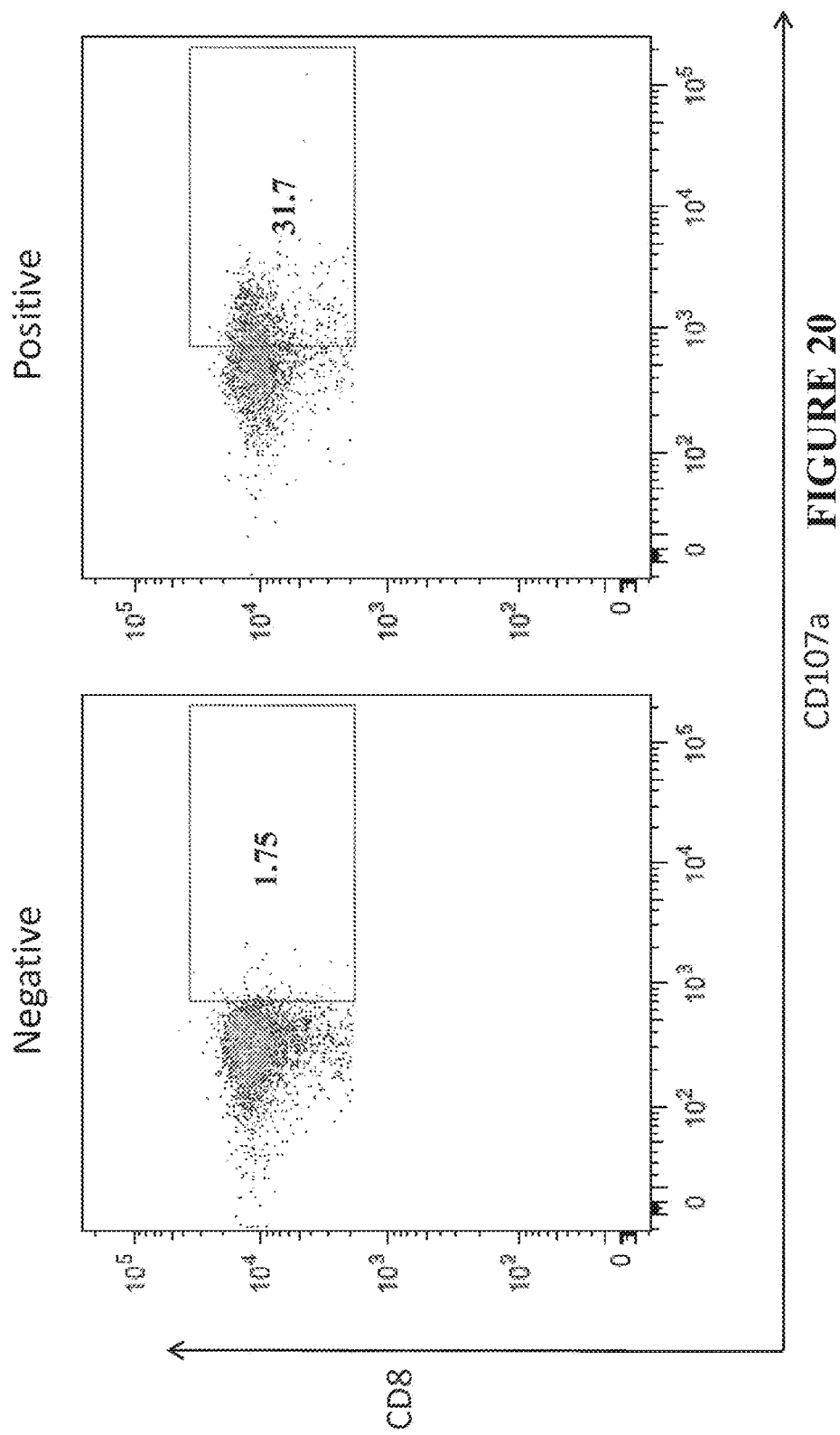

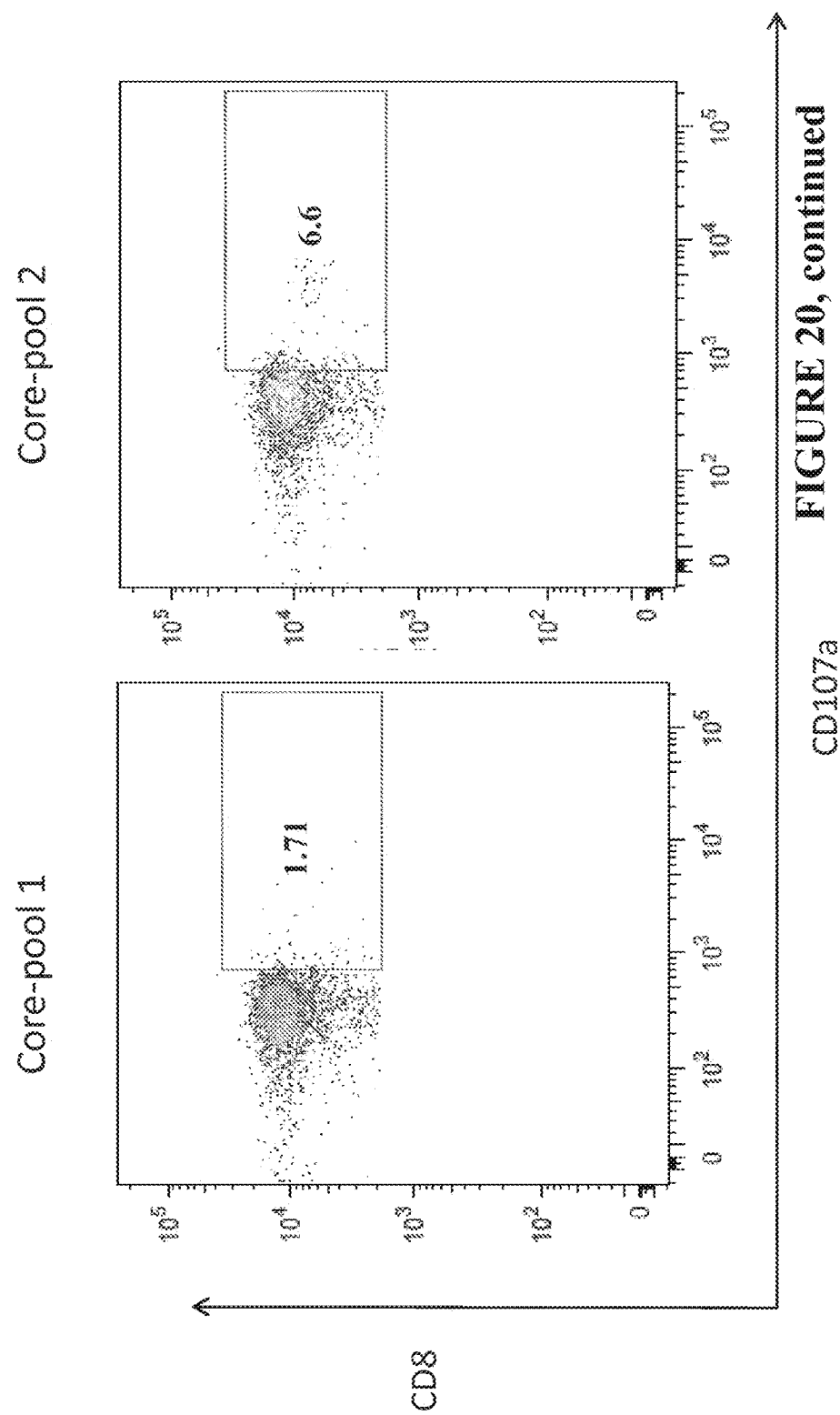
FIGURE 20, continued

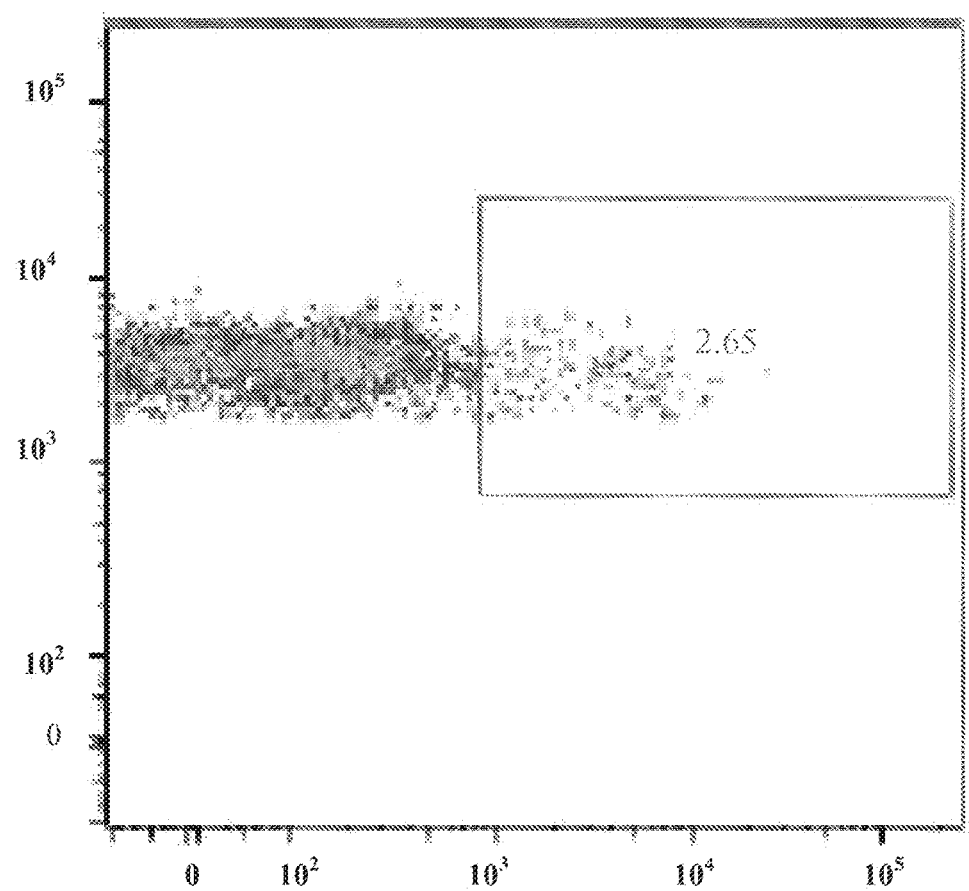
FIGURE 24, continued

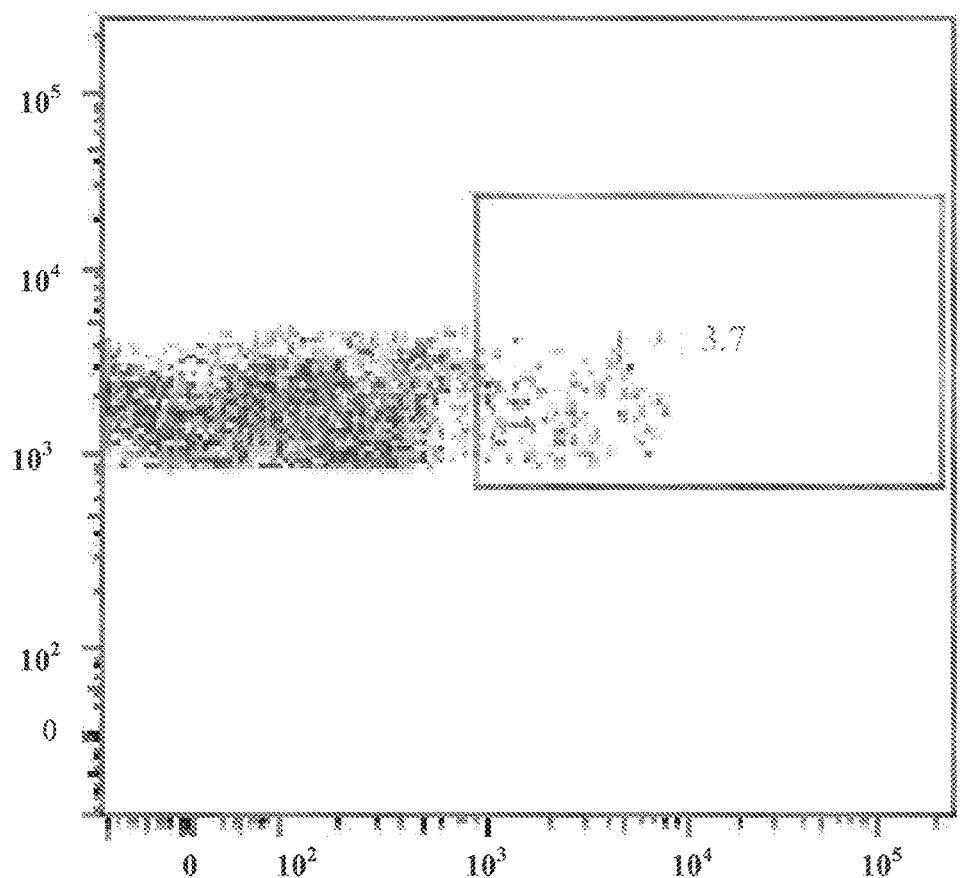
FIGURE 24, continued

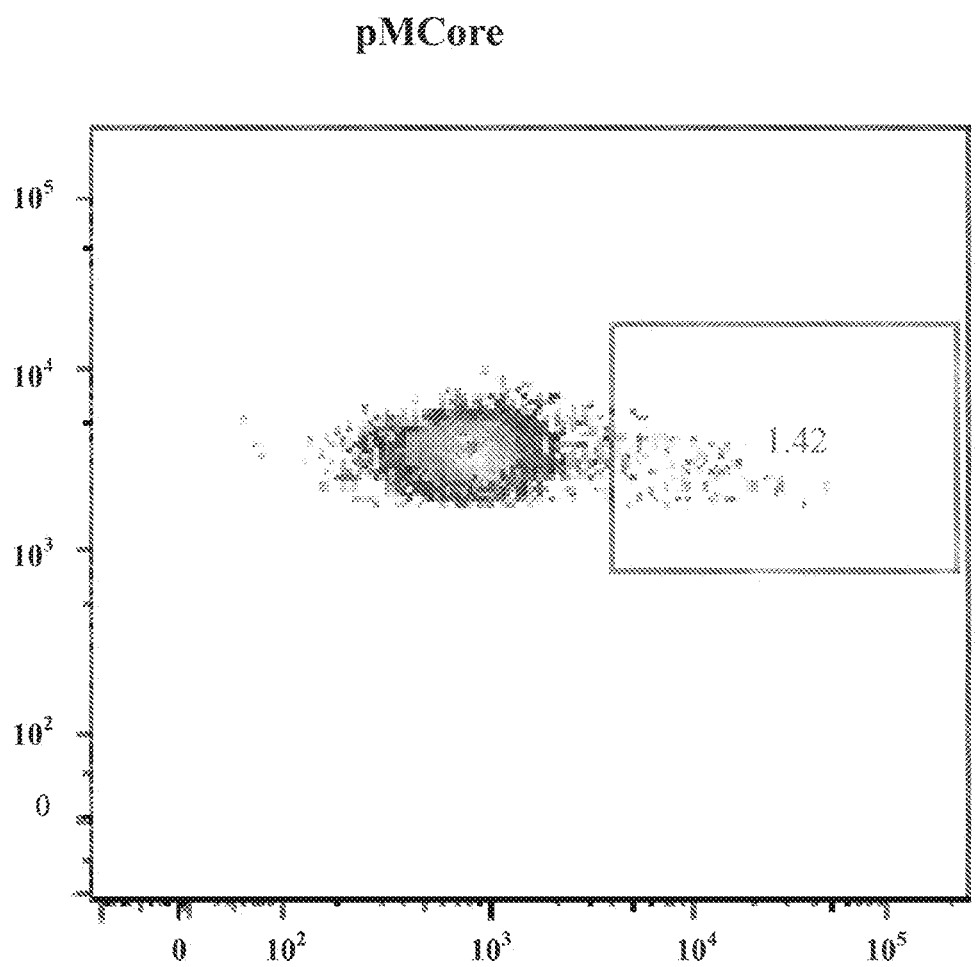
FIGURE 26, continued

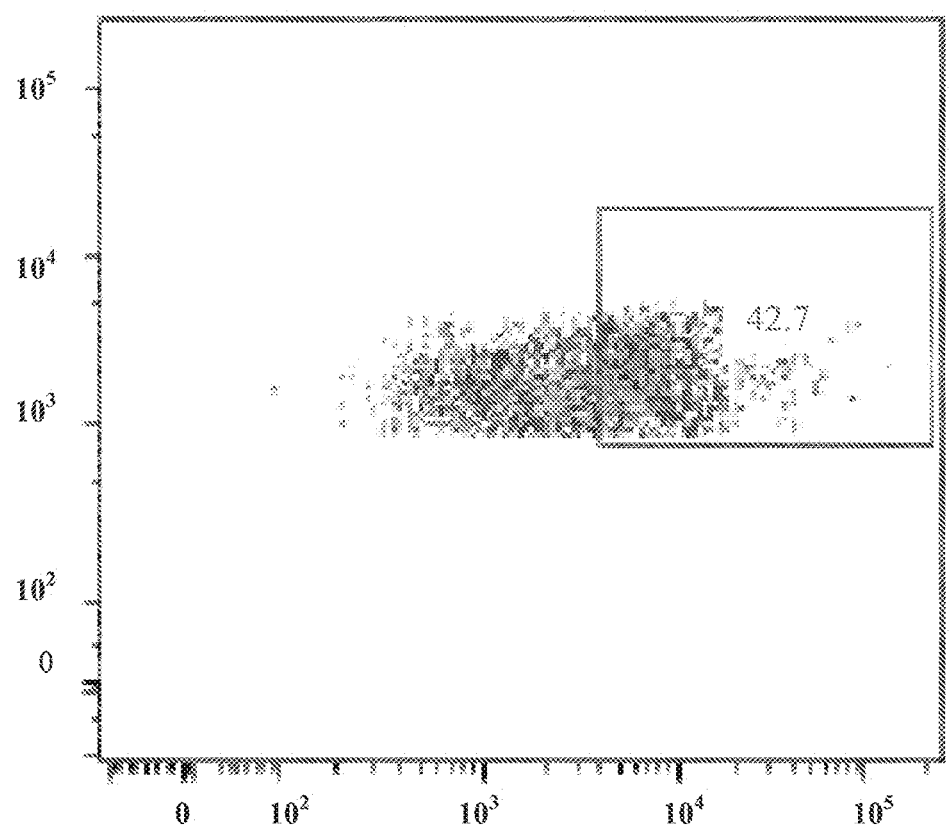
FIGURE 26, continued

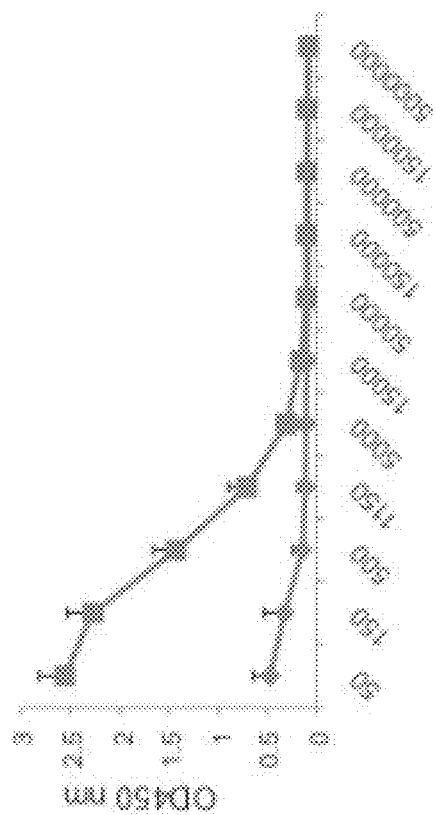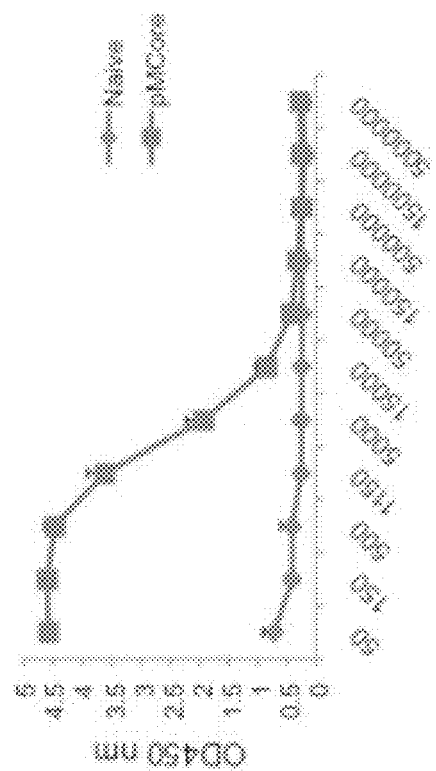
FIGURE 38

NUCLEIC ACID MOLECULE ENCODING HEPATITIS B VIRUS CORE PROTEIN AND SURFACE ANTIGEN PROTEIN AND VACCINE COMPRISING THE SAME

FIELD OF THE INVENTION

The present invention relates to nucleic acid sequences encoding hepatitis B virus (HBV) core proteins, surface antigen proteins, fragments and combinations thereof, to hepatitis B virus (HBV) core proteins, surface antigen proteins, fragments and combinations thereof, to improved HBV vaccines, to improved methods for inducing immune responses against HBV, and to improved methods for prophylactically and/or therapeutically immunizing individuals against HBV.

BACKGROUND

Hepatitis B is a common infection prevalent across the globe that leads to the development of cirrhosis, liver failure, and hepatocellular carcinoma. A significant number of hepatitis cases go unreported due to the asymptomatic nature of the disease. Nevertheless, about 350 million chronic Hepatitis B cases are reported every year. Most of the hepatitis infected population is in underdeveloped or developing countries.

The virus is divided into four major serotypes (adr, adw, ayr, ayw) based on antigenic epitopes present on its envelope proteins. There are at least eight genotypes (A-H) of HBV according to variation of the genomic sequences. The alternative genotypes of HBV have prevalent geographic distribution.

Table 1 shows the geographic distribution of HBV genotypes.

TABLE 1

Geographic Distribution of HBV

| HBV genotype | HBV genosubtype | HBsAg subtype | Frequency | Main geographical distribution |
|---|---|---|---|---|
| A | A2 | adw2 | High | Europe, North America, Australia |
|   | A1 | ayw1, adw2 | High | Africa |
| B | B1 B2, B3 | adw2 | High | Far East |
|   | B4 | ayw1 | High | Far East |
|   | B2 | adw3 | Low | Far East |
| C | C1, C2, C4 | adr | High | Far East |
|   | C3 | adrq- | High | New Guinea., Pacific |
|   | C1, C2 | ayr | High | Far East |
|   | C1, C3 | adw2 | Low | Far East |
|   | C4 | ayw3 | Low | Far East, Pacific |
| D | D1, D3, D4 | ayw2 | High | West Asia, Eastern Europe, Mediterranean |
|   | D2, D3 | ayw3 | High | Worldwide |
|   | Not identified | adw3 | Low | Eastern Europe, Spain |
|   | D2 | ayw4 | Low | Eastern Europe, Spain, United States |
| E | — | ayw4 | High | Africa |
| F | F1, F2 | adw4q- | High | Latin America, Alaska, Pacific |
|   | F1, F2 | ayw4 | Low | Latin America |
| G | — | adw2 | Low | Europe, North America |
| H | — | ayw4 | Low | Central America |

J. Med. Virol, DOI 10.1002jmv

The HBV genome is a circular DNA molecule that is primarily double stranded but which has a single stranded region arising from one strand being longer than the other The double stranded region arises from the hybridization of one strand of a shorter strand of about 3020 nucleotides to a longer strand of about 3320 nucleotides. The single stranded region on non-hybridized nucleotides of the longer strand is associated with the HBV DNA polymerase. The HBV genomic DNA and HBV DNA polymerase are both contained within a nucleocapsid formed by multiple HBV core protein (HBcAg) molecules. The HBV core protein is enveloped by HBV surface protein or antigen (HBsAgs) and lipid molecules.

The HBV genome contains four open reading frames (ORFs): 1) an ORF that encodes the HBV DNA polymerase, 2) an ORF that has two start codons, wherein the sequence linked to the second start codon encodes the core protein and the sequence that includes the additional upstream start codon encodes a sequence referred to as pre-C; 3) an ORF that has three start codons, wherein one encodes the surface protein (S protein; gp27), one includes an upstream start codon which encodes a sequence referred to as pre-S2 (gp36) and another which includes a start codon further upstream which encodes a sequence referred to as pre-S1 (gp42); and 4) an ORF that encodes HBxAg, a protein whose function is less understood (FIG. 1).

Features of the HBsAgs are illustrated in FIG. 2. Epitopes of the HBsAgs involved in the expression of subtype specificities are located in a region that includes the two external loops of the HBV surface antigen molecules (i.e., amino acids 110-180 of S protein) and are what make the HBV strains antigenically diverse. The same region contains an unknown number of epitopes that define the "a" determinant of HBsAg, which is common to all of the HBV wild-type strains known.

Prophylactic vaccines and therapies for HBV infection involve injection of subviral particles purified from plasma of chronic carriers, or subviral particles produced as recombinant proteins in stably transfected eukaryotic cell lines. The subviral particles are viral proteins and such vaccines are often referred to as subunit vaccines. The HBV proteins are administered to an individual and become targets for the individual's immune system. In uninfected individuals, an immune response against the subunit vaccine protects the uninfected individual from HBV infection. In infected individuals, the immune response induced by the vaccine can have therapeutic effects.

Chisari F. V., Am J. Pathol., 2000. 156:1117-1132 and Pumpeus P. et al. Intervirology 2001. 44:98-114 disclose HBV genomic organization. Deny P. and F. Zoulim, Pathologie Biologie 2010, August, 58(4):245 53 discuss hepatitis B virus diagnosis and treatment. Michel M. L. and P. Tiollais, Pathologie Biologie 2010, August, 58(4):288 95 discuss hepatitis B vaccines and their protective efficacy and therapeutic potential. PCT publication WO2004026899 discloses the use of immunogen containing polypeptide sequence with HBV amino acid sequences. PCT published application WO2008093976 discloses HBV coding sequences, proteins and vaccines including a vaccine comprising a recombinant full length HBV surface antigen and HBV core antigen. The entire HBV surface antigen consists of three types of surface protein (L protein, M protein and S protein). PCT published application WO2009130588 discloses HBV coding sequences, proteins and vaccines including a nucleic acid encoding a hepatitis B virus core antigen that is codon optimized for expression in humans. PCT publication WO2010127115 discloses delivery of HBV sequences using recombinant vectors.

The available HBV vaccines have exhibited some efficacy, but are costly to produce. In addition, plasma-derived subunit vaccines also have concerns about safety. Several vaccine approaches have been explored including those based on recombinant live vectors, synthetic peptides, and DNA vaccines that comprise codon optimized coding sequences of HBV proteins. These other approaches have thus far had varying limited efficacy. Additionally, due to genomic differences, some HBV vaccines have exhibited positive efficacy in some geographic areas and limited efficacy in other areas.

Currently available HBsAg-based vaccines derived from yeast transfected with DNA encoding S protein (e.g., ENGERIX-B available from SmithKline Biologicals located in Belgium and RECOMBIVAX/HB-VAX II available from Merck & Co. located in the U.S.A.) do not elicit a response in about 5% to 10% of individuals (C. Belloni, Immunogenicity of hepatitis B vaccine in term and preterm infants. Acta Paediatrica, 1998. 87: p. 336-338). Additionally, the rate of non-response increases to 30% in older individuals and immunity against HBV can decrease several years after vaccination. Multiple doses are also needed to attain complete protection. Safety is of concern with the HBsAg-based vaccine ENGERIX-B as ENGERIX-B triples the risk of central nervous system (CNS) inflammatory demyelination.

Other HBsAg-based vaccines derived from mammalian cells utilize pre-S1 and pre-S2 in addition to S protein. The pre-S1 and -S2 antigens express highly immunogenic T and B cell epitopes and one such vaccine elicits an immune response in about 80% of non- or low-responding individuals (Rendi-Wagner, P. et al., Comparative immunogenicity of PreS/S hepatitis B vaccine in non- and low responders to conventional vaccine. Vaccine, 2006. 24: p. 2781-9.).

The direct administration of nucleic acid sequences to vaccinate against animal and human diseases has been studied and much effort has focused on effective and efficient means of nucleic acid delivery in order to yield necessary expression of the desired antigens, resulting immunogenic response and ultimately the success of this technique.

DNA vaccines allow for endogenous antigen synthesis, which induces CD8+ histocompatible complex, class I-restricted cytotoxic T lymphocytes that are rarely obtained with subunit vaccines. In addition, the antigen synthesis that occurs over a sustained period can help overcome low responsiveness and eliminate or reduce the requirement for booster injections. Further, DNA vaccines appear to be very stable and simple to produce. Moreover, broader cellular immune responses can be induced by combining strategies like codon optimization, RNA optimization and adding immunoglobulin leader sequences.

DNA vaccines are safe, stable, easily produced, and well tolerated in humans with preclinical trials indicating little evidence of plasmid integration [Martin, T., et al., Plasmid DNA malaria vaccine: the potential for genomic integration after intramuscular injection. Hum Gene Ther, 1999. 10(5): p. 759-68; Nichols, W. W., et al., Potential DNA vaccine integration into host cell genome. Ann N Y Acad Sci, 1995. 772: p. 30-9]. In addition, DNA vaccines are well suited for repeated administration due to the fact that efficacy of the vaccine is not influenced by pre-existing antibody titers to the vector [Chattergoon, M., J. Boyer, and D. B. Weiner, Genetic immunization: a new era in vaccines and immune therapeutics. FASEB J, 1997. 11(10): p. 753-63]. However, one major obstacle for the clinical adoption of DNA vaccines has been a decrease in the platform's immunogenicity when moving to larger animals [Liu, M. A. and J. B. Ulmer, Human clinical trials of plasmid DNA vaccines. Adv Genet, 2005. 55: p. 25-40].

Recent technological advances in the engineering of DNA vaccine immunogen have improved expression and immunogenicity of DNA vaccines, such has codon optimization, RNA optimization and the addition of immunoglobulin leader sequences [Andre, S., et al., Increased immune response elicited by DNA vaccination with a synthetic gp120 sequence with optimized codon usage. J Virol, 1998. 72(2): p. 1497-503; Deml, L., et al., Multiple effects of codon usage optimization on expression and immunogenicity of DNA candidate vaccines encoding the human immunodeficiency virus type 1 Gag protein. J Virol, 2001. 75(22): p. 10991-1001; Laddy, D. J., et al., Immunogenicity of novel consensus-based DNA vaccines against avian influenza. Vaccine, 2007. 25(16): p. 2984-9; Frelin, L., et al., Codon optimization and mRNA amplification effectively enhances the immunogenicity of the hepatitis C virus nonstructural 3/4A gene. Gene Ther, 2004. 11(6): p. 522-33], as well as, recently developed technology in plasmid delivery systems such as electroporation [Hirao, L. A., et al., Intradermal/subcutaneous immunization by electroporation improves plasmid vaccine delivery and potency in pigs and rhesus macaques. Vaccine, 2008. 26(3): p. 440-8; Luckay, A., et al., Effect of plasmid DNA vaccine design and in vivo electroporation on the resulting vaccine-specific immune responses in rhesus macaques. J Virol, 2007. 81(10): p. 5257-69; Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-53]. The in vivo electroporation technique has been used in human clinical trials to deliver anti-cancer drugs, such as bleomycin, and in many preclinical studies on a large number of animal species. In addition, studies have suggested that the use of consensus immunogens can be able to increase the breadth of the cellular immune response as compared to native antigens alone [Yan, J., et al., Enhanced cellular immune responses elicited by an engineered HIV-1 subtype B consensus-based envelope DNA vaccine. Mol Ther, 2007. 15(2): p. 411-21; Rolland, M., et al., Reconstruction and function of ancestral center-of-tree human immunodeficiency virus type 1 proteins. J Virol, 2007. 81(16): p. 8507-14].

There remains a need for nucleic acid constructs that encode HBV protein and for compositions useful to induce immune responses against HBV. There remains a need for effective vaccines against HBV that are economical and effective. There remains a need for effective vaccines that increase neutralizing antibody levels and elicit a T-cell component. There remains a need for effective vaccines against HBV, including those that are effective against HBV strains having a broad range of genotypes, and preferably, a universal vaccine that would be globally effective.

SUMMARY OF INVENTION

The present invention is directed to a vaccine comprising: (a) a nucleic acid molecule encoding one or more proteins selected from the group consisting of: SEQ ID NO:2, SEQ ID NO:4, and SEQ ID NO:6; (b) a nucleic acid molecule encoding one or more proteins selected from the group consisting of: SEQ ID NO:10, SEQ ID NO:14, a protein that is 98% homologous to SEQ ID NO:10, and a protein that is 98% homologous to SEQ ID NO:14; and (c) a nucleic acid molecule encoding one or more proteins selected from the group consisting of: SEQ ID NO: 12, SEQ ID NO:16, a protein that is 98% homologous to SEQ ID NO:12, and a protein that is 98% homologous to SEQ ID NO:16. The nucleic acid molecules can comprise one or more nucleotide sequences selected from the group consisting of: SEQ ID NO:1, SEQ ID NO:3, SEQ ID NO:5, SEQ ID NO:9, SEQ ID NO:11, SEQ ID NO:13, and SEQ ID NO:15.

The present invention may also be directed to a vaccine comprising (a) a nucleic acid molecule encoding one or more proteins selected from the group consisting of: SEQ ID NO:2, SEQ ID NO:4, and SEQ ID NO:6; (b) a nucleic acid molecule encoding one or more proteins selected from the group consisting of: SEQ ID NO:10, SEQ ID NO:14, a protein that is 95% identical to the full length amino acid sequence of SEQ ID NO:10, and a protein that is 95% identical to the full length amino acid sequence of SEQ ID NO:14; and (c) a nucleic acid molecule encoding one or more proteins selected from the group consisting of: SEQ ID NO: 12, SEQ ID NO:16, a protein that is 95% identical to the full length amino acid sequence of SEQ ID NO:12, and a protein that is 95% identical to the full length amino acid sequence of SEQ ID NO:16.

The vaccine can be a plasmid comprising the nucleic acids described above. The nucleic acid molecules can be incorporated into viral particles. The vaccine can further comprise an adjuvant molecule. The adjuvant can be IL-12, IL-15, IL-28, or RANTES.

The present invention is also directed to a method of inducing an immune response against an HBV antigen comprising administering a vaccine of the present invention to a subject.

The present invention is also directed to a method of protecting a subject from HBV infection comprising administering a vaccine of the present invention to the subject.

The present invention is further directed to a method of protecting a subject who has been diagnosed with HBV infection comprising administering a vaccine of the present invention to the subject.

The present invention further includes vaccines useful for inducing an immune response against HBV. The development of an HBV immune therapeutic vaccine with broad effectiveness against a multitude of genotypes can be provided using a therapeutic DNA vaccine for HBV infection based on targeting the universally conserved HBV-core specific antigens. The utilization of consensus HBV immunogens induces broader cellular immune responses and can be useful to minimize the degree of sequence dissimilarity among different virus strains.

Provided herein are proteins selected from the group consisting of: proteins comprising SEQ ID NO:2, proteins that are 95% homologous to SEQ ID NO:2; fragments of SEQ ID NO:2; proteins that are 95% homologous to a fragment of SEQ ID NO:2; SEQ ID NO:4, proteins that are 95% homologous to SEQ ID NO:4; fragments of SEQ ID NO:4; proteins that are 95% homologous to a fragment of SEQ ID NO:4 SEQ ID NO:6, proteins that are 95% homologous to SEQ ID NO:6; fragments of SEQ ID NO:6; and proteins that are 95% homologous to a fragment of SEQ ID NO:6.

Provided also herein is a protein selected from the group consisting of (a) SEQ ID NO:2; (b) a protein that is 95% identical to the full length sequence as set forth in SEQ ID NO:2; (c) an immunogenic fragment of SEQ ID NO:2 comprising 20 or more amino acids of SEQ ID NO:2; and (d) an immunogenic fragment of a protein that is 95% identical to SEQ ID NO:2 comprising 20 or more amino acids.

Nucleic acid molecules comprising sequences that encode one or more protein molecules set forth above are also provided. In some embodiments, the nucleic acid molecule comprises a sequence selected from the group consisting of: SEQ ID NO:1; a nucleic acid sequence that is 95% homologous to SEQ ID NO:1; a fragment of SEQ ID NO:1; a nucleic acid sequence that is 95% homologous to a fragment of SEQ ID NO:1; SEQ ID NO:3; a nucleic acid sequence that is 95% homologous to SEQ ID NO:3; a fragment of SEQ ID NO:3; a nucleic acid sequence that is 95% homologous to a fragment of SEQ ID NO:3; SEQ ID NO:5; a nucleic acid sequence that is 95% homologous to SEQ ID NO:5; a fragment of SEQ ID NO:5; and a nucleic acid sequence that is 95% homologous to a fragment of SEQ ID NO:5.

Some aspects of the invention provide methods of inducing an immune response against core antigen from one or more HBV genotypes comprising the step of: administering to an individual such nucleic acid molecules and/or compositions.

Additional aspects of the invention provide methods of protecting an individual against HBV infection. The methods comprise the step of: administering to said individual a prophylactically effective amount of a nucleic acid molecule comprising such nucleic acid sequence or compositions; wherein the nucleic acid sequence is expressed in cells of said individual and a protective immune response is induced against a protein encoded by said nucleic acid sequence.

In some aspects of the invention, methods are provided for treating an individual who has been infected by HBV. The methods comprise the step of: administering to said individual a therapeutically effective amount of such nucleic acid molecules and/or composition.

The present invention provides in another aspect a nucleic acid molecule comprising a coding sequence that encodes one or more proteins selected from the group consisting of: (a) a protein comprising SEQ ID NO:10, SEQ ID NO:12, SEQ ID NO:14, or SEQ ID NO:16; (b) a protein that is 98% homologous to SEQ ID NO:10, SEQ ID NO:12, SEQ ID NO:14, or SEQ ID NO:16; (c) an immunogenic fragment of a protein comprising SEQ ID NO:10, SEQ ID NO:12, SEQ ID NO:14, or SEQ ID NO:16 that is at least 20 amino acids; and (d) an immunogenic fragment of a protein that is 98% homologous to SEQ ID NO:10, SEQ ID NO:12, SEQ ID NO:14, or SEQ ID NO:16 that is at least 20 amino acids.

The nucleic acid molecule can comprise one or more sequences selected from the group consisting of: (a) a nucleic acid sequence comprising SEQ ID NO:9, SEQ ID NO:11, SEQ ID NO:13, or SEQ ID NO:15; (b) a nucleic acid sequence that is 98% homologous to SEQ ID NO:9, SEQ ID NO:11, SEQ ID NO:13, or SEQ ID NO:15; (c) fragments thereof that comprise a nucleic acid sequence encoding immunogenic fragments comprising at least 20 amino acids encoded by SEQ ID NO:9, SEQ ID NO:11, SEQ ID NO:13, or SEQ ID NO:15; and (d) fragments thereof that comprise a nucleic acid sequence encoding immunogenic fragments comprising at least 20 amino acids of a protein that is 98% homologous to a protein encoded by SEQ ID NO:9, SEQ ID NO:11, SEQ ID NO:13, or SEQ ID NO:15. The nucleic acid molecule can be a plasmid. The nucleic acid molecule can be an expression vector and sequences encoding said one or more proteins are operably linked to regulatory elements. The nucleic acid molecule can be incorporated into a viral particle.

Some aspects of the invention provide a method of inducing an immune response against an HBV antigen comprising administering a nucleic acid molecule of the present invention to a subject.

Some aspects of the invention provide a method of protecting a subject from HBV infection comprising administering a nucleic acid molecule of present invention to the subject.

Some aspects of the invention provide a method of protecting a subject who has been diagnosed with HBV infection comprising administering a nucleic acid molecule of the present invention to the subject.

The present invention provides in yet another aspect a protein selected from the group consisting of: (a) SEQ ID NO:10, SEQ ID NO:12, SEQ ID NO:14, or SEQ ID NO:16; (b) a protein that is 98% homologous to SEQ ID NO:10, SEQ ID NO:12, SEQ ID NO:14, or SEQ ID NO:16; (c) an immunogenic fragment of SEQ ID NO:10, SEQ ID NO:12, SEQ ID NO:14, or SEQ ID NO:16 comprising 20 or more amino acids; and (d) an immunogenic fragment of a protein that is 98% homologous to SEQ ID NO:10, SEQ ID NO:12, SEQ ID NO:14, or SEQ ID NO:16 comprising 20 or more amino acids.

Some aspects of the invention provide a vaccine useful for generating an immune response against HBV in a subject comprising: a nucleic acid molecule of the present invention, and an adjuvant molecule. The adjuvant can be IL-12, IL-15, IL-28, or RANTES.

BRIEF DESCRIPTION OF THE DRAWINGS

FIG. 11A shows results from in vitro translation protocol. FIG. 11B shows results of a Western Blot.

FIG. 19 shows the enhanced magnitude of TNF-α secretion in CD8+ and CD4+ T Cells from the spleens of Balb/C mice vaccinated with pM-Core.

FIG. 20 shows the enhanced magnitude of CD 107a secretion in CD8+ and CD4+ T Cells from the spleens of Balb/C mice vaccinated with pM-Core.

FIG. 38 shows the HBcAg-specific humoral immune response induced by pMCore in the sera and splenocytes. The values are the means±standard error of the mean. Significance was determined by Student's t test.

DETAILED DESCRIPTION

Figure 1:
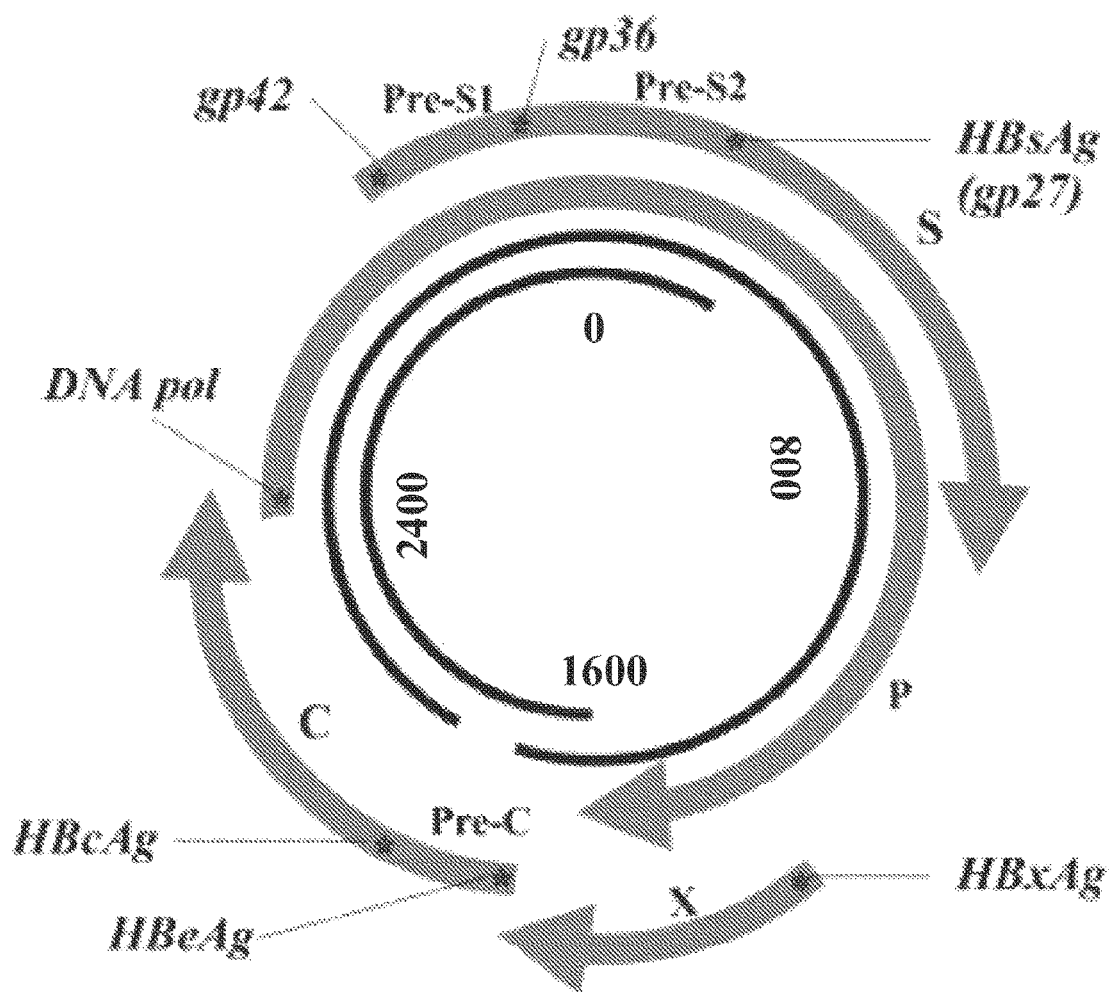
FIG. 1 is a map showing the organization of the HBV genome which consists of four overlapping ORFs.
Figure 2:
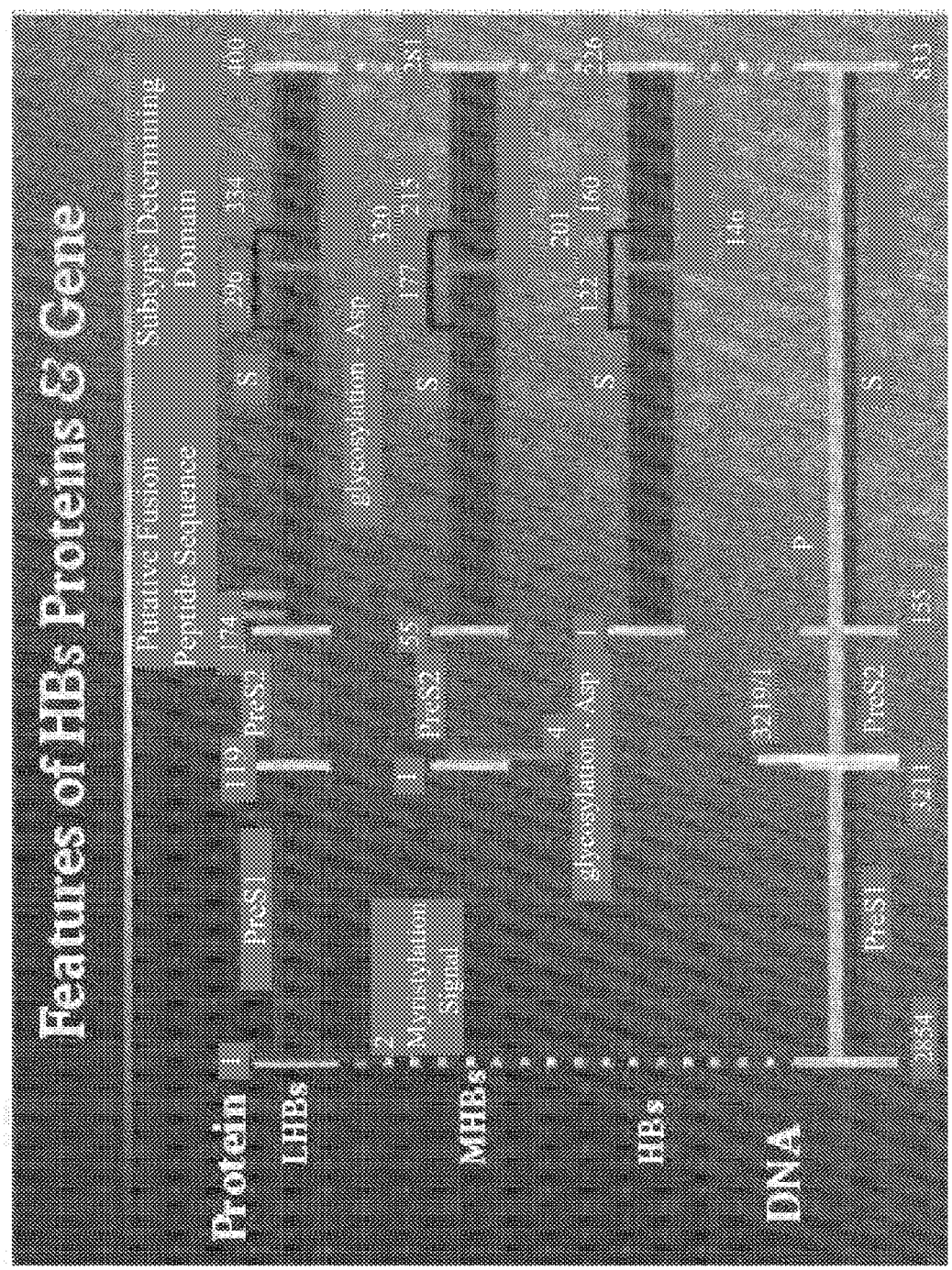
FIG. 2 illustrates the organization and features of the HBV surface antigens.

The present invention relates to vaccines for Hepatitis B virus (HBV) that can be used to protect an individual from HBV infection and to provide therapeutic benefits to an individual diagnosed with HBV infection. Such vaccines can also be used to induce an immune response against an HBV antigen. The HBV vaccine of the present invention includes one or more nucleic acid molecules. Particularly, the nucleic acid molecule encodes one or more consensus HBV core proteins. The consensus HBV core proteins are derived from the sequences of the core proteins from HBV genotypes A, B, C, D, and E, and therefore the consensus HBV core proteins are unique. The nucleic acid molecules can also encode one or more immunogenic fragments of the consensus HBV core proteins.

Additionally, the nucleic acid molecules can encode one or more consensus HBV surface antigens. The consensus HBV surface antigens are derived from sequences of the surface antigens from isolates of HBV genotype A, and therefore the consensus HBV surface antigens are unique. The consensus HBV surface antigens can also be derived from sequences of the surface antigens from isolates of HBV genotype C, resulting in unique HBV surface antigens. The nucleic acid molecules can also encode one or more immunogenic fragments of the consensus HBV surface antigens.

The vaccine of the present invention can include any combination of nucleic acid molecules encoding the consensus HBV core protein and/or nucleic acid molecules encoding the consensus HBV surface antigen. The vaccine can also include any combination of nucleic acid molecules encoding immunogenic fragments of the consensus HBV core proteins and/or nucleic acid molecules encoding immunogenic fragments of the consensus HBV surface antigens.

These combinations of the HBV core protein and HBV surface antigen surprisingly and unexpectedly induce a differential immune response to the HBV core protein and HBV surface antigen. In other words, the strength of the immune response to the HBV core protein and HBV surface antigen differs depending on the specific combination administered to a subject. Accordingly, any user of the vaccine of the present invention can design a vaccine that comprises a specific combination to induce a desired immune response in a subject administered such a designed vaccine. As such, any user can tailor the vaccine of the present invention to control the level of the immune response in the subject.

The vaccine of the present invention is widely applicable to multiple types of HBV because of the unique consensus sequences of the HBV core protein and HBV surface antigen.

The vaccine of the present invention can further include one or more nucleic acid molecules as described above and one or more proteins encoded by such nucleic acid molecules.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Adjuvant" as used herein means any molecule added to the DNA plasmid vaccines described herein to enhance the immunogenicity of the antigens encoded by the DNA plasmids and the encoding nucleic acid sequences described hereinafter.

"Antibody" as used herein means an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

"Complement" or "complementary" as used herein means a nucleic acid can mean Watson-Crick (e.g., A-T/U and C-G) or Hoogsteen base pairing between nucleotides or nucleotide analogs of nucleic acid molecules.

"Consensus" or "consensus sequence" as used herein means a polypeptide sequence based on analysis of an alignment of multiple subtypes of a particular HBV antigen such as an HBV core or surface antigen. Nucleic acid sequences that encode a consensus polypeptide sequence can be prepared. Vaccines comprising proteins that comprise consensus sequences and/or nucleic acid molecules that encode such proteins can be used to induce broad immunity against multiple subtypes or serotypes of a particular HBV antigen.

"Electroporation," "electro-permeabilization," or "electrokinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

"Fragment" as used herein with respect to nucleic acid sequences means a nucleic acid sequence or a portion thereof, that encodes a polypeptide capable of eliciting an immune response in a mammal that cross reacts with a full length wild type strain HBV antigen. The fragments can be DNA fragments selected from at least one of the various nucleotide sequences that encode protein fragments set forth below.

"Fragment" or "immunogenic fragment" with respect to polypeptide sequences means a polypeptide capable of eliciting an immune response in a mammal that cross reacts with a full length wild type strain HBV antigen. Fragments of consensus proteins can comprise at least 10%, at least 20%, at least 30%, at least 40%, at least 50%, at least 60%, at least 70%, at least 80%, at least 90% or at least 95% of a consensus protein. In some embodiments, fragments of consensus proteins can comprise at least 20 amino acids or more, at least 30 amino acids or more, at least 40 amino acids or more, at least 50 amino acids or more, at least 60 amino acids or more, at least 70 amino acids or more, at least 80 amino acids or more, at least 90 amino acids or more, at least 100 amino acids or more, at least 110 amino acids or more, at least 120 amino acids or more, at least 130 amino acids or more, at least 140 amino acids or more, at least 150 amino acids or more, at least 160 amino acids or more, at least 170 amino acids or more, at least 180 amino acids or more, at least 190 amino acids or more, at least 200 amino acids or more, at least 210 amino acids or more, at least 220 amino acids or more, at least 230 amino acids or more, or at least 240 amino acids or more of a consensus protein.

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

The term "homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Immune response" as used herein means the activation of a host's immune system, e.g., that of a mammal, in response to the introduction of antigen such as an HBV consensus antigen. The immune response can be in the form of a cellular or humoral response, or both.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Signal peptide" and "leader sequence" are used interchangeably herein and refer to an amino acid sequence that can be linked at the amino terminus of an HBV protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point (Tm) for the specific sequence at a defined ionic strength pH. The Tm can be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

"Substantially identical" as used herein means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

"Subtype" or "serotype": as used herein, interchangeably, and in reference to HBV, means genetic variants of an HBV such that one subtype is recognized by an immune system apart from a different subtype.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

2. Vaccines

The present invention is directed to a Hepatitis B vaccine. The Hepatitis B vaccine (HBV) can comprise a nucleic acid encoding a HBV core antigen, a HBV surface antigen, or a combination thereof, a HBV core antigen, a HBV surface antigen, or combination thereof, or a combination of (1) nucleic acid encoding a HBV core antigen, a HBV surface antigen, and (2) a HBV core antigen, a HBV surface antigen, or (3) combinations thereof. The HBV core antigen can comprise a consensus protein derived from the amino acid sequences of core proteins from multiple HBV genotypes. Similarly, the HBV surface antigen can comprise a consensus protein derived from the amino acid sequences of surface antigens from multiple HBV genotypes. Such consensus HBV core proteins and consensus HBV surface antigens are unique and have similarity to core and surface antigens, respectively, across multiple HBV genotypes. As such, the vaccine of the present invention is applicable to multiple types of HBV and is useful for widespread populations. Additionally, the vaccine of the present invention can be tailored to particular nucleic acids encoding consensus HBV core protein, consensus HBV surface protein, or a combination thereof. In other words, the vaccine of the present invention can be designed to control the level or strength of the immune response in the subject against one or more HBV serotypes.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

The vaccine can be an RNA of the HBV core protein and/or the HBV surface antigen protein. The RNA vaccine can be introduced into the cell.

a. HBV Core Antigen

The vaccine of the present invention can comprise a HBV core protein. The HBV core protein is an important target for immune mediated viral clearance by inducing 1) cytotoxic T lymphocyte (CTL) responses, 2) T helper cell responses, and/or 3) B cell responses, or preferably all of the aforementioned, for cross presentation.

Table 2 shows the similarities across genotypes for core antigen from HBV-A, HBV-B, HBV-C, HBV-D and HBV-E genotypes with the consensus HBV core proteins, referred to in the chart as "HBV-M-core". For some embodiments, the HBV M Core construct was designed to have increased homologies for broad HBV core targets. Similarities in the genotypes for Core Antigen with designed M-Core construct—increased homologies for broad HBV core targets. All genotypes should be represented in a universal immune therapeutic vaccine for HBV.

TABLE 2

Percent Identities of HBV Core Proteins
Percent Identity

| | | 1 | 2 | 3 | 4 | 5 | 6 | |
|---|---|---|---|---|---|---|---|---|
| Divergence | 1 | | 96.2 | 96.2 | 97.8 | 95.6 | 98.4 | 1 - HBV-A-ConCore |
| | 2 | 3.9 | | 100 | 95.6 | 93.4 | 96.7 | 2 - HBV-B-ConCore |
| | 3 | 3.9 | 0 | | 95.6 | 93.4 | 96.7 | 3 - HBV-C-ConCore |
| | 4 | 2.2 | 4.5 | 4.5 | | 97.8 | 97.8 | 4 - HBV-D-ConCore |
| | 5 | 4.5 | 6.9 | 6.9 | 2.2 | | 95.6 | 5 - HBV-E-ConCore |
| | 6 | 1.7 | 3.4 | 3.4 | 2.2 | 4.5 | | 6 - HBV-M-Core |
| | | 1 | 2 | 3 | 4 | 5 | 6 | |

The antigen can comprise core protein epitopes that make them particularly effective as immunogens against which anti-HBV immune responses can be induced. The HBV antigen can comprise the full length translation product, a variant thereof, a fragment thereof or a combination thereof.

The HBV core antigen can comprise a consensus protein. The HBV consensus core antigen induces antigen-specific T-cell and high titer antibody responses both systemically and in the liver. As such, a protective immune response is provided to the liver by vaccines comprising the HBV consensus core antigen. Accordingly, any user can design a vaccine of the present invention to include an HBV consensus core antigen to provide immune-based therapy and/or protection to the liver.

Particularly in the induced immune response, the HBV consensus core antigen stimulates splenocytes, specifically CD4+ cells and CD8+ cells, to secrete or produce similar amounts of interferon-gamma (INF-γ), but different amounts of tumor necrosis factor-alpha (TNF-α). Interestingly, the induced immune response differs in the spleen and liver. In the spleen, more CD8+ cells produce both INF-γ and TNF-α than CD4+ cells, however in the liver, the opposite occurs. In other words, more CD4+ cells produce both INF-γ and TNF-α than CD8+ cells in the liver. Additionally, in the liver, more antigen-specific IgA than IgG is produced, and and the protective immune response surprisingly and unexpectedly includes an antigen-specific CTL response, which does not cause liver damage. Accordingly, a vaccine of the present invention comprising an HBV consensus core antigen can be delivered in the periphery to establish an antigen-specific targeting the liver to clear or eliminate HBV infected cells without causing damage to or inflammation of the liver.

The nucleic acid sequences encoding the consensus HBV core proteins are SEQ ID NO:1, SEQ ID NO:3, and SEQ ID NO:5. SEQ ID NO:1 encodes an HBV consensus core protein. SEQ ID NO:3 encodes the HBV consensus core protein linked to an IgE leader. SEQ ID NO:5 encodes the HBV consensus core protein linked to the IgE leader and an HA tag.

Some embodiments relate to nucleic acid sequences encoding proteins homologous to the HBV consensus protein, immunogenic fragment of the HBV consensus protein, and immunogenic fragments of homologous proteins. Such nucleic acid molecules that encode immunogenic proteins that have up to 95% homology to a consensus sequence, up to 96% homology to a consensus sequence, up to 96% homology to a consensus sequence, up to 97% homology to a consensus sequence, up to 98% homology to a consensus sequence and up to 99% can be provided. Likewise, nucleic acid sequences encoding the immunogenic fragments set forth herein and the immunogenic fragments of proteins homologous to the proteins set forth herein are also provided.

Some embodiments relate to nucleic acid molecules that encode immunogenic proteins that have 95% homology to the nucleic acid coding sequences herein. Some embodiments relate to nucleic acid molecules that encode immunogenic proteins that have 96% homology to the nucleic acid coding sequences herein. Some embodiments relate to nucleic acid molecules that encode immunogenic proteins that have 97% homology to the nucleic acid coding sequences herein. Some embodiments relate to nucleic acid molecules that encode immunogenic proteins that have 98% homology to the nucleic acid coding sequences herein. Some embodiments relate to nucleic acid molecules that encode immunogenic proteins that have 99% homology to the nucleic acid coding sequences herein. In some embodiments, the nucleic acid molecules with coding sequences disclosed herein that are homologous to a coding sequence of a consensus protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length HBV core consensus protein, immunogenic fragment of the HBV core consensus protein, and immunogenic fragments of HBV core consensus proteins. Such nucleic acid molecules that encode immunogenic proteins that have up to 80% identity to a full length HBV core consensus sequence, up to 85% identity to a full length consensus sequence, up to 90% identity to a full length HBV core consensus sequence, up to 91% identity to a full length HBV core consensus sequence, up to 92% identity to a full length HBV core consensus sequence, up to 93% identity to a full length HBV core consensus sequence, up to 94% identity to a full length HBV core consensus sequence, up to 95% identity to a full length HBV core consensus sequence, up to 96% identity to a full length HBV core consensus sequence, up to 97% identity to a full length HBV core consensus sequence, up to 98% identity to a full length HBV core consensus sequence, up to 99% identity to a full length HBV core consensus sequence can be provided. Likewise, nucleic acid sequences encoding the immunogenic fragments set forth herein and the immunogenic fragments of proteins with similar percent identities as indicated above to the HBV core proteins set forth herein are also provided.

Some embodiments relate to nucleic acid molecules that encode immunogenic protein that have 80% identity to the full length nucleic acid HBV core protein coding sequences herein. Some embodiments relate to nucleic acid molecules that encode immunogenic protein that have 83% identity to the full length nucleic acid HBV core protein coding sequences herein. Some embodiments relate to nucleic acid molecules that encode immunogenic proteins that have 85% identity to the full length nucleic acid HBV core protein coding sequences herein. Some embodiments relate to nucleic acid molecules that encode immunogenic proteins that have 90% identity to the full length nucleic acid HBV core protein coding sequences herein. Some embodiments relate to nucleic acid molecules that encode immunogenic proteins that have 91% identity to the full length nucleic acid HBV core protein coding sequences herein. Some embodiments relate to nucleic acid molecules that encode immunogenic proteins that have 92% identity to the full length nucleic acid HBV core protein coding sequences herein. Some embodiments relate to nucleic acid molecules that encode immunogenic proteins that have 93% identity to the full length nucleic acid HBV core protein coding sequences herein. Some embodiments relate to nucleic acid molecules that encode immunogenic proteins that have 94% identity to the full length nucleic acid HBV core protein coding sequences herein. Some embodiments relate to nucleic acid molecules that encode immunogenic proteins that have 95% identity to the full length nucleic acid HBV core protein coding sequences herein. Some embodiments relate to nucleic acid molecules that encode immunogenic proteins that have 96% identity to the full length nucleic acid HBV core protein coding sequences herein. Some embodiments relate to nucleic acid molecules that encode immunogenic proteins that have 97% identity to the full length nucleic acid HBV core protein coding sequences herein. Some embodiments relate to nucleic acid molecules that encode immunogenic proteins that have 98% identity to the full length nucleic acid HBV core protein coding sequences herein. Some embodiments relate to nucleic acid molecules that encode immunogenic proteins that have 99% identity to the full length nucleic acid HBV core protein coding sequences herein. In some embodiments, the nucleic acid molecules with coding sequences disclosed herein that are homologous to a coding sequence of a consensus HBV core protein disclosed herein include sequences encoding an IgE leader sequence linked to the 5' end of the coding sequence encoding the homologous protein sequences disclosed herein.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:1, SEQ ID NO:3 and SEQ ID NO:5. Fragments can be at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of SEQ ID NO:1, SEQ ID NO:3 and SEQ ID NO:5. Fragments can be at least 95%, at least 96%, at least 97% at least 98% or at least 99% homologous to fragments of SEQ ID NO:1, SEQ ID NO:3 and SEQ ID NO:5. Fragments can be at least 80%, at least 85%, at least 90% at least 91%, at least 92%, at least 93%, at least 94%, at least 95%, at least 96%, at least 97%, at least 98% or at least 99% identity to fragments of SEQ ID NO:1, SEQ ID NO:3 and SEQ ID NO:5. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as for example, the IgE leader.

Furthermore, the amino acid sequence of the consensus HBV core protein is SEQ ID NO:2. The amino acid sequence of the consensus HBV core protein linked to an IgE leader is SEQ ID NO:4. Particularly, in SEQ ID NO:4, the IgE leader is linked to the amino terminus of the consensus HBV core protein. The amino acid sequence of the consensus HBV core protein linked to the IgE leader and an HA tag is SEQ ID NO:6. In SEQ ID NO:6, the IgE leader and HA tag are linked to the amino and carboxy termini, respectively, of the consensus HBV core protein.

Some embodiments relate to proteins that are homologous to SEQ ID NO:2, SEQ ID NO:4, and SEQ ID NO:6. Some embodiments relate to immunogenic proteins that have 95% homology to the consensus protein sequences as set forth in SEQ ID NO:2, SEQ ID NO:4, or SEQ ID NO:6. Some embodiments relate to immunogenic proteins that have 96% homology to the consensus protein sequences as set forth in SEQ ID NO:2, SEQ ID NO:4, or SEQ ID NO:6. Some embodiments relate to immunogenic proteins that have 97% homology to the consensus protein sequences as set forth in SEQ ID NO:2, SEQ ID NO:4, or SEQ ID NO:6. Some embodiments relate to immunogenic proteins that have 98% homology to the consensus protein sequences as set forth in SEQ ID NO:2, SEQ ID NO:4, or SEQ ID NO:6. Some embodiments relate to immunogenic proteins that have 99% homology to the consensus protein sequences as set forth in SEQ ID NO:2, SEQ ID NO:4, or SEQ ID NO:6.

Some embodiments relate to proteins that are identical to SEQ ID NO:2, SEQ ID NO:4, or SEQ ID NO:6. Some embodiments relate to immunogenic proteins that have an amino acid sequence that is 80% identical to the full length consensus amino acid sequences as set forth in SEQ ID NO:2, SEQ ID NO:4, or SEQ ID NO:6. Some embodiments relate to immunogenic proteins that have an amino acid sequence that is 85% identical to the full length consensus amino acid sequences as set forth in SEQ ID NO:2, SEQ ID NO:4, or SEQ ID NO:6. Some embodiments relate to immunogenic proteins that have an amino acid sequence that is 90% identical to the full length consensus amino acid sequences as set forth in SEQ ID NO:2, SEQ ID NO:4, or SEQ ID NO:6. Some embodiments relate to immunogenic proteins that have an amino acid sequence that is 91% identical to the full length consensus amino acid sequences as set forth in SEQ ID NO:2, SEQ ID NO:4, or SEQ ID NO:6. Some embodiments relate to immunogenic proteins that have an amino acid sequence that is 92% identical to the full length consensus amino acid sequences as set forth in SEQ ID NO:2, SEQ ID NO:4, or SEQ ID NO:6. Some embodiments relate to immunogenic proteins that have an amino acid sequence that is 93% identical to the full length consensus amino acid sequences as set forth in SEQ ID NO:2, SEQ ID NO:4, or SEQ ID NO:6. Some embodiments relate to immunogenic proteins that have an amino acid sequence that is 94% identical to the full length consensus amino acid sequences as set forth in SEQ ID NO:2, SEQ ID NO:4, or SEQ ID NO:6. Some embodiments relate to immunogenic proteins that have an amino acid sequence that is 95% identical to the full length consensus amino acid sequences as set forth in SEQ ID NO:2, SEQ ID NO:4, or SEQ ID NO:6. Some embodiments relate to immunogenic proteins that have an amino acid sequence that is 96% identical to the full length consensus amino acid sequences as set forth in SEQ ID NO:2, SEQ ID NO:4, or SEQ ID NO:6. Some embodiments relate to immunogenic proteins that have an amino acid sequence that is 97% identical to the full length consensus amino acid sequences as set forth in SEQ ID NO:2, SEQ ID NO:4, or SEQ ID NO:6. Some embodiments relate to immunogenic proteins that have an amino acid sequence that is 98% identical to the full length consensus amino acid sequences as set forth in SEQ ID NO:2, SEQ ID NO:4, or SEQ ID NO:6. Some embodiments relate to immunogenic proteins that have an amino acid sequence that is 99% identical to the full length consensus amino acid sequences as set forth in SEQ ID NO:2, SEQ ID NO:4, or SEQ ID NO:6.

In some embodiments, the protein is free of a leader sequence. In some embodiments, the protein is free of the IgE leader. Fragments of consensus proteins can comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:2, SEQ ID NO:4 or SEQ ID NO:6 can be provided. Immunogenic fragments can comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of SEQ ID NO:2, SEQ ID NO:4 or SEQ ID NO:6. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences homologous to immunogenic fragments of SEQ ID NO:2, SEQ ID NO:4 or SEQ ID NO:6 can be provided. Such immunogenic fragments can comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:2, SEQ ID NO:4 or SEQ ID NO:6. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

Immunogenic fragments of proteins with amino acid sequences identical to immunogenic fragments of SEQ ID NO:2, SEQ ID NO:4 and SEQ ID NO:6 can be provided. Such immunogenic fragments can comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of proteins that are 80%, 85%, 90%, 91%, 92%, 93%, 94%, 95%, 96%, 97%, 98%, 99% identical to the amino acid sequences set forth in SEQ ID NO:2, SEQ ID NO:4 or SEQ ID NO:6. In some embodiments, fragments include a leader sequence, such as for example, an immunoglobulin leader, such as the IgE leader. In some embodiments, fragments are free of a leader sequence. In some embodiments, fragments are free of a leader sequence, such as for example, the IgE leader.

As referred to herein with regard to linking a signal peptide or leader sequence to the N terminus of a protein, the signal peptide/leader sequence replaces the N terminal methionine of a protein which is encoded by the start codon of the nucleic acid sequence than encodes the protein without a signal peptide coding sequences. Thus for example, SEQ ID NO:4 is SEQ ID NO:2 with the signal peptide/leader sequence linked at the N terminal of SEQ ID NO:2, i.e. SEQ ID NO:4 is a protein comprising a signal peptide linked to the N terminus of SEQ ID NO:2. The first residue in SEQ ID NO:2, "Xaa", is typically methionine when no signal peptide is present. However, proteins that comprise signal peptides linked to SEQ ID NO:2, such as SEQ ID NO:4, replace the residue 1 methionine at Xaa with the residue that links the signal peptide to the protein. Accordingly, the N terminal residue of SEQ ID NO:2 can be anything but if it is encoded by an initiation sequence it is methionine. The linkage of the signal peptide/leader sequence at the N terminal of SEQ ID NO:2 typically eliminates the N terminal methionine. As used herein, it is intended that SEQ ID NO:4 comprises SEQ ID NO:2 with a signal peptide/leader sequence linked at the N terminal of SEQ ID NO:2 notwithstanding the elimination of the N terminus Xaa residue of SEQ ID NO:2. Similarly, the coding sequences for SEQ ID NO:4 comprise coding sequences for SEQ ID NO:2 with coding sequences for a signal peptide/leader sequence linked to the 5' end of the coding sequences encoding SEQ ID NO:2. The initiation codon can be the "nnn" in the coding sequences for SEQ ID NO:2 but it is eliminated when the coding sequences for a signal peptide/leader sequence linked to the 5' end of the coding sequences encoding SEQ ID NO:2. As used herein, it is intended that coding sequences for SEQ ID NO:4 comprises coding sequences for SEQ ID NO:2 with coding sequences for a signal peptide/leader sequence linked at the 5' end of the coding sequence of SEQ ID NO:2 where nnn occurs. Thus, for example, it is intended that SEQ ID NO:3 comprises SEQ ID NO:1 with coding sequences for a signal peptide/leader sequence linked at the 5' end of SEQ ID NO:1, in place of the nnn. In some embodiments, the nnn is an initiation codon at the 5' end of SEQ ID NO:1.

b. HBV Surface Antigen

The vaccine can comprise a HBV surface antigen. Provided herein are HBV surface antigens capable of eliciting an immune response in a mammal against one or more HBV serotypes. The surface antigens can comprise surface protein epitopes that make them particularly effective as immunogens against which anti-HBV immune response can be induced. The HBV surface antigen can comprise the full length translation product, a variant thereof, a fragment thereof, or a combination thereof.

Figure 3:
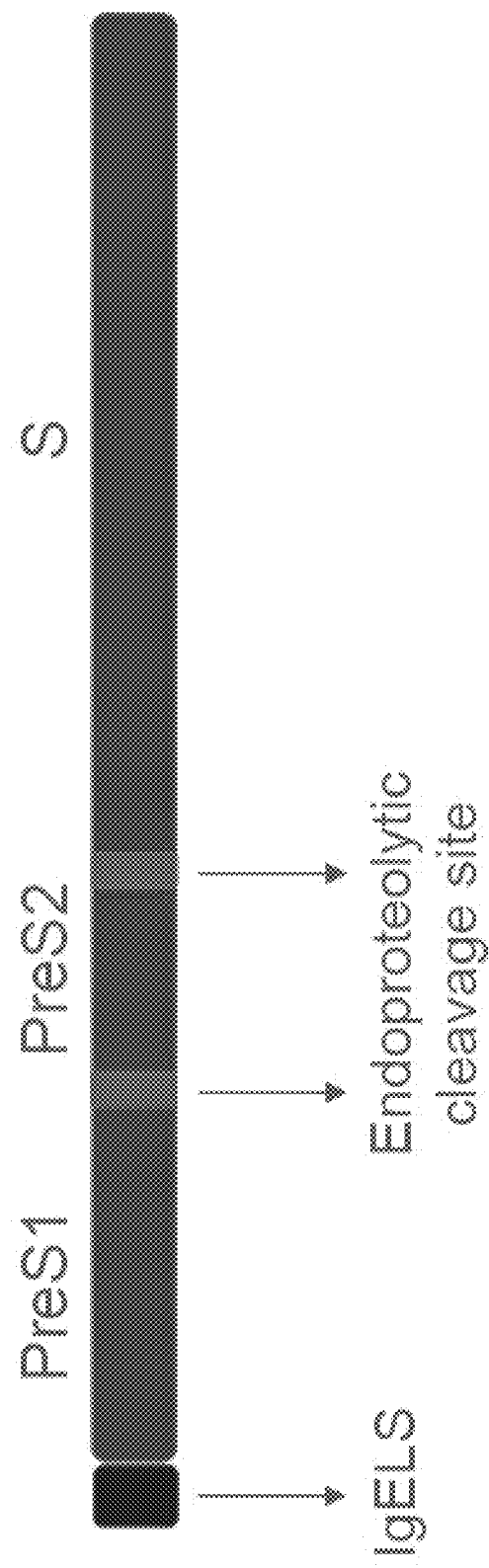
FIG. 3 illustrates IgELS and endoproteolytic cleavage sites in the consensus HBV surface antigen.
Figure 4:
FIG. 4 illustrates the long consensus HBV surface antigen (LHBs) and small consensus HBV surface antigen (SHBs).
Figure 5:
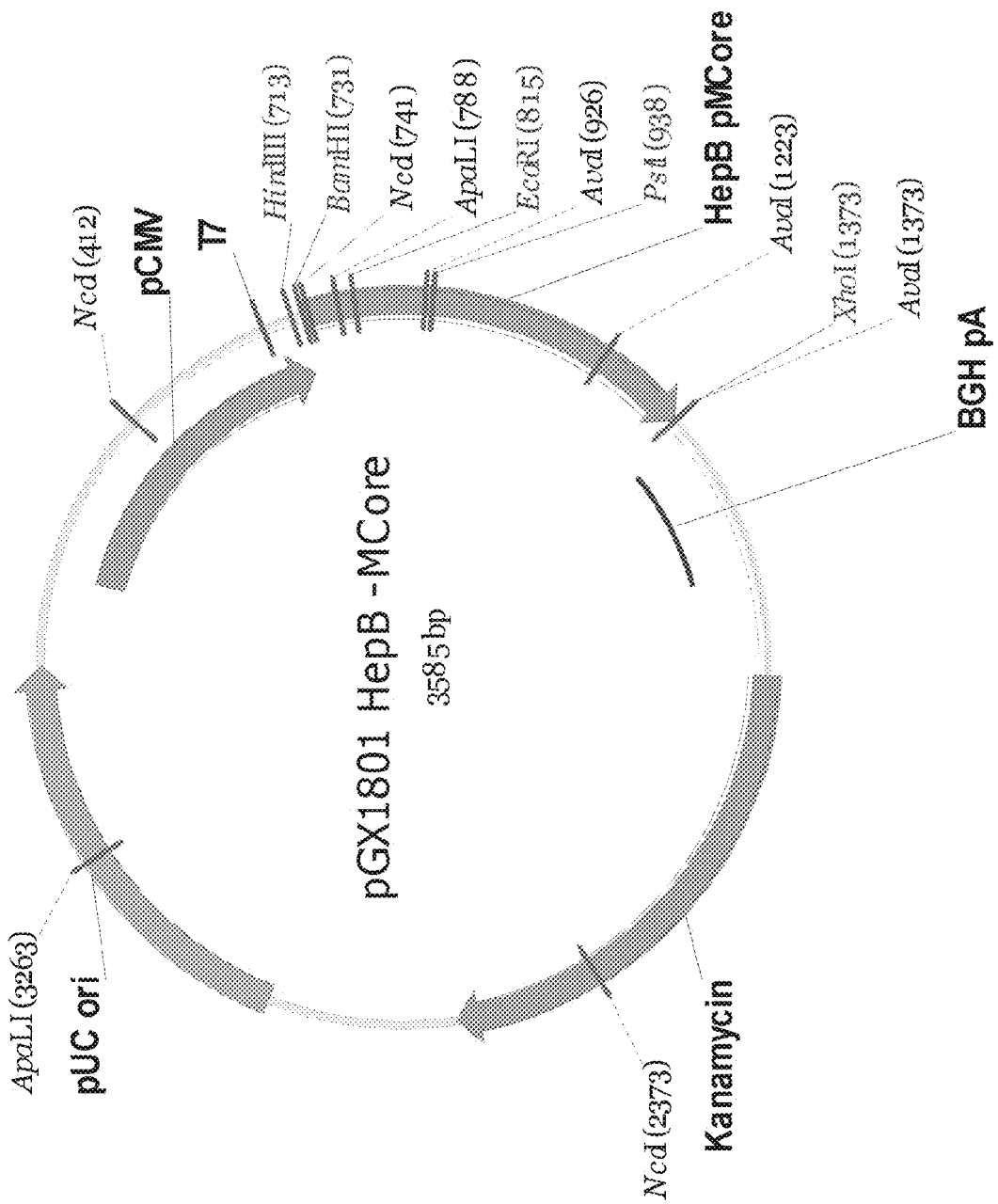
FIG. 5 is a map of the vector pGX1801 HepB-Mcore (SEQ ID NO:17).
Figure 6:
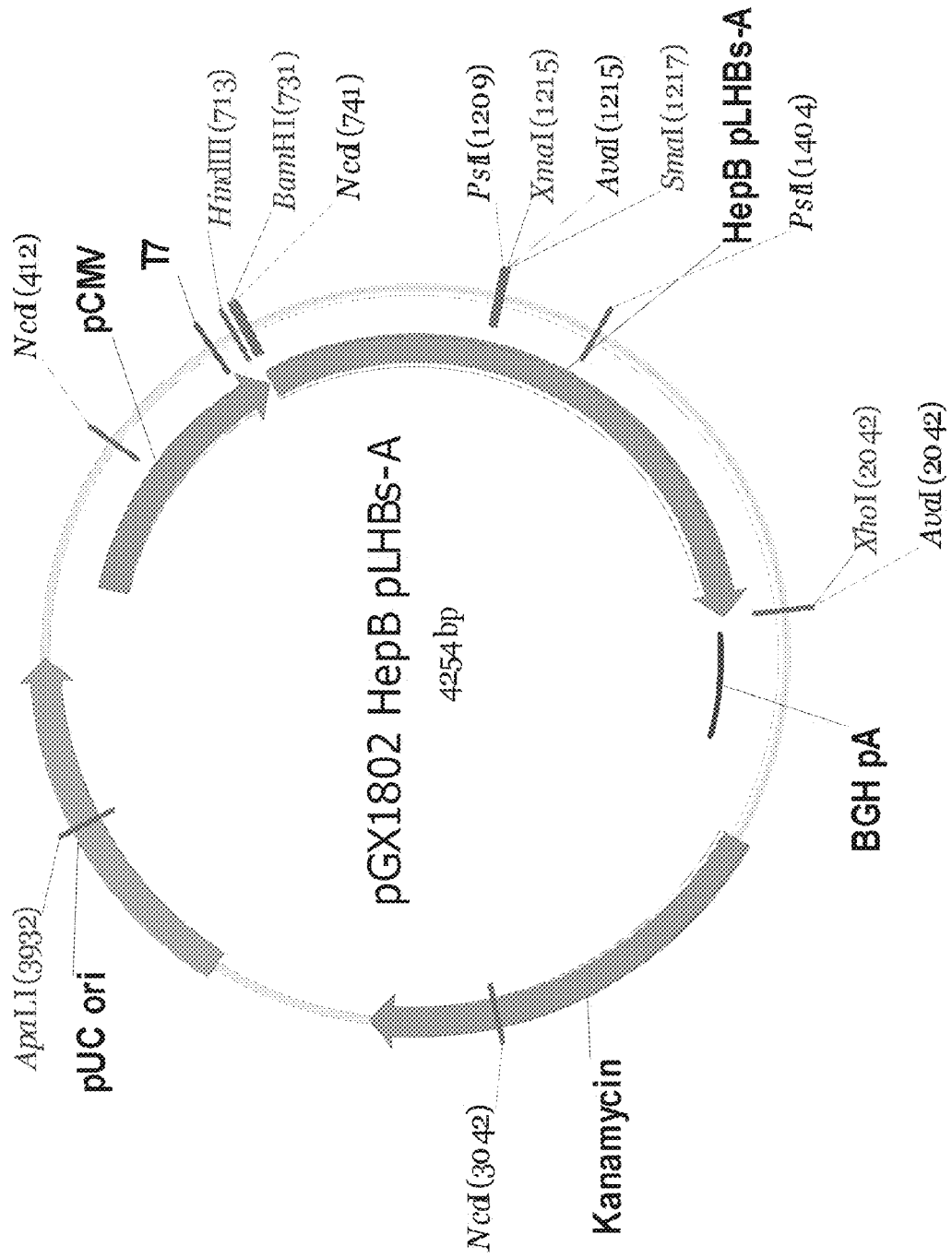
FIG. 6 is a map of the vector pGX1802 HepB pLHBs-A (SEQ ID NO:18).
Figure 7:
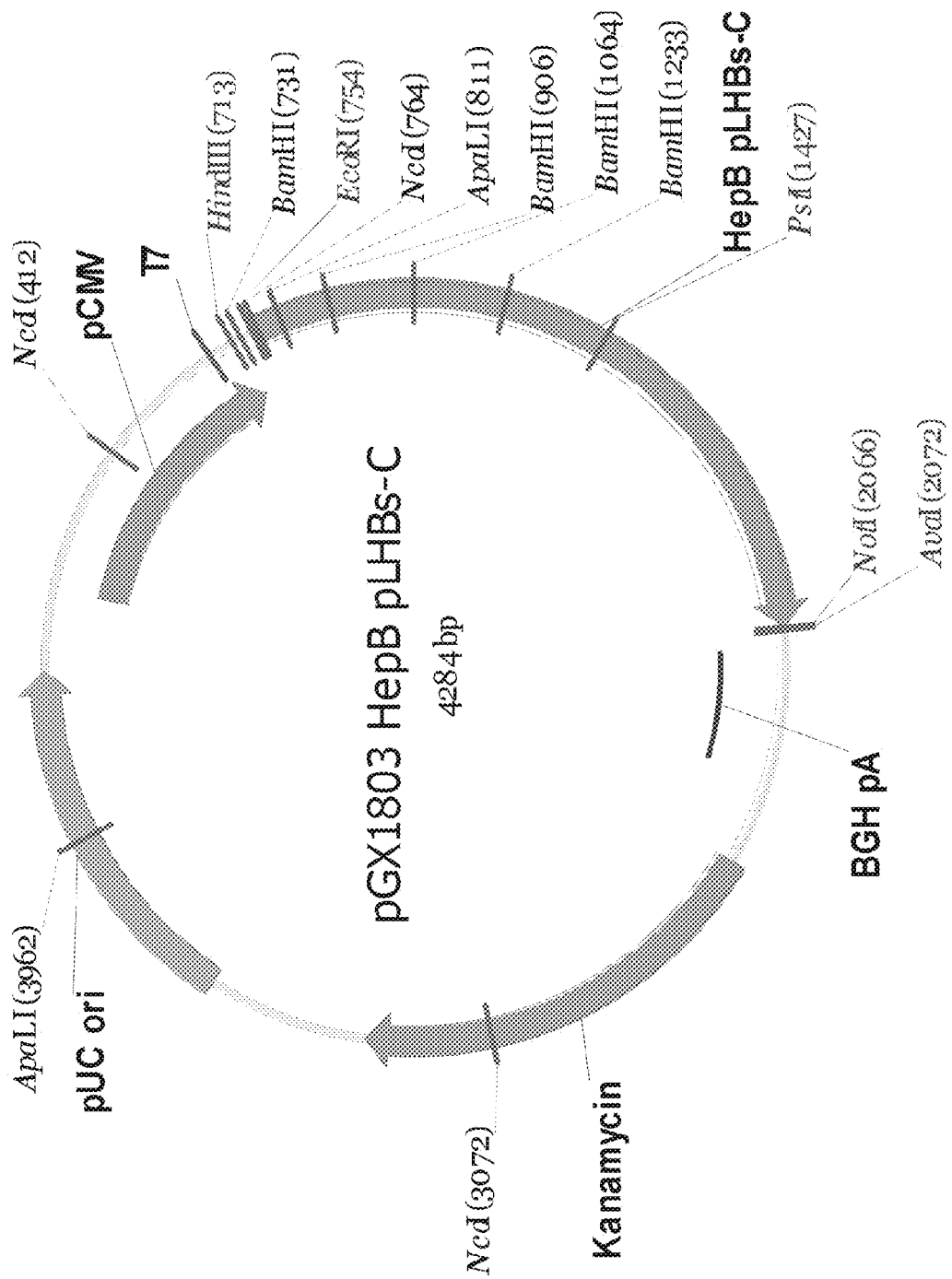
FIG. 7 is a map of the vector pGX1803 HepB pLHBs-C (SEQ ID NO:19).
Figure 8:
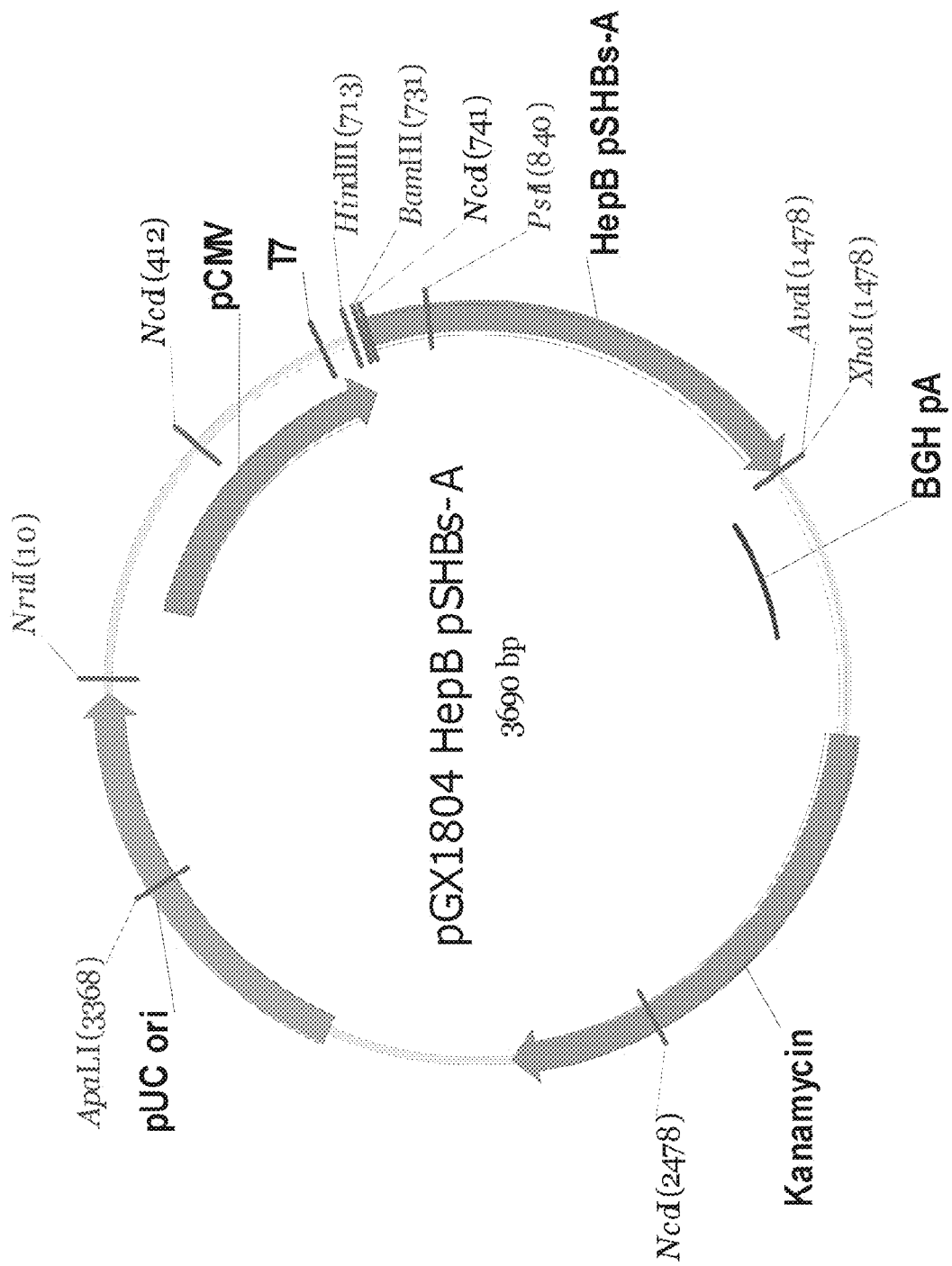
FIG. 8 is a map of the vector pGX1804 HepB pSHBs-A (SEQ ID NO:20).
Figure 9:
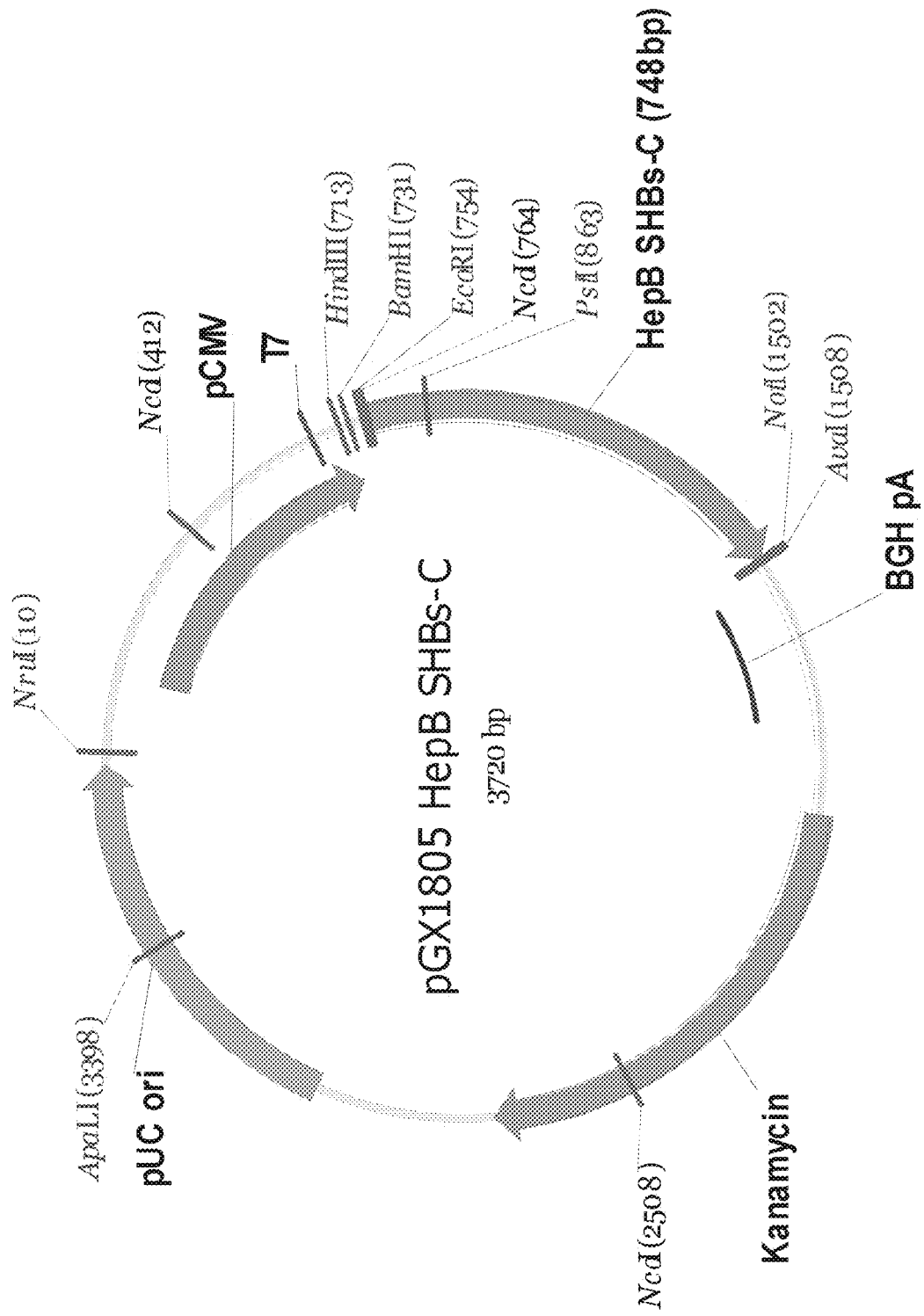
FIG. 9 is a map of the vector pGX1805 HepB SHBs-C (SEQ ID NO:21).
Figure 10:
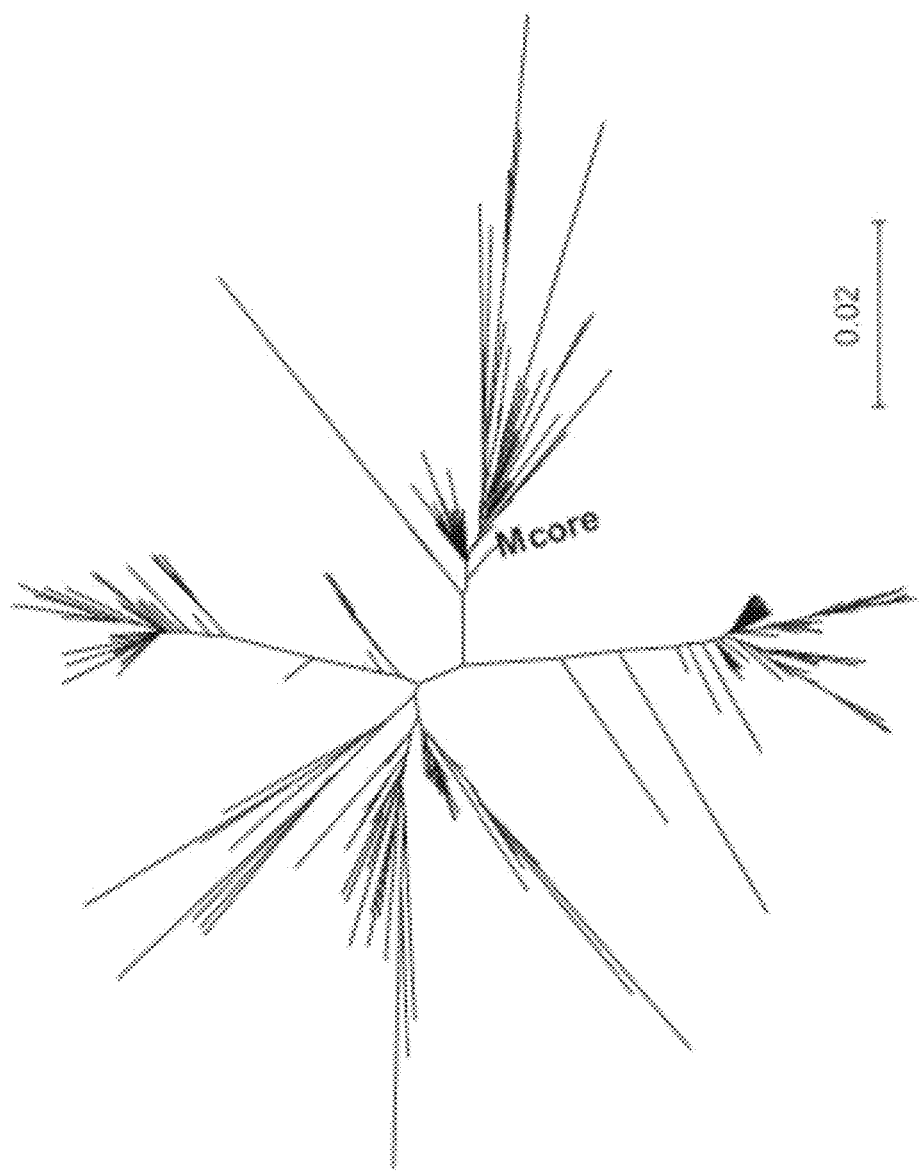
FIG. 10 illustrates a phylogenetic analysis of HBcAg consensus sequence as compared to individual genotypes A, B, C, D, and E.
Figure 11A:
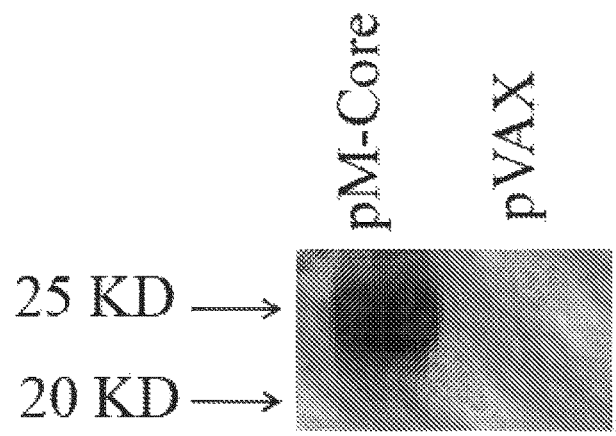
FIGS. 11A and 11B demonstrate results from pM Core expression experiments.
Figure 11B:
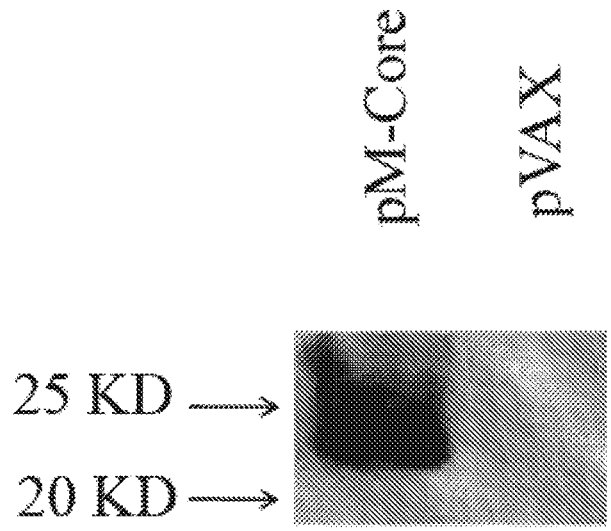
Figure 12:
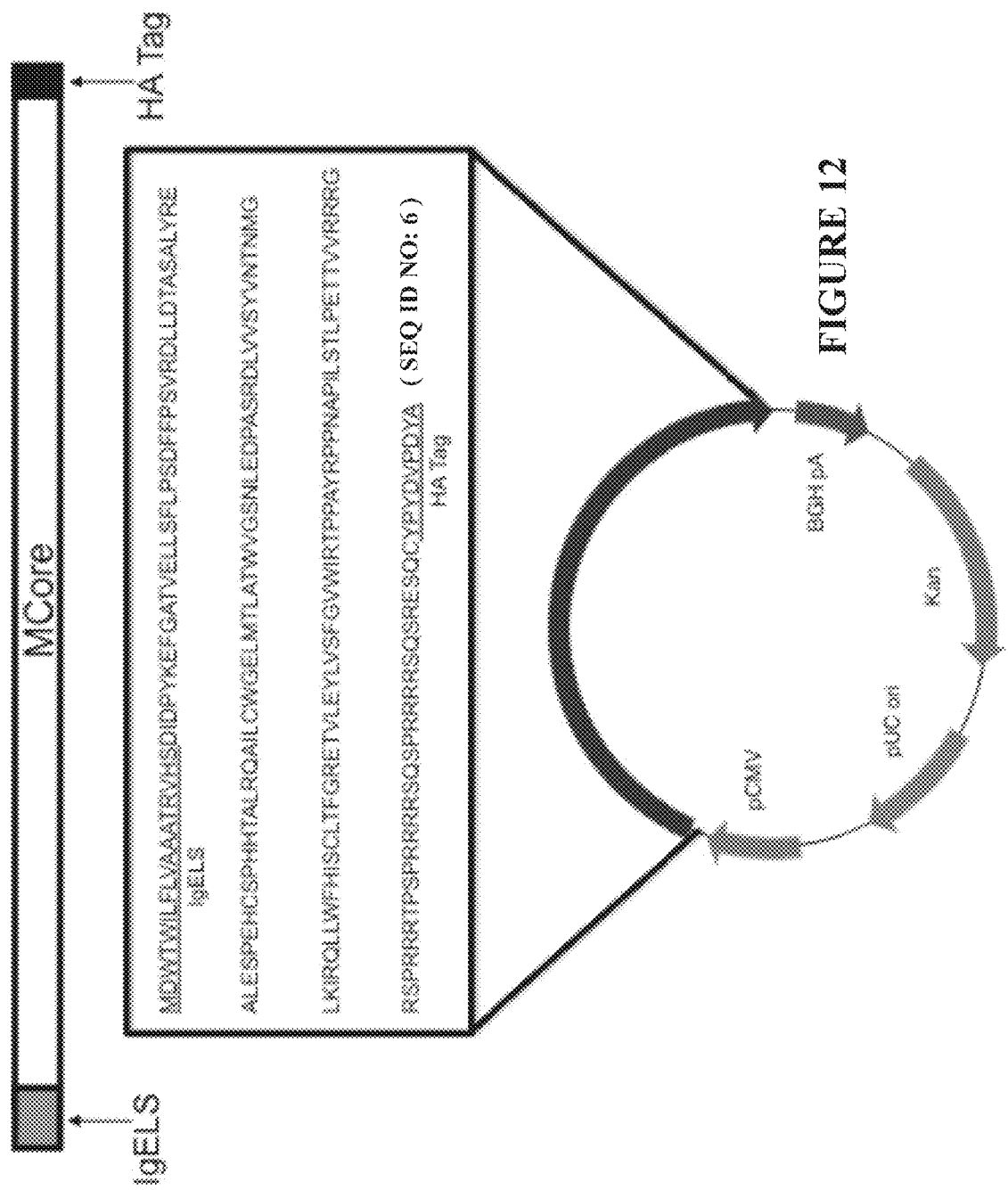
FIG. 12 is a graphic illustrating the plasmid map and sequence of pMCore.
Figure 13:
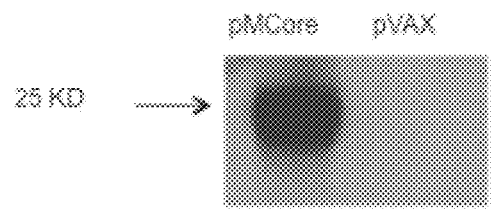
FIG. 13 shows a transcription/translation reaction using pMCore plasmid, in which the resulting MCore protein was immuno-precipitated with anti-HA monoclonal antibody and run on a SDS-PAGE gel.
Figure 14:
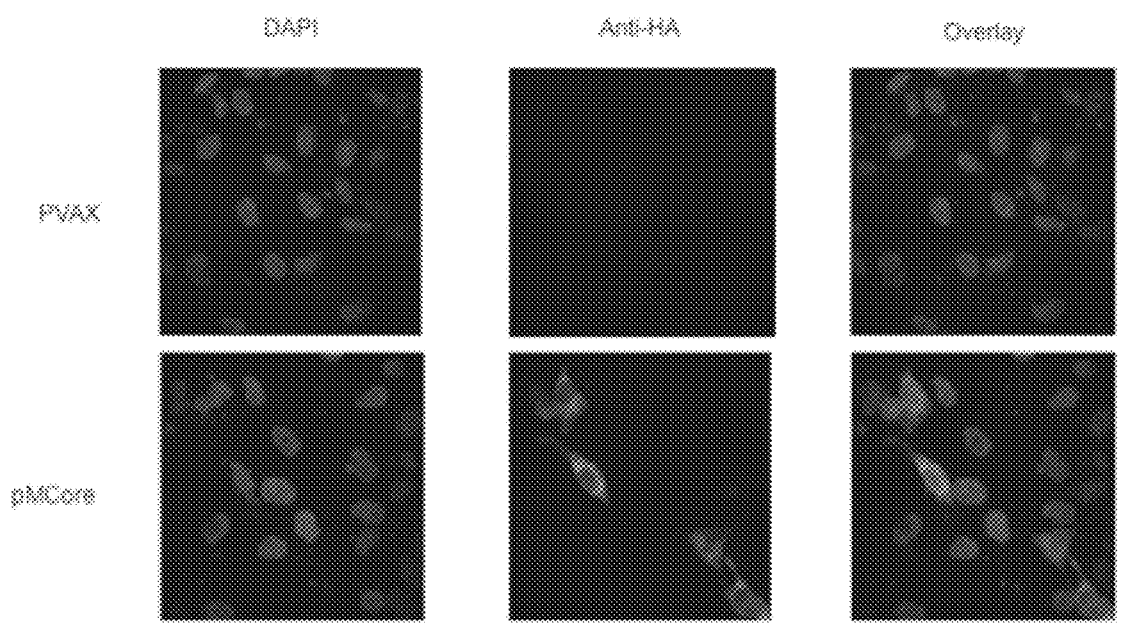
FIG. 14 shows detection of MCore protein in transiently transfected cells using a primary monoclonal HA tag antibody followed by detection with DyLight 594-labeled anti-rabbit secondary antibody. Hoechst stain was also used to fluorescently label cell nuclei. Expression of MCore is mostly localized to the cytoplasm as shown by the staining outside the nucleus.
Figure 15:
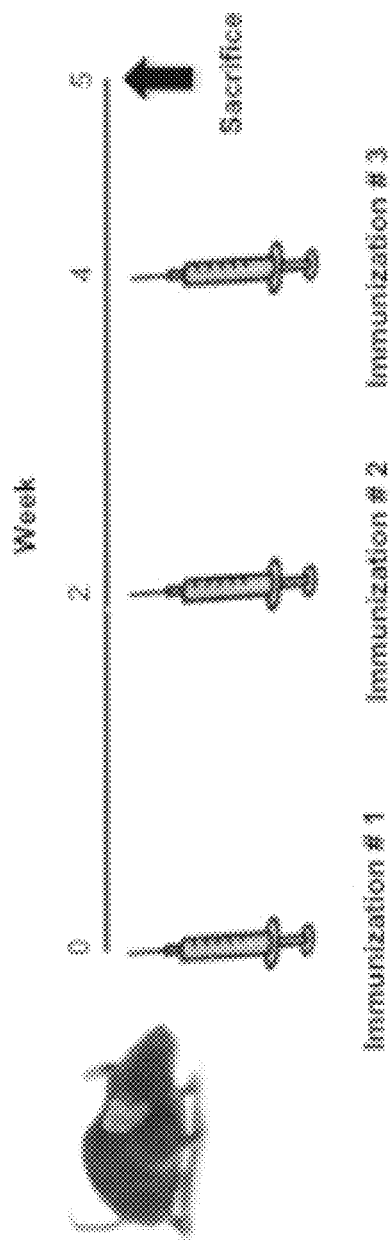
FIG. 15 illustrates an immunization scheme. 4 mice were immunized intramuscularly with 30 μg pMCore.
Figure 16:
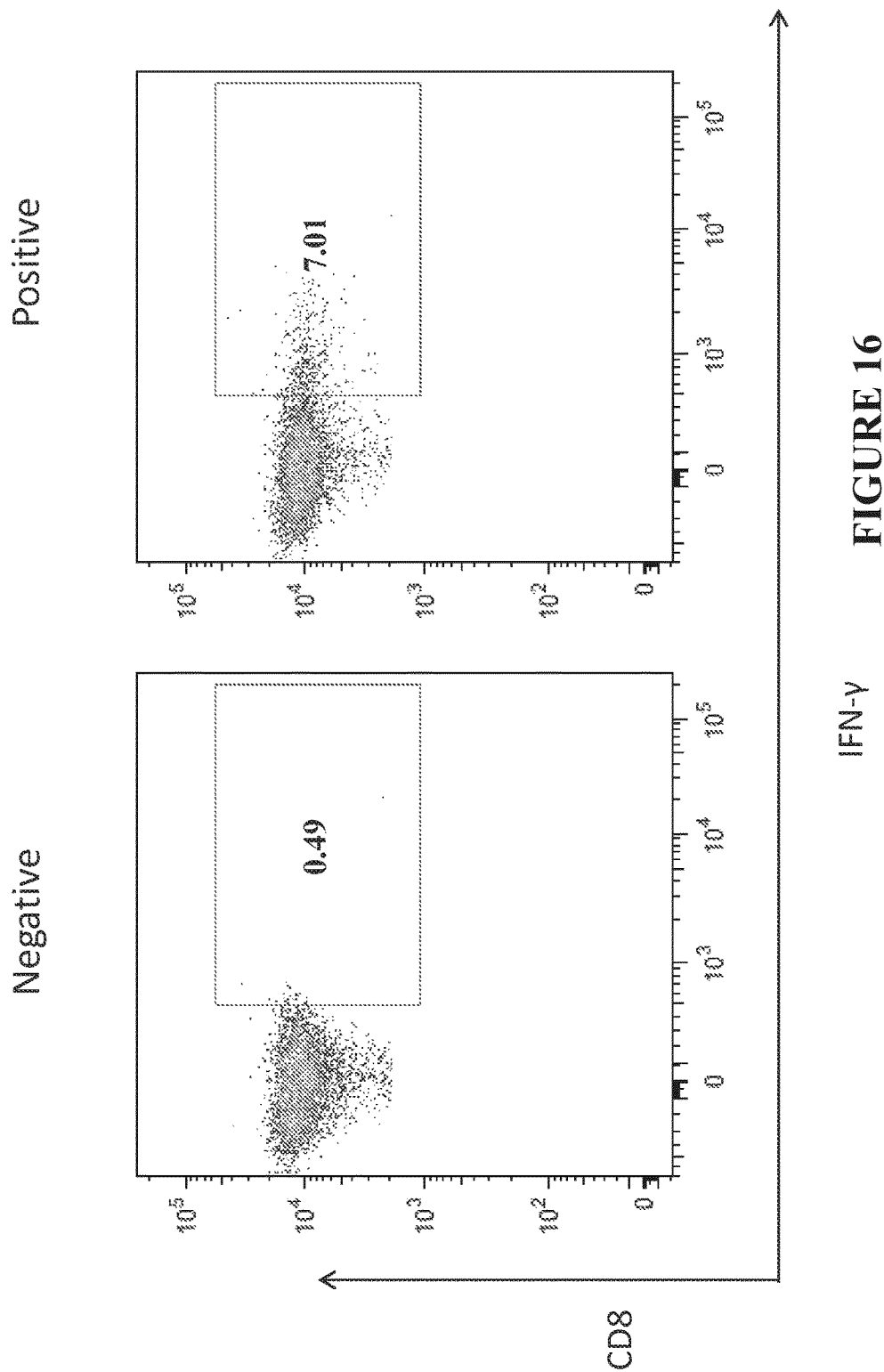
FIG. 16 shows the enhanced magnitude of IFN-γ secretion in CD8+ and CD4+ T Cells from the spleens of Balb/C mice vaccinated with pM-Core.
Figure 17:
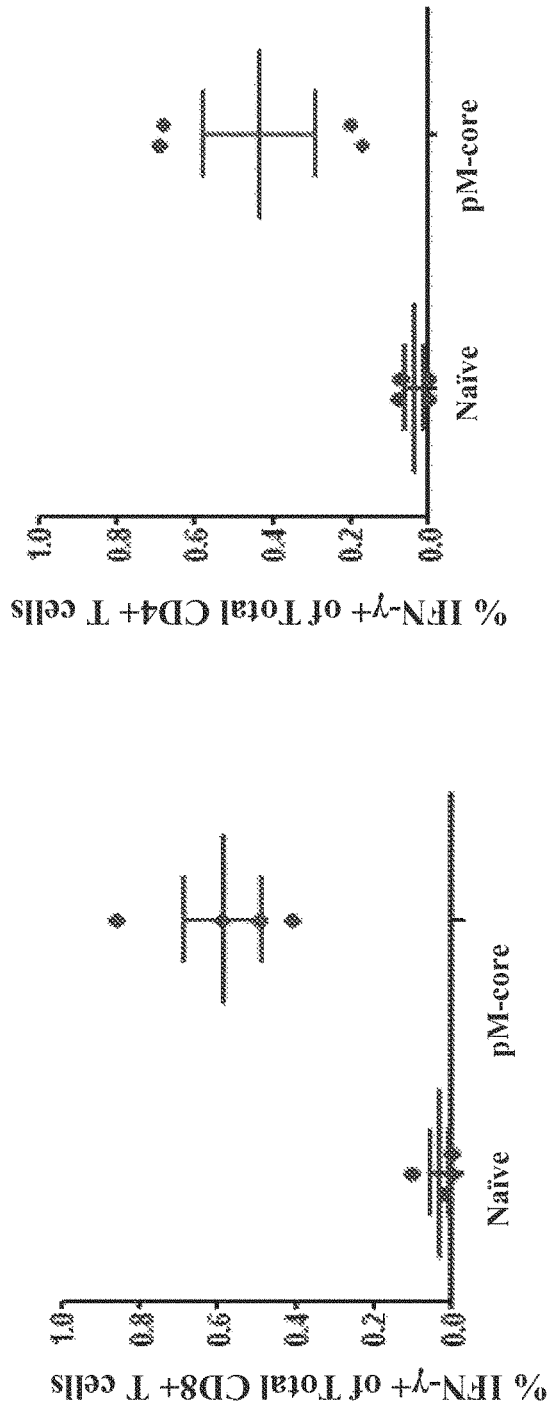
FIG. 17 shows the enhanced magnitude of IFN-γ secretion in CD8+ and CD4+ T Cells from the spleens of Balb/C mice vaccinated with pM-Core.
Figure 18:
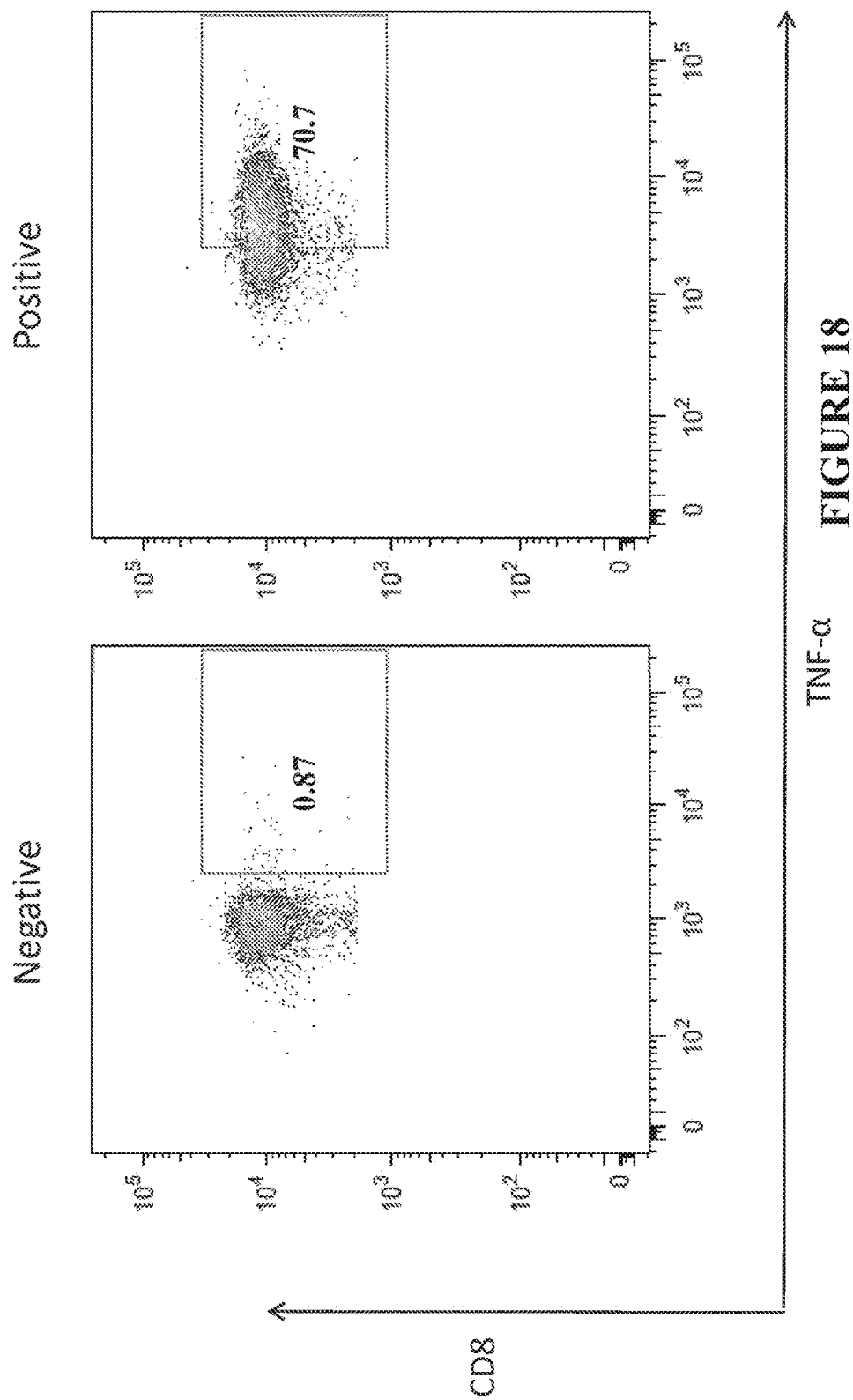
FIG. 18 shows the enhanced magnitude of TNF-α secretion in CD8+ and CD4+ T Cells from the spleens of Balb/C mice vaccinated with pM-Core.
Figure 21:
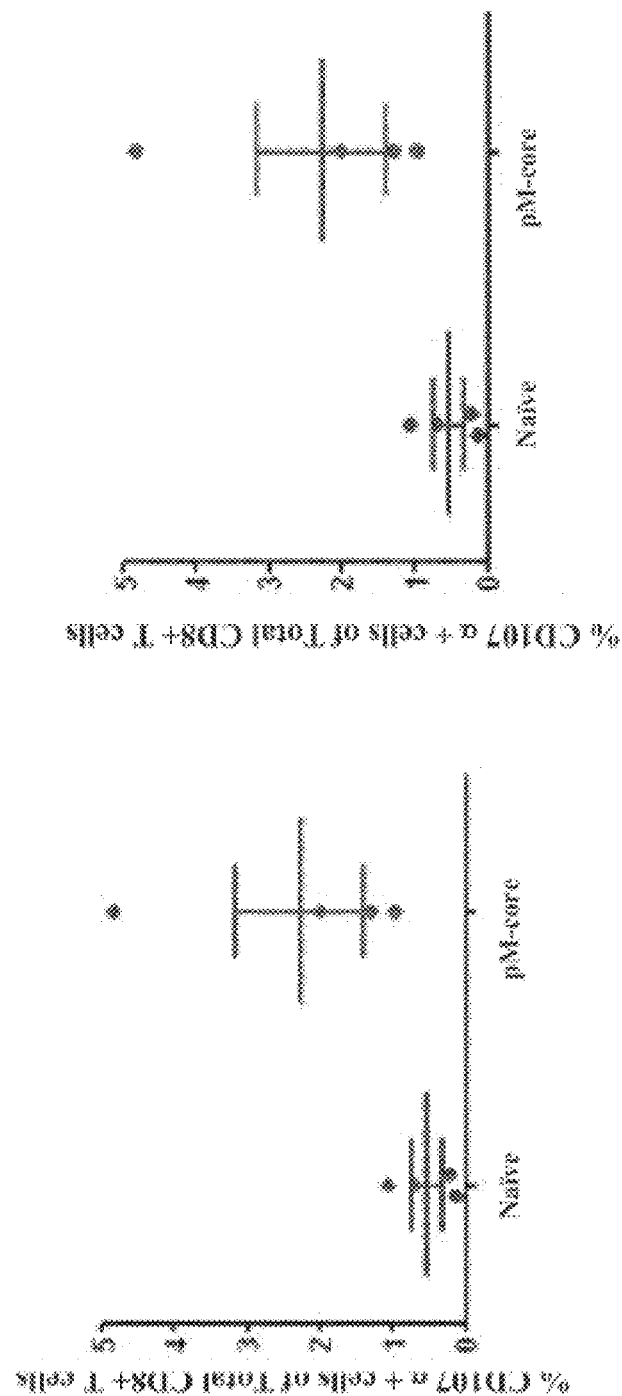
FIG. 21 shows the enhanced magnitude of CD 107a secretion in CD8+ and CD4+ T Cells from the spleens of Balb/C mice vaccinated with pM-Core.

The HBV surface antigen can comprise a consensus protein. Consensus HBV surface antigens were generated from the sequences of surface antigens from primary isolates of either HBV genotype A or C. Particularly, the consensus HBV surface antigens include S protein or the combination of S protein, pre-S2, and pre-S1 (FIGS. 3 and 4). Endoproteolytic cleavage sites were introduced into the consensus HBV surface antigens to provide for proper protein folding and better CTL processing. The codon usage in the consensus HBV surface antigens was modified to reflect the codon bias of human genes. Additionally, regions of very high (e.g., greater than 80 percent) or very low (e.g., less than 30 percent) GC content were avoided, as where cis-acting motifs such as internal TATA-boxes, repetitive sequences, and structured sequences. A Kozak sequence was introduced into the consensus HBV surface antigens to increase translational initiation and an IgE leader sequence was added to increase protein expression.

The nucleic acid sequence encoding the consensus HBV surface antigens are SEQ ID NO:9, SEQ ID NO:11, SEQ ID NO:13, and SEQ ID NO:15. SEQ ID NO:9 encodes a long consensus HBV surface antigen protein derived from genotype A and including S protein, pre-S2, and pre-S1 (LHBs-A). SEQ ID NO:11 encodes a long consensus HBV surface antigen protein derived from genotype C and including S protein, pre-S2, and pre-S1 (LHBs-C). SEQ ID NO:13 encodes a short consensus HBV surface antigen protein derived from genotype A and including S protein (SHBs-A). SEQ ID NO:15 encodes a short consensus HBV surface antigen protein derived from genotype C and including S protein (SHBs-C).

Some embodiments relate to nucleic acid sequences encoding proteins homologous to the consensus HBV surface antigens, immunogenic fragments of the consensus HBV surface antigens, and immunogenic fragments of homologous proteins. Thus, nucleic acid molecules that encode immunogenic proteins that have up to 95% homology to a consensus HBV surface antigen sequence, up to 96% homology to a consensus HBV surface antigen sequence, up to 96% homology to a consensus HBV surface antigen sequence, up to 97% homology to a consensus HBV surface antigen sequence, up to 98% homology to a consensus HBV surface antigen sequence, and up to 99% homology to a consensus HBV surface antigen sequence can be provided. Likewise, nucleic acid sequences encoding the immunogenic fragments set forth herein and the immunogenic fragments of proteins homologous to the HBV surface antigen proteins set forth herein are also provided.

Some embodiments relate to nucleic acid molecules that encode immunogenic proteins that have 95% homology to the nucleic acid HBV surface antigen coding sequences herein. Some embodiments relate to nucleic acid molecules that encode immunogenic proteins that have 96% homology to the nucleic acid HBV surface antigen coding sequences herein. Some embodiments relate to nucleic acid molecules that encode immunogenic proteins that have 97% homology to the nucleic acid HBV surface antigen coding sequences herein. Some embodiments relate to nucleic acid molecules that encode immunogenic proteins that have 98% homology to the nucleic acid HBV surface antigen coding sequences herein. Some embodiments relate to nucleic acid molecules that encode immunogenic proteins that have 99% homology to the nucleic acid HBV surface antigen coding sequences herein. In some embodiments, the nucleic acid molecules with coding sequences disclosed herein that are homologous to a coding sequence of a consensus HBV surface antigen protein disclosed herein include sequences encoding an IgE leader sequence linked to the 5' end of the coding sequence encoding the homologous protein sequences disclosed herein.

Some embodiments relate to nucleic acid sequences encoding proteins with a particular percent identity to the full length HBV surface antigen consensus protein, immunogenic fragment of the HBV surface antigen consensus protein, and immunogenic fragments of HBV surface antigen consensus proteins. Such nucleic acid molecules that encode immunogenic proteins that have up to 80% identity to a full length HBV surface antigen consensus sequence, up to 85% identity to a full length HBV surface antigen consensus sequence, up to 90% identity to a full length HBV surface antigen consensus sequence, up to 91% identity to a full length HBV surface antigen consensus sequence, up to 92% identity to a full length HBV surface antigen consensus sequence, up to 93% identity to a full length HBV surface antigen consensus sequence, up to 94% identity to a full length HBV surface antigen consensus sequence, up to 95% identity to a full length HBV surface antigen consensus sequence, up to 96% identity to a full length HBV surface antigen consensus sequence, up to 97% identity to a full length HBV surface antigen consensus sequence, up to 98% identity to a full length HBV surface antigen consensus sequence, up to 99% identity to a full length HBV surface antigen consensus sequence can be provided. Likewise, nucleic acid sequences encoding the immunogenic fragments set forth herein and the immunogenic fragments of proteins with similar percent identities as indicated above to the HBV surface antigen proteins set forth herein are also provided.

Some embodiments relate to nucleic acid molecules that encode immunogenic proteins that have 80% identity to the full length nucleic acid HBV surface antigen coding sequences herein. Some embodiments relate to nucleic acid molecules that encode immunogenic proteins that have 83% identity to the full length nucleic acid HBV surface antigen coding sequences herein. Some embodiments relate to nucleic acid molecules that encode immunogenic proteins that have 85% identity to the full length nucleic acid HBV surface antigen coding sequences herein. Some embodiments relate to nucleic acid molecules that encode immunogenic proteins that have 90% identity to the full length nucleic acid HBV surface antigen coding sequences herein. Some embodiments relate to nucleic acid molecules that encode immunogenic proteins that have 91% identity to the full length nucleic acid HBV surface antigen coding sequences herein. Some embodiments relate to nucleic acid molecules that encode immunogenic proteins that have 92% identity to the full length nucleic acid HBV surface antigen coding sequences herein. Some embodiments relate to nucleic acid molecules that encode immunogenic proteins that have 93% identity to the full length nucleic acid HBV surface antigen coding sequences herein. Some embodiments relate to nucleic acid molecules that encode immunogenic proteins that have 94% identity to the full length nucleic acid HBV surface antigen coding sequences herein. Some embodiments relate to nucleic acid molecules that encode immunogenic proteins that have 95% identity to the full length nucleic acid HBV surface antigen coding sequences herein. Some embodiments relate to nucleic acid molecules that encode immunogenic proteins that have 96% identity to the full length nucleic acid HBV surface antigen coding sequences herein. Some embodiments relate to nucleic acid molecules that encode immunogenic proteins that have 97% identity to the full length nucleic acid HBV surface antigen coding sequences herein. Some embodiments relate to nucleic acid molecules that encode immunogenic proteins that have 98% identity to the full length nucleic acid HBV surface antigen coding sequences herein. Some embodiments relate to nucleic acid molecules that encode immunogenic proteins that have 99% identity to the full length nucleic acid HBV surface antigen coding sequences herein. In some embodiments, the nucleic acid molecules with coding HBV surface antigen sequences disclosed herein that are homologous to a coding sequence of a consensus HBV surface antigen protein disclosed herein include sequences encoding an IgE leader sequence linked to the 5' end of the coding sequence encoding the homologous protein sequences disclosed herein.

In some embodiments, the nucleic acid sequence is free of coding sequence that encodes a leader sequence. In some embodiments, the nucleic acid sequence is free of coding sequence that encodes the IgE leader.

Some embodiments relate to fragments of SEQ ID NO:9, SEQ ID NO: 11, SEQ ID NO:13, and SEQ ID NO:15. Fragments can be at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of SEQ ID NO:9, SEQ ID NO:11, SEQ ID NO:13, or SEQ ID NO:15. Fragments can be at least 95%, at least 96%, at least 97% at least 98% or at least 99% homologous to fragments of SEQ ID NO:9, SEQ ID NO:11, SEQ ID NO:13, or SEQ ID NO:15. Fragments can be at least 80%, at least 85%, at least 90% at least 91%, at least 92%, at least 93%, at least 94%, at least 95%, at least 96%, at least 97%, at least 98% or at least 99% identity to fragments of SEQ ID NO:9, SEQ ID NO:11, SEQ ID NO: 13 or SEQ ID NO:15. In some embodiments, fragments include sequences that encode a leader sequence, such as for example, an immunoglobulin leader, such as the IgE leader. In some embodiments, fragments are free of coding sequences that encode a leader sequence. In some embodiments, fragments are free of coding sequences that encode a leader sequence, such as the IgE leader.

Furthermore, the amino acid sequences of the consensus HBV surface antigens, LHBs-A, LHBs-C, SHBs-A, and SHBs-C, are SEQ ID NO:10, SEQ ID NO:12, SEQ ID NO:14, and SEQ ID NO:16, respectively.

Proteins can be homologous to SEQ ID NO:10, SEQ ID NO: 12, SEQ ID NO:14, or SEQ ID NO:16. Some embodiments relate to immunogenic proteins that have 95% homology to the consensus protein sequences herein. Some embodiments relate to immunogenic proteins that have 96% homology to the consensus protein sequences herein. Some embodiments relate to immunogenic proteins that have 97% homology to the consensus protein sequences herein. Some embodiments relate to immunogenic proteins that have 98% homology to the consensus protein sequences herein. Some embodiments relate to immunogenic proteins that have 99% homology to the consensus protein sequences herein.

Some embodiments relate to proteins that are identical to SEQ ID NO:10, SEQ ID NO:12, SEQ ID NO: 14 or SEQ ID NO:16. Some embodiments relate to immunogenic proteins that have an amino acid sequence that is 80% identical to the full length consensus amino acid sequences as set forth in SEQ ID NO:10, SEQ ID NO:12, SEQ ID NO: 14 or SEQ ID NO:16. Some embodiments relate to immunogenic proteins that have an amino acid sequence that is 85% identical to the full length consensus amino acid sequences as set forth in SEQ ID NO:10, SEQ ID NO:12, SEQ ID NO: 14 or SEQ ID NO:16. Some embodiments relate to immunogenic proteins that have an amino acid sequence that is 90% identical to the full length consensus amino acid sequences as set forth in SEQ ID NO:10, SEQ ID NO:12, SEQ ID NO: 14 or SEQ ID NO:16. Some embodiments relate to immunogenic proteins that have an amino acid sequence that is 91% identical to the full length consensus amino acid sequences as set forth in SEQ ID NO:10, SEQ ID NO:12, SEQ ID NO: 14 or SEQ ID NO:16. Some embodiments relate to immunogenic proteins that have an amino acid sequence that is 92% identical to the full length consensus amino acid sequences as set forth in SEQ ID NO:10, SEQ ID NO:12, SEQ ID NO: 14 or SEQ ID NO:16. Some embodiments relate to immunogenic proteins that have an amino acid sequence that is 93% identical to the full length consensus amino acid sequences as set forth in SEQ ID NO:10, SEQ ID NO:12, SEQ ID NO: 14 or SEQ ID NO:16. Some embodiments relate to immunogenic proteins that have an amino acid sequence that is 94% identical to the full length consensus amino acid sequences as set forth in SEQ ID NO:10, SEQ ID NO:12, SEQ ID NO: 14 or SEQ ID NO:16. Some embodiments relate to immunogenic proteins that have an amino acid sequence that is 95% identical to the full length consensus amino acid sequences as set forth in SEQ ID NO:10, SEQ ID NO:12, SEQ ID NO: 14 or SEQ ID NO:16. Some embodiments relate to immunogenic proteins that have an amino acid sequence that is 96% identical to the full length consensus amino acid sequences as set forth in SEQ ID NO:10, SEQ ID NO:12, SEQ ID NO: 14 or SEQ ID NO:16. Some embodiments relate to immunogenic proteins that have an amino acid sequence that is 97% identical to the full length consensus amino acid sequences as set forth in SEQ ID NO:10, SEQ ID NO:12, SEQ ID NO: 14 or SEQ ID NO:16. Some embodiments relate to immunogenic proteins that have an amino acid sequence that is 98% identical to the full length consensus amino acid sequences as set forth in SEQ ID NO:10, SEQ ID NO:12, SEQ ID NO: 14 or SEQ ID NO:16. Some embodiments relate to immunogenic proteins that have an amino acid sequence that is 99% identical to the full length consensus amino acid sequences as set forth in SEQ ID NO:10, SEQ ID NO:12, SEQ ID NO: 14 or SEQ ID NO:16.

Fragments of consensus proteins can comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of a consensus protein. Immunogenic fragments of SEQ ID NO:10, SEQ ID NO:12, SEQ ID NO:14, and SEQ ID NO:16 can be provided. Immunogenic fragments can comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of SEQ ID NO:10, SEQ ID NO:12, SEQ ID NO:14, or SEQ ID NO:16.

Immunogenic fragments of proteins with amino acid sequences homologous to immunogenic fragments of SEQ ID NO:10, SEQ ID NO:12, SEQ ID NO:14, or SEQ ID NO:16 can be provided. Such immunogenic fragments can comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:10, SEQ ID NO:12, SEQ ID NO:14, or SEQ ID NO:16.

Immunogenic fragments of proteins with amino acid sequences homologous to immunogenic fragments of SEQ ID NO:10, SEQ ID NO:12, SEQ ID NO:14, or SEQ ID NO:16 can be provided. Such immunogenic fragments can comprise at least 10%, at least 15%, at least 20%, at least 25%, at least 30%, at least 35%, at least 40%, at least 45%, at least 50% or at least 55% at least 60%, at least 65%, at least 70%, at least 75%, at least 80%, at least 85%, at least 90%, at least 95%, at least 96%, at least 97%, at least 98% or at least 99% of proteins that are 95% homologous to SEQ ID NO:10, SEQ ID NO:12, SEQ ID NO:14, or SEQ ID NO:16. Some embodiments relate to immunogenic fragments that have 96% homology to the immunogenic fragments of consensus protein sequences herein. Some embodiments relate to immunogenic fragments that have 97% homology to the immunogenic fragments of consensus protein sequences herein. Some embodiments relate to immunogenic fragments that have 98% homology to the immunogenic fragments of consensus protein sequences herein. Some embodiments relate to immunogenic fragments that have 99% homology to the immunogenic fragments of consensus protein sequences herein.

c. Combination of HBV Core and Surface Antigens

The vaccine can comprise a combination of the HBV core and surface antigens as described above. This combination of HBV antigens is capable of eliciting an immune response in a mammal against one or more HBV serotypes. The vaccine can be designed or tailored to have a particular combination of HBV antigens, which in turn provides the ability to control the level or strength of an immune response in the mammal.

The combinations can comprise one or more nucleic acids encoding (1) HBV-M-Core, LHBs-A, SHBs-A, LHBs-C, and SHBs-C; (2) HBV-M-Core, LHBs-A, SHBs-A, and LHBs-C; (3) HBV-M-Core, LHBs-A, and SHBs-A; (4) HBV-M-Core and LHBs-A; (5) HBV-M-Core, SHBs-A, LHBs-C, and SHBs-C; (6) HBV-M-Core, LHBs-C, and SHBs-C; (7) HBV-M-Core and SHBs-C; (8) HBV-M-Core, LHBs-A, LHBs-C, and SHBs-C; (9) HBV-M-core, LHBs-A, and SHBs-C; (10) HBV-M-Core and SHBs-C; (11) HBV-M-Core, LHBs-A, SHBs-A, and SHBs-C; (12) HBV-M-Core, LHBs-A, and SHBs-C; (13) HBV-M-Core, SHBs-A, and SHBs-C; (14) LHBs-A, SHBs-A, LHBs-C, and SHbs-C; (15) LHBs-A, SHBs-A, and LHBs-C; (16) LHBs-A and SHBs-A; (17) SHBs-A, LHBs-C, and SHBs-C; (18) LHBs-C and SHBs-C; (19) LHBs-A, LHBs-C, and SHBs-C; (20) LHBs-A and SHBs-C; (21) LHBs-A, SHBs-A, and SHBs-C; (22) LHBs-A and SHBs-C; (23) SHBs-A and SHBs-C; (24) HBV-M-Core and SHBs-A; (25) HBV-M-Core, LHBs-A and LHBs-C; or (26) LHBs-A and LHBs-C.

An exemplary embodiment relates to a vaccine including one or more nucleic acids encoding HBV-M-Core, LHBs-A, and LHBs-C. Another exemplary embodiment relates to vaccine including one or more nucleic acids encoding HBV-M-Core, SHBs-A, and SHBs-C. Yet another exemplary embodiment relates to a vaccine including one or more nucleic acids encoding HBV-M-Core, LHBs-A, and LHBs-C, and adjuvant such as IL-12.

The combinational vaccine also comprises one or more consensus HBV core protein and/or HBV surface antigen protein in the form of one or more protein subunits, one or more killed viral particles comprising one or more consensus HBV core protein and/or consensus HBV surface antigen protein, or one or more attenuated viral particles comprising one or more consensus HBV core protein and/or HBV surface antigen protein. The attenuated vaccine can be attenuated live vaccines, killed vaccines and vaccines that use recombinant vectors to deliver foreign genes that encode one or more consensus HBV core protein and/or HBV surface antigen protein, and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

d. Vaccine Constructs and Plasmids

The vaccine can comprise nucleic acid constructs or plasmids that encode the HBV core proteins, the HBV surface antigens, and combinations of the HBV core proteins/surface antigens. Provided herein are genetic constructs that can comprise a nucleic acid sequence that encodes the HBV core antigen disclosed herein including consensus protein sequences, sequences homologous to consensus protein sequences, fragments of consensus protein sequences and sequences homologous to fragments of consensus protein sequences. Additionally, provided herein are genetic constructs that can comprise a nucleic acid sequence that encodes the HBV surface antigen disclosed herein including consensus protein sequences, sequences homologous to consensus protein sequences, fragments of consensus protein sequences and sequences homologous to fragments of consensus protein sequences. The genetic construct can be present in the cell as a functioning extrachromosomal molecule. The genetic construct can be a linear minichromosome including centromere, telomeres or plasmids or cosmids.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the coding sequences of the nucleic acid. The regulatory elements can be a promoter, an enhancer an initiation codon, a stop codon, or a polyadenylation signal.

The nucleic acid sequences can make up a genetic construct that can be a vector. The vector can be capable of expressing an antigen in the cell of a mammal in a quantity effective to elicit an immune response in the mammal. The vector can be recombinant. The vector can comprise heterologous nucleic acid encoding the antigen. The vector can be a plasmid. The vector can be useful for transfecting cells with nucleic acid encoding an antigen, which the transformed host cell is cultured and maintained under conditions wherein expression of the antigen takes place.

Coding sequences can be optimized for stability and high levels of expression. In some instances, codons are selected to reduce secondary structure formation of the RNA such as that formed due to intramolecular bonding.

The vector can comprise heterologous nucleic acid encoding an antigen and can further comprise an initiation codon, which can be upstream of the antigen coding sequence, and a stop codon, which can be downstream of the antigen coding sequence. The initiation and termination codon can be in frame with the antigen coding sequence. The vector can also comprise a promoter that is operably linked to the antigen coding sequence. The promoter operably linked to the antigen coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the HBV core protein coding sequence. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the consensus HBV core protein coding sequence or the consensus HBV surface antigen protein coding sequence. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

The vector can also comprise a mammalian origin of replication in order to maintain the vector extrachromosomally and produce multiple copies of the vector in a cell. The vector can be pVAX1, pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

Based upon the sequence of pVAX1 available from Invitrogen, the following mutations were found in the sequence of pVAX1 that was used as the backbone for plasmids 1-6 set forth herein:

C>G241 in CMV promoter

C>T 1942 backbone, downstream of the bovine growth hormone polyadenylation signal (bGHpolyA)

A>−2876 backbone, downstream of the Kanamycin gene

C>T3277 in pUC origin of replication (Ori) high copy number mutation (see Nucleic Acid Research 1985)

G>C 3753 in very end of pUC Ori upstream of RNASeH site

Base pairs 2, 3 and 4 are changed from ACT to CTG in backbone, upstream of CMV promoter.

The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The consensus HBV coding sequence can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which maybe used for protein production in mammalian cells such as Chinese hamster ovary (CHO) cells. The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference.

In some embodiments the vector can comprise the nucleic acid sequence of SEQ ID NO:17, SEQ ID NO:18, SEQ ID NO:19, SEQ ID NO:20, or SEQ ID NO:21. SEQ ID NO:17 encodes a consensus HBV core protein and SEQ ID NOS:18-21 encodes a consensus HBV surface antigen. The vector maps of SEQ ID NOS:17-21 are shown in FIGS. 5-9, respectively.

e. Pharmaceutical Compositions of the Vaccine

The vaccine can be in the form of a pharmaceutical composition. The pharmaceutical composition can comprise the vaccine.

The pharmaceutical compositions can comprise about 5 nanograms to about 10 mg of the vaccine DNA. In some embodiments, pharmaceutical compositions according to the present invention comprise about 25 nanogram to about 5 mg of vaccine DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. In some embodiments, the pharmaceutical compositions comprise about 10 microgram to about 100 micrograms of DNA. In some embodiments, the pharmaceutical compositions comprise about 20 micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about 35 nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of DNA of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms of DNA of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of DNA of the vaccine.

In other embodiments, the pharmaceutical composition can comprise up to and including 15, 20, 25, 30, 35, 40, 45, 50, 55, 60, 65, 70, 75, 80, 85, 90, 95 or 100 nanograms of DNA of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 micrograms of DNA of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of DNA of the vaccine.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector vaccines can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in alternative plasmid or are delivered as proteins in combination with the plasmid above in the vaccine. The adjuvant can be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof. In an exemplary embodiment, the adjuvant is IL-12.

Other genes which can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

f. Methods of Vaccine Delivery

Provided herein is a method for delivering the pharmaceutical formulations for providing genetic constructs and proteins of the HBV core protein and/or HBV surface antigen which comprise epitopes that make them particular effective immunogens against which an immune response to HBV viral infections can be induced. The method of delivering the vaccine, or vaccination, can be provided to induce a therapeutic and/or prophylactic immune response. The vaccination process can generate in the mammal an immune response against a plurality of HBV genotypes. The vaccine can be delivered to an individual to modulate the activity of the mammal's immune system and enhance the immune response. The delivery of the vaccine can be the transfection of the HA antigen as a nucleic acid molecule that is expressed in the cell and delivered to the surface of the cell upon which the immune system recognizes and induces a cellular, humoral, or cellular and humoral response. The delivery of the vaccine can be use to induce or elicit an immune response in mammals against a plurality of HBV viruses by administering to the mammals the vaccine as discussed herein.

Upon delivery of the vaccine to the mammal, and thereupon the vector into the cells of the mammal, the transfected cells will express and secrete consensus HBV core protein and consensus HBV surface antigen. These secreted proteins, or synthetic antigens, will be recognized as foreign by the immune system, which will mount an immune response that can include: antibodies made against the antigens, and T-cell response specifically against the antigen. In some examples, a mammal vaccinated with the vaccines discussed herein will have a primed immune system and when challenged with an HBV viral strain, the primed immune system will allow for rapid clearing of subsequent HBV viruses, whether through the humoral, cellular, or both. The vaccine can be delivered to an individual to modulate the activity of the individual's immune system thereby enhancing the immune response.

Methods of delivering the DNA of a vaccine are described in U.S. Pat. Nos. 4,945,050 and 5,036,006, both of which are incorporated herein in their entirety by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

g. Delivery of Vaccine with Adjuvants

The pharmaceutical compositions, preferably vaccines described herein, can be administered in combination with proteins or genes encoding adjuvants, which can include: α-interferon (IFN-α), β-interferon (IFN-β), γ-interferon, IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP 1, or TAP2, or functional fragments thereof. In an exemplary embodiment, the adjuvant is IL-12.

h. Method of Generating an Immune Response with the Vaccine

The vaccine can be used to generate an immune response in a mammal, including therapeutic or prophylactic immune response. The immune response can generate antibodies and/or killer T cells which are directed to the HBV core antigen, HBV surface antigen, or the combination thereof. Such antibodies and T cells can be isolated.

Some embodiments provide methods of generating immune responses against HBV core proteins, HBV surface antigen proteins, and the combination thereof, which comprise administering to an individual the vaccine. Some embodiments provide methods of prophylactically vaccinating an individual against HBV infection, which comprise administering the vaccine. Some embodiments provide methods of therapeutically vaccinating an individual that has been infected with HBV, which comprise administering the vaccine. Diagnosis of HBV infection prior to administration of the vaccine can be done routinely.

i. Method of Treatment with the Vaccine

The vaccine can be used to generate an immune response in a mammal that is protective of the liver. The immune response can generate an antigen-specific CTL response that does not cause damage to or inflammation of the liver. In some embodiments, the vaccine can be delivered to the periphery to establish an antigen-specific immune response targeting the liver to clear or eliminate HBV infected cells without damaging or causing inflammation of the liver. In some embodiments, treatment can include delivery of a vaccine comprising an HBV consensus core antigen to the periphery to establish an antigen-specific immune response targeting the liver to clear or eliminate HBV infected cells without causing damage to or inflammation of the liver.

3. Routes of Administration

The vaccine or pharmaceutical composition can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gone guns", or other physical methods such as electroporation ("EP"), "hydrodynamic method", or ultrasound.

The vector of the vaccine can be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The HBV antigen can be delivered via DNA injection and along with in vivo electroporation.

a. Electroporation

The vaccine or pharmaceutical composition can be administered by electroporation. Administration of the vaccine via electroporation can be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, Pa.) or Elgen electroporator (Inovio Pharmaceuticals, Inc.) to facilitate transfection of cells by the plasmid.

Examples of electroporation devices and electroporation methods that can facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. Nos. 6,110,161 issued Aug. 29, 2000, 6,261,281 issued Jul. 17, 2001, and 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

4. Method of Preparing the Vaccine

Provided herein are methods for preparing the DNA plasmids that comprise the vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a US published application no. 20090004716, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following examples. It should be understood that these examples, while indicating preferred embodiments of the invention, is given by way of illustration only. From the above discussion and the examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

A consensus HBV core protein, also referred to as HBV modified or M-core construct, was designed from epitope sequences from HBV genotypes A, B, C, D and E. HBV core protein sequences from these genotypes were selected for inclusion in a construction of a consensus core that would induce immunity against a broad range of genotypes, thus providing a universal vaccine for HBV. In some embodiments, modifications of the M-core construct included addition of an IgE leader sequence. In some embodiments, the M-core protein is encoded using codon optimization and RNA optimization for enhanced expression.

1. Construction and Expression of Consensus Core Antigen

An HBV genotype A, B, C, D, and E Core consensus nucleotide sequence was constructed by generating consensus sequences of core genes for each genotype and then generating a consensus sequence of all five genotype consensuses, thus a bias toward heavily sequenced genotypes was avoided. Additionally, the sequences were collected from different countries to avoid sampling bias towards heavily sequenced genotypes. The sequences were aligned using clustal X software to develop the final HBcAg consensus sequence. As shown in FIG. 10, there was an observed relative closeness of the multi-genotype consensus HBcAg sequence to all sampled sequences from different genotypes.

After the consensus sequence was generated, several modifications were performed to increase the antigen expression levels from plasmids. Particularly, a highly efficient IgE leader sequence and a C-terminal HA tag were added, and the construct was RNA and codon optimized. This resulted in a nucleic acid sequence encoding M-core sequence with IgE leader and HA Tag (SEQ ID NO:5), which was digested with EcoRI and NotI, and cloned into the expression vector pVAX (Invitrogen) under the control of the cytomegalovirus immediate-early promoter. The resulting construct was then named as pMCore (SEQ ID NO:17).

In vitro expression tests were done using the pMcore construct and pVAX, which was used as a control. The results showing positive expression are depicted in the gel images shown in FIGS. 11A and 11B.

Additionally, the HBcAg protein was expressed by transfecting pMCore DNA plasmid containing the core gene of hepatitis B (FIG. 12). Expression of pMCore was detected using TNT® Quick Coupled Expression of Transcription/Translation System containing $^{35}$S-methionine (Promega, Madison, Wis.). The synthesized gene product was immunoprecipitated using an anti-HA monoclonal antibody targeting an encoded HA epitope, Clone HA-7 (Sigma-Aldrich). The immuno-precipitated protein was electrophoresed on a 12% SDS-PAGE gel and subsequently fixed and dried. The synthesized protein with incorporation of radioactive $^{35}$S was detected by autoradiography. This in vitro translation assay on lysate showed detectable HBcAg at an expected molecular weight of 28 kDa (FIG. 13).

The expression was further confirmed using anti-HA tagged monoclonal antibody by immunofluorescent assay. Rhabdomyosarcoma (RD) cell lines were transfected with pMCore using TURBOFECT (Thermo Scientific) according to the manufacturer's guidelines. The cells were first fixed with 2% formaldehyde and then assayed for protein expression. The fixed cells were incubated with rabbit monoclonal HA tag (Invitrogen) diluted in 'primary standard solution' (0.1% BSA, 0.2% saponin, 0.02% sodium azide) for an hours at room temperature. The cells were subsequently incubated with DyLight 594-labeled anti-rabbit secondary antibody (Thermo Scientific) for 20 minutes at room temperature. Confocal imaging was used to visualize HBcAg in the cytoplasm and around the nucleus of transfected RD cells as shown in FIG. 14. The expression pattern confirmed that a DNA plasmid carrying the consensus core gene could be highly expressed in different cells in vitro. Specifically, images were obtained using a Zeiss Axiovert 100 inverted confocal microscope. Analysis and quantification of florescence intensities were conducted using Image J software (NIH, Rockville, Md.).

2. Immunization of Mice

C57BL/6 transgenic mice were separated into two groups of four mice each and using electroporation immunized three times with 20 μg DNA at biweekly intervals (group 1—pVAX vector control; group 2 pM-core). Mice were immunized on Day 0, Day 14, Day 28 and sacrificed on Day 35. Spleens, liver and sera were harvested from sacrificed the animals.

Additionally, and to evaluate the generation of T and B cell immune responses, Balb/c mice were immunized and measured for both responses in various peripheral tissues. Mice received three intramuscular immunizations of 30 μg of pMcore or pVax followed by electroporation as depicted in the immunization scheme (FIG. 15). Particularly, six to eight week old female Balb/c mice were purchased from Jackson Laboratories. Animals were maintained in accordance with the National Institutes of Health and the University of Pennsylvania Institutional Care and Use Committee (IACUC) guidelines. For DNA immunization studies, eight animals were divided into two groups. Each animal in the immunized group received a total of three immunizations of 30 μg of pMCore two weeks apart in the tibialis anterior (TA) muscle. Each immunization was accompanied by in vivo electroporation with the CELLECTRA adaptive constant current electroporation device (Inovio Pharmaceuticals, Blue Bell, Pa.). Two 0.2 Amp constant current square-wave pulses were delivered through a triangular 3-electrode array consisting of 26-gauge solid stainless steel electrodes completely inserted into muscle. Each pulse was 52 milliseconds in length with a 1 second delay between pulses.

In vivo studies of Balb/C mice strains indicated enhancement in the magnitude of secretion of tumor necrosis factor (TNF-α), interferon gamma T-cell (IFN-γ) and the CD107a in the CD8 and CD4 T-cells taken from the spleen. FIGS. 16 and 17 demonstrate that vaccination of Balb/C mice with pM-Core enhanced the magnitude of IFN-γ secretion in CD8+ and CD4+ T Cells from the spleens. FIGS. 18 and 19 demonstrate that vaccination of Balb/C mice with pM-Core enhanced the magnitude of TNF-α secretion in CD8+ and CD4+ T Cells from the spleens. FIGS. 20 and 21 demonstrate that vaccination of Balb/C mice with pM-Core enhanced the magnitude of CD 107a secretion in CD8+ and CD4+ T Cells from the spleens.

In additional experiments, IFN-γ and TNF-α secretion were examined in T cells. To harvest splenocytes for these additional experiments, mice were sacrificed one week after the last immunization and spleens were harvested and placed in R10 media (RPMI media supplemented with 10% FBS and 1× Antibiotic-Antimycotic). The spleens were individually crushed, strained with a 40 μM cell strainer, and treated with 1 mL ACK lysis buffer for 5 min to lysis erythrocytes. The splenocytes were resuspended in a complete R10 media and used for further immunological assays.

A subset of splenocytes was resuspended in R10 media at a concentration of $10^7$ per mL and 100 μL was plated onto a 96 well round bottom plate. 100 μL of media containing pMCore pooled peptides or 10 ng/ml PMA (Sigma, St. Louis, Mo., USA) and 500 ng/ml ionomycin (Calbiochem, Novabiochem, La Jolla, Calif., USA) mix as a positive control or 0.1% dimethyl sulfoxide (Sigma, St. Louis, Mo., USA) as a negative control. All wells contained 5 uL/mL of two protein transport inhibitors, brefeldin A (GolgiPlug) and monensin (Golgistop) (All from BD Bioscience). The cells were incubated at 37° C. in 5% $CO_2$ for 5 hours and stained with LIVE/DEAD Fixable Dead Cell Stain (invitrogen) for 10 min at 37° C. Extracellular staining was performed using antibodies specific to mouse CD3, CD4 and CD8. Splenocytes were then permeabilized and washed using BD CYTOFIX/CYTOPERM and PERM/WASH (BD Bioscience) respectively. Intracellular cytokines were then stained with antibodies to mouse Interferon-gamma and Tumor Necrosis Factor-alpha.

Conjugated anti-mouse antibodies were used during the extracellular and intracellular staining including: CD3-Phycoerythrin/Cy7 (PE/Cy7), CD4-peridinin chlorophyll protein (PerCP), CD8-allophycocyanin (APC), IFN-γ-Alexa Fluor 700, TNF-a-fluorescein isothiocyanate (FITC) and IL-2-phycoerythryin cyanine (PE) (all from BD Biosciences, San Jose, Calif.).

Figure 22:
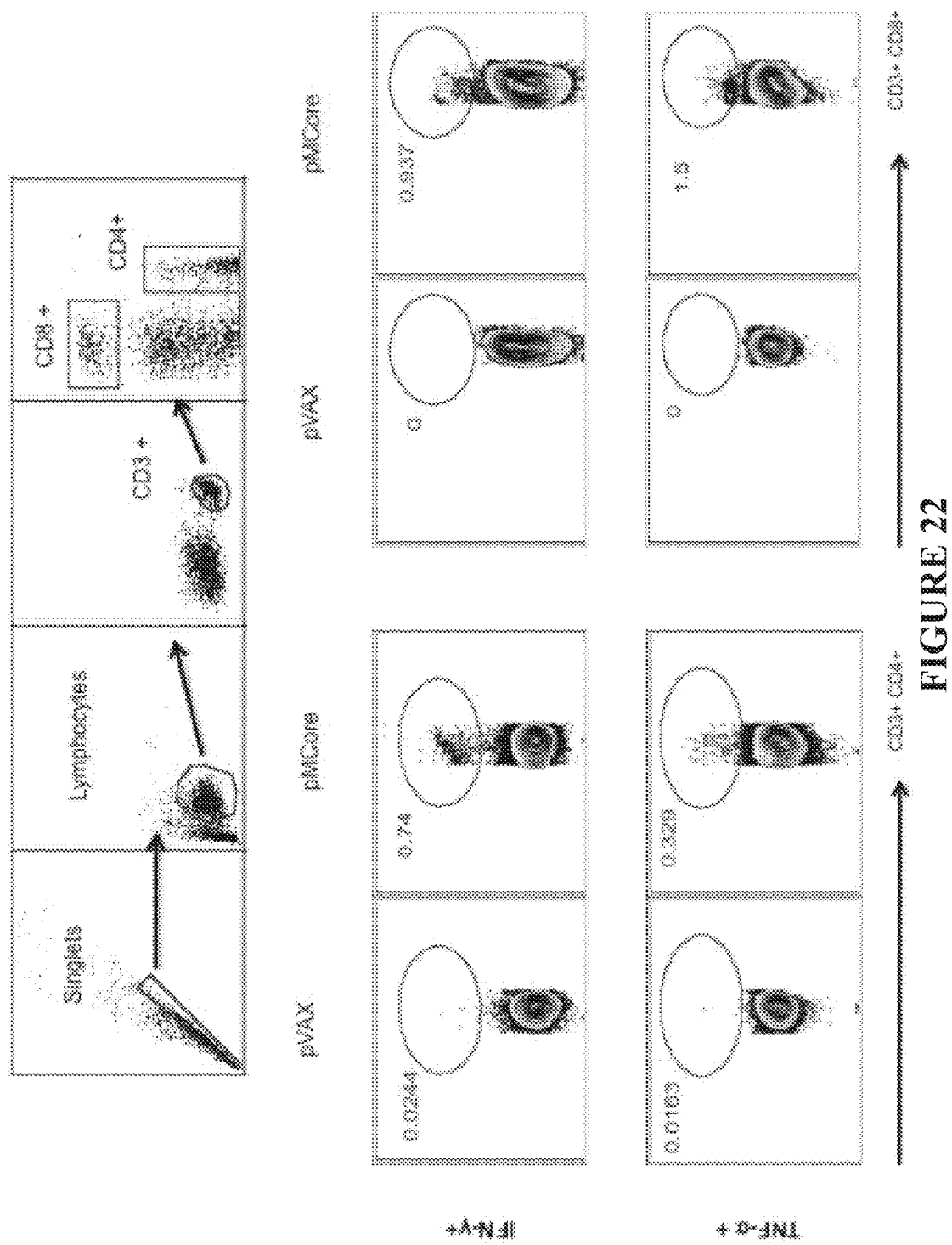
FIG. 22 shows the average percent HBcAg-specific CD4 or CD8 IFN-γ$^+$, TNF-α$^+$ secreting cells from Balb/c mice immunized with the control pVAX or the consensus core antigen pMCore.
Figure 23:
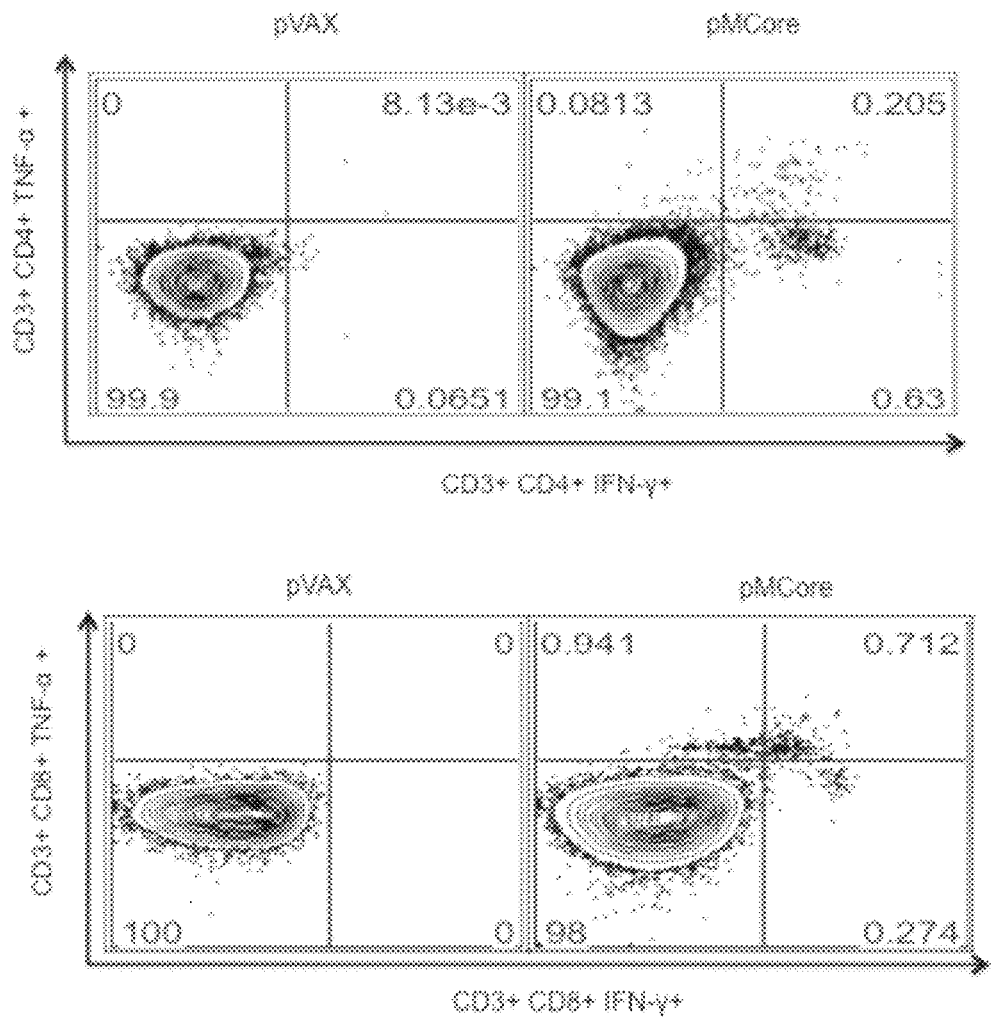
FIG. 23 shows the average percent HBcAg-specific CD4 or CD8 double positive producing cells from Balb/c mice immunized with the control pVAX or the consensus core antigen pMCore.

The average HBcAg-specific IFN-γ T cell response induced was robust at 2000 (±210) SFU per million splenocytes. Interestingly, intracellular staining of stimulated splenocytes revealed that both $CD4^+$ and $CD8^+$ cells produce almost the similar amount of antigen-specific IFN-γ, 0.74 and 0.94, respectively, but and different levels of TNF-α with about 0.3% and 1.5% of the $CD4^+$ and $CD8^+$ cells, respectively (FIG. 22). A similar trend was observed with cells that were double positive for both cytokines. There were lesser double positive $CD4^+$ cells, about 0.2%, in the spleen than double positive $CD8^+$ cells, which averages 0.7% (FIG. 23).

Figure 24:
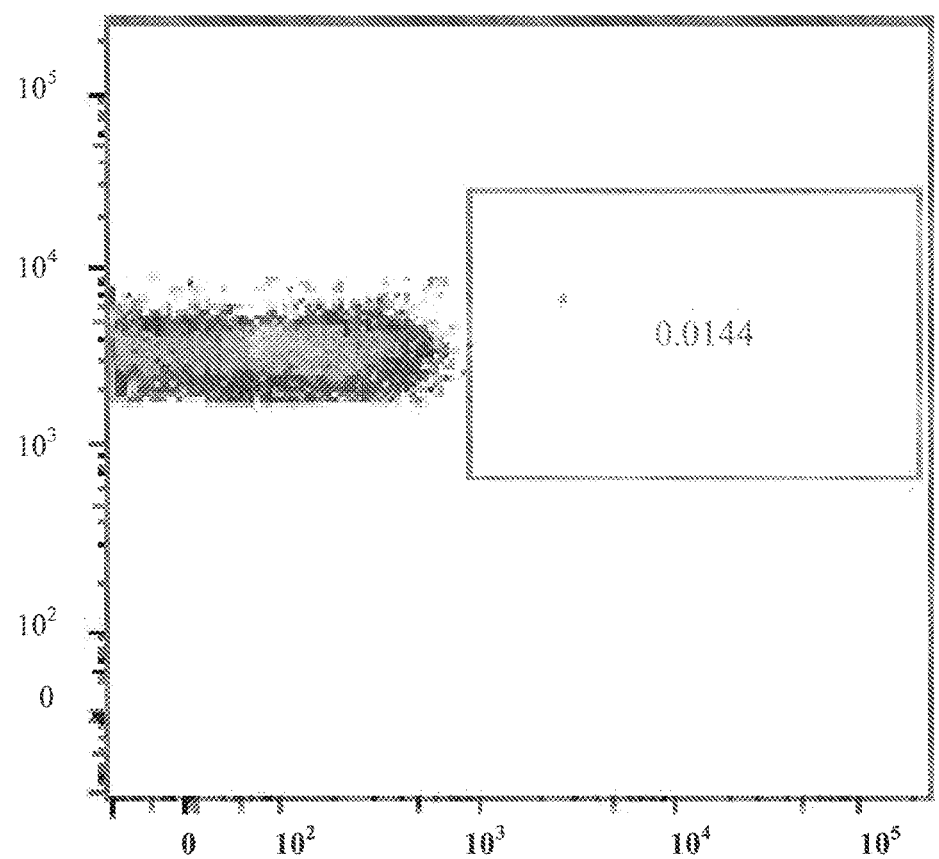
FIG. 24 shows interferon-gamma T cell response in liver from Balb/C mice vaccinated with pM-Core.
Figure 25:
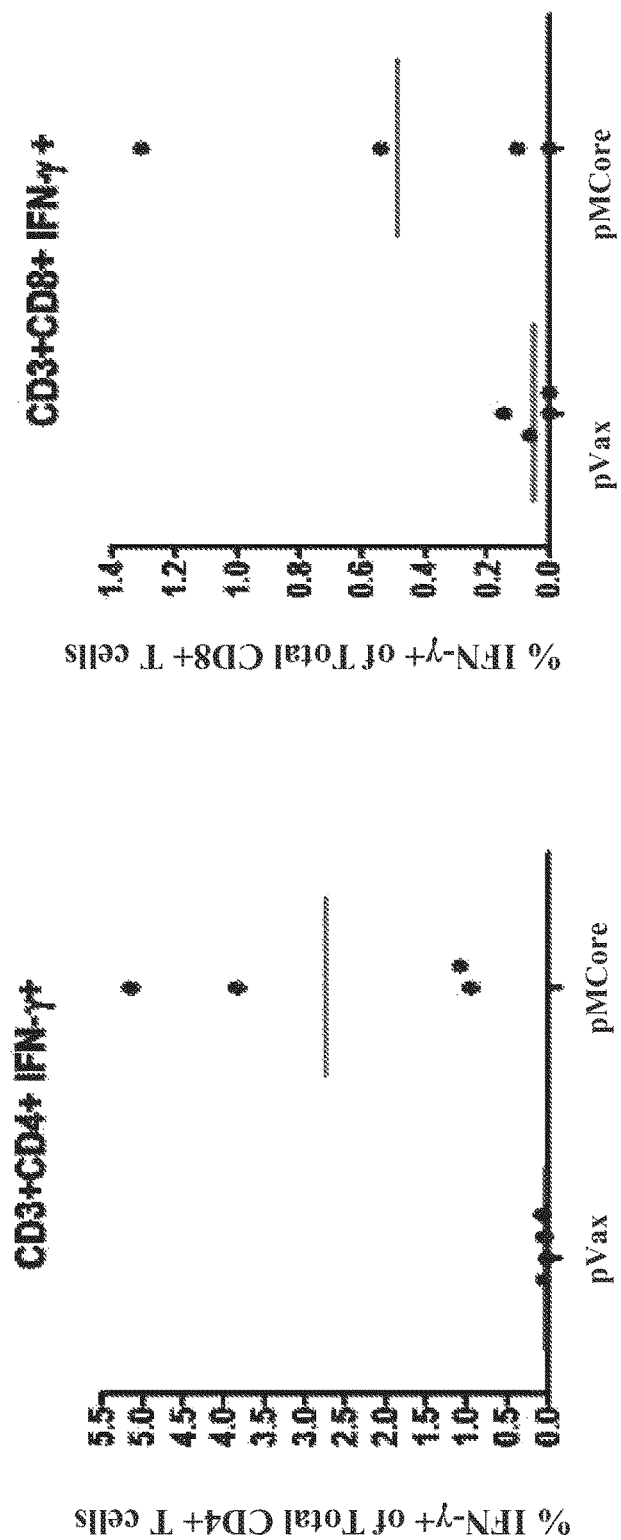
FIG. 25 shows interferon-gamma T cell response in liver from Balb/C mice vaccinated with pM-Core.
Figure 26:
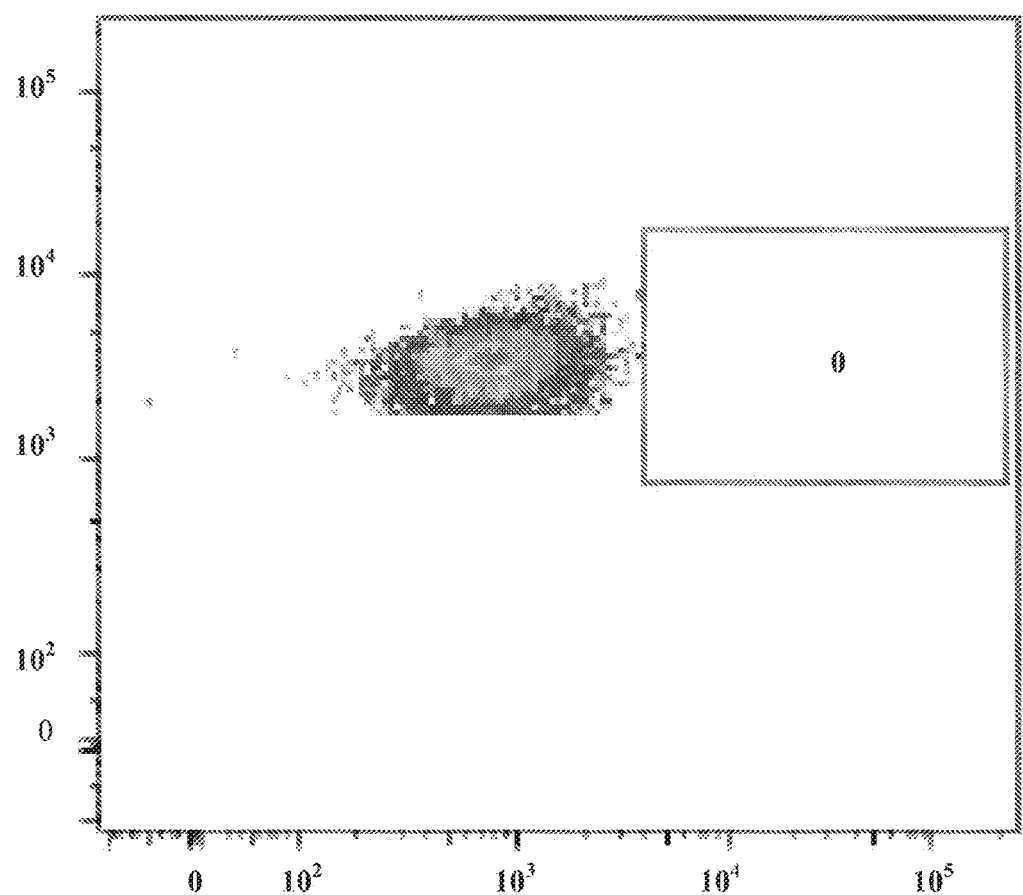
FIG. 26 shows Tumor Necrosis Factor-α T cell response in liver from Balb/C mice vaccinated with pM-Core.
Figure 27:
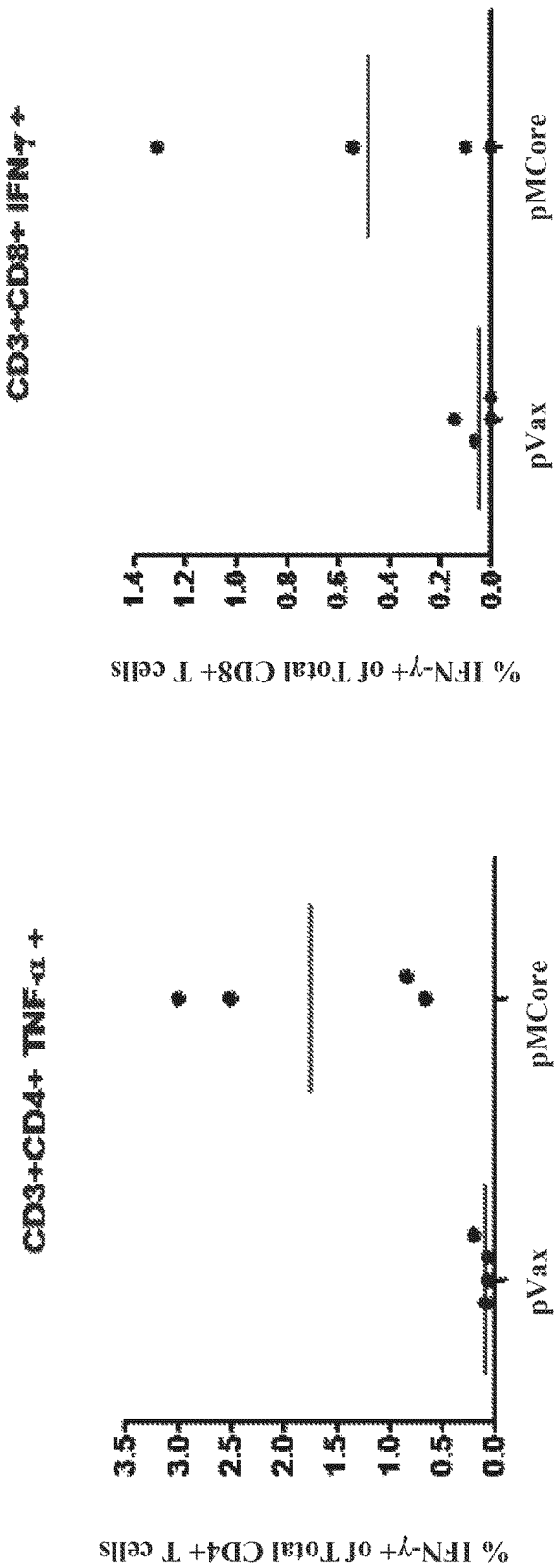
FIG. 27 shows Tumor Necrosis Factor-α T cell response in liver from Balb/C mice vaccinated with pM-Core.

HBV specific T-cell migration to the liver was also demonstrated in animals administered the pM-Core DNA vaccine. Targeting HBV core antigen specific T cells with high frequency and effector function to the liver is an important goal for development of an HBV immune therapy. Following immunization, animals were sacrificed and their livers were removed and HBV specific effector T cell migration to the liver was determined. The results show that the pM-Core vaccine drives effector T cells to the liver in vivo. FIGS. 24 and 25 demonstrate interferon-γ T cell liver response, and FIGS. 26 and 27 demonstrate Tumor Necrosis Factor-α liver immune response, and the elevated response that results from vaccination with pM-Core.

The M-core consensus immunogen encoded by the pM-core DNA construct drives strong balanced CD4+/CD8+ T cell immune responses. Induced T cells traffic to the liver at high frequency and exhibit the correct effector phenotype for immune clearance post HBV infection supporting further development of this immune therapeutic vaccine.

Figure 28:
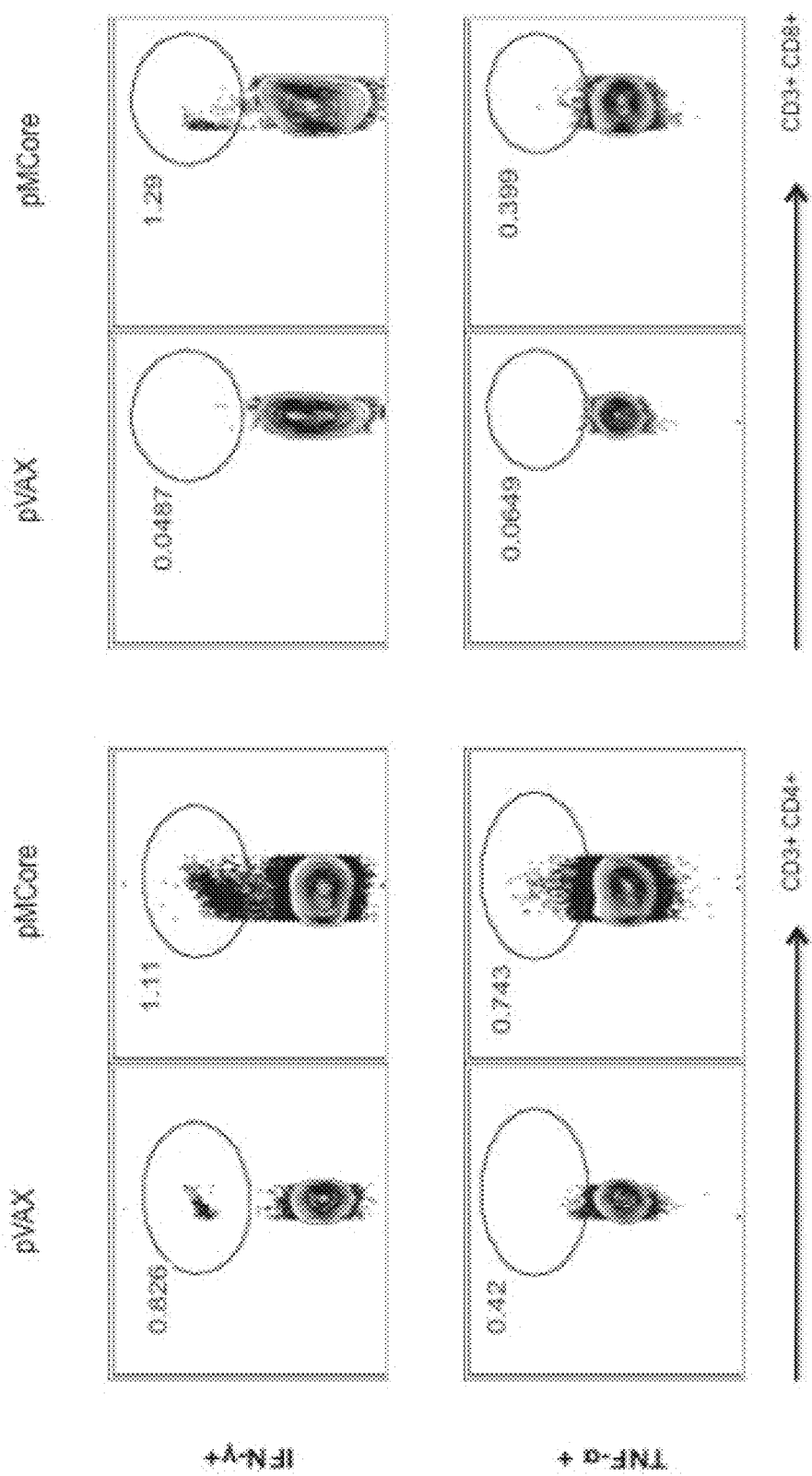
FIG. 28 shows the percent HBcAg-specific CD4 and CD8 IFN-γ$^+$, TNF-α$^+$ producing cells in the liver of Balb/c mice immunized with the control pVAX or the consensus core antigen pMCore.
Figure 29:
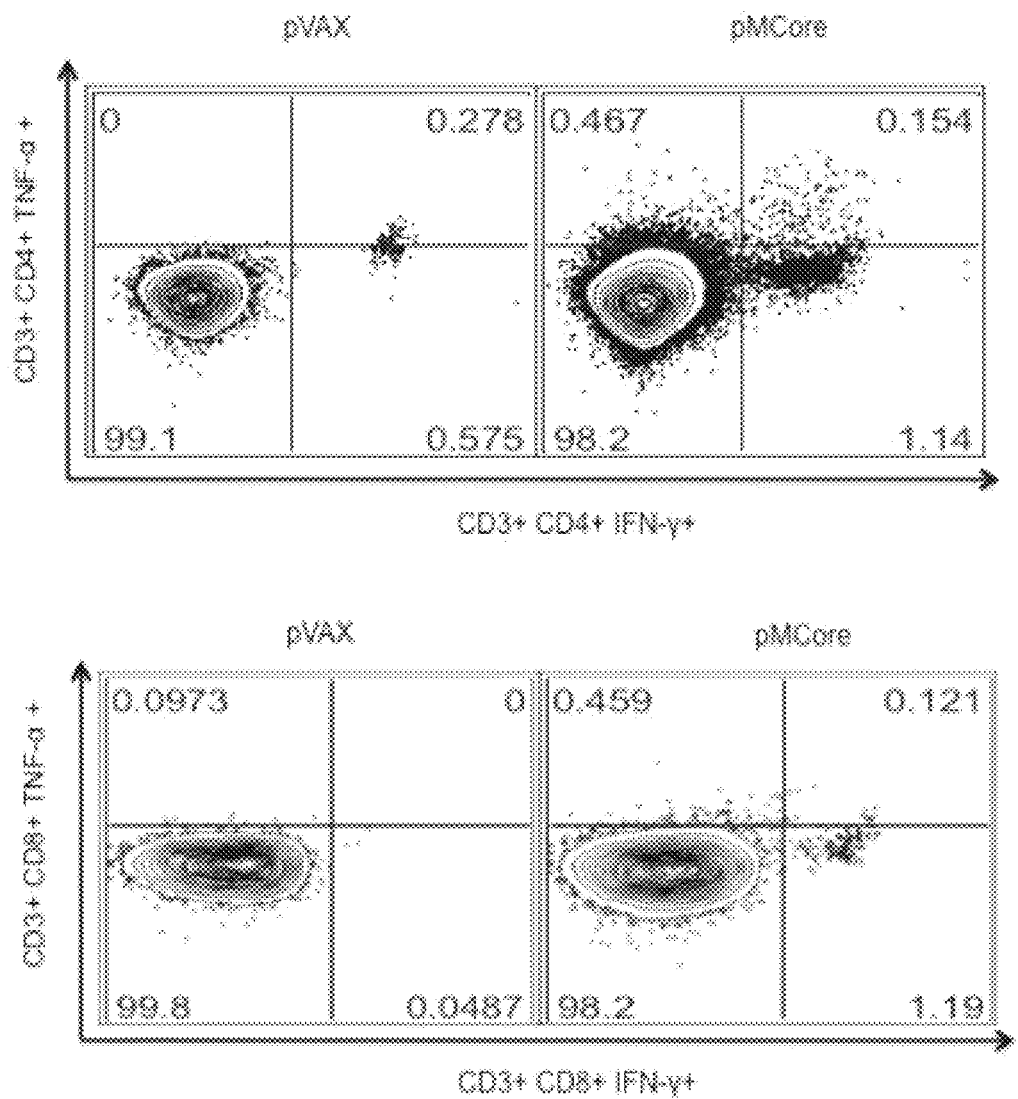
FIG. 29 shows the average percent HBcAg-specific CD4 or CD8 double positive producing cells in the liver of Balb/c mice immunized with the control pVAX or the consensus core antigen pMCore.
Figure 30:
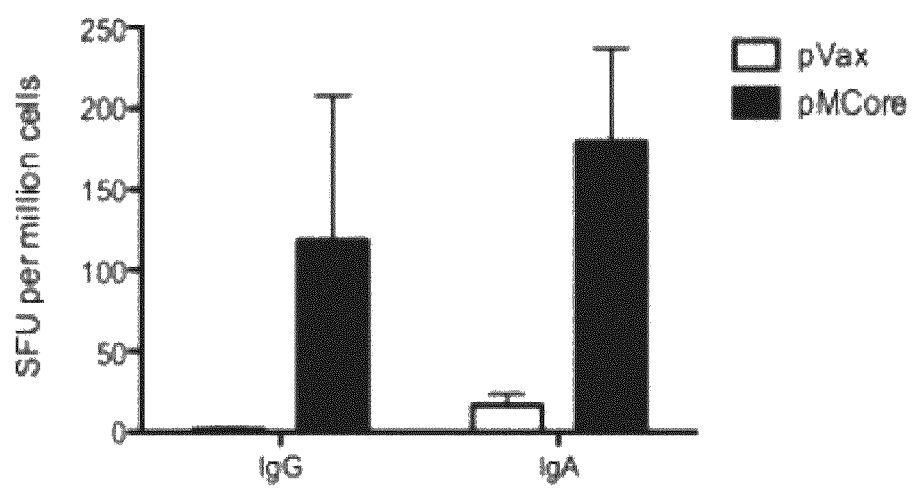
FIG. 30 shows antigen-specific antibody producing splenocytes. The values are the means±standard error of the mean. Significance was determined by Student's t test.

The cytokine producing capabilities of intrahepatic antigen-specific T cells after DNA immunization was also examined. Each liver was perfused by directly injecting 1 mL of PBS into the hepatic vein of each mouse. Particularly, livers were harvested, crushed and resuspended in 5 mL of 44% isotonic percoll. The mixtures were underlied with 3 mL 66% isotonic percoll and centrifuged for 20 minutes at 2000 rpm for gradient separation. Lymphocytes were collected and washed in 10 mL R10 and treated with ACK lysis buffer as necessary. Both CD4 and CD8 T cells isolated from the liver produce IFN-γ and TNF-α when stimulated in vitro with HBcAg peptide (FIGS. 28 and 29). While the CD4 T cells showed a high percentage of double producers, the CD8 showed little to no IFN-γ+TNF-α+ producing cells. Instead, a majority of the CD8 T cells produced only IFN-γ or TNF-α. An enrichment of HBcAg-specific CD4 T cells in the liver was observed, which was opposite to that of the spleen. The percent HBcAg-specific CD4 T double positive in the resting liver were comparable to that observed in the spleen. Moreover, peripheral CD8 T cells were confirmed to be better double producers than liver resident CD8 T cells. It was also observed that antibody-producing capabilities of liver resident B cells from immunized mice. Interestingly, the liver as a mucosal organ produced higher antigen-specific IgA than IgG (FIG. 30), an important observation that has not been previously been studied.

Figure 31:
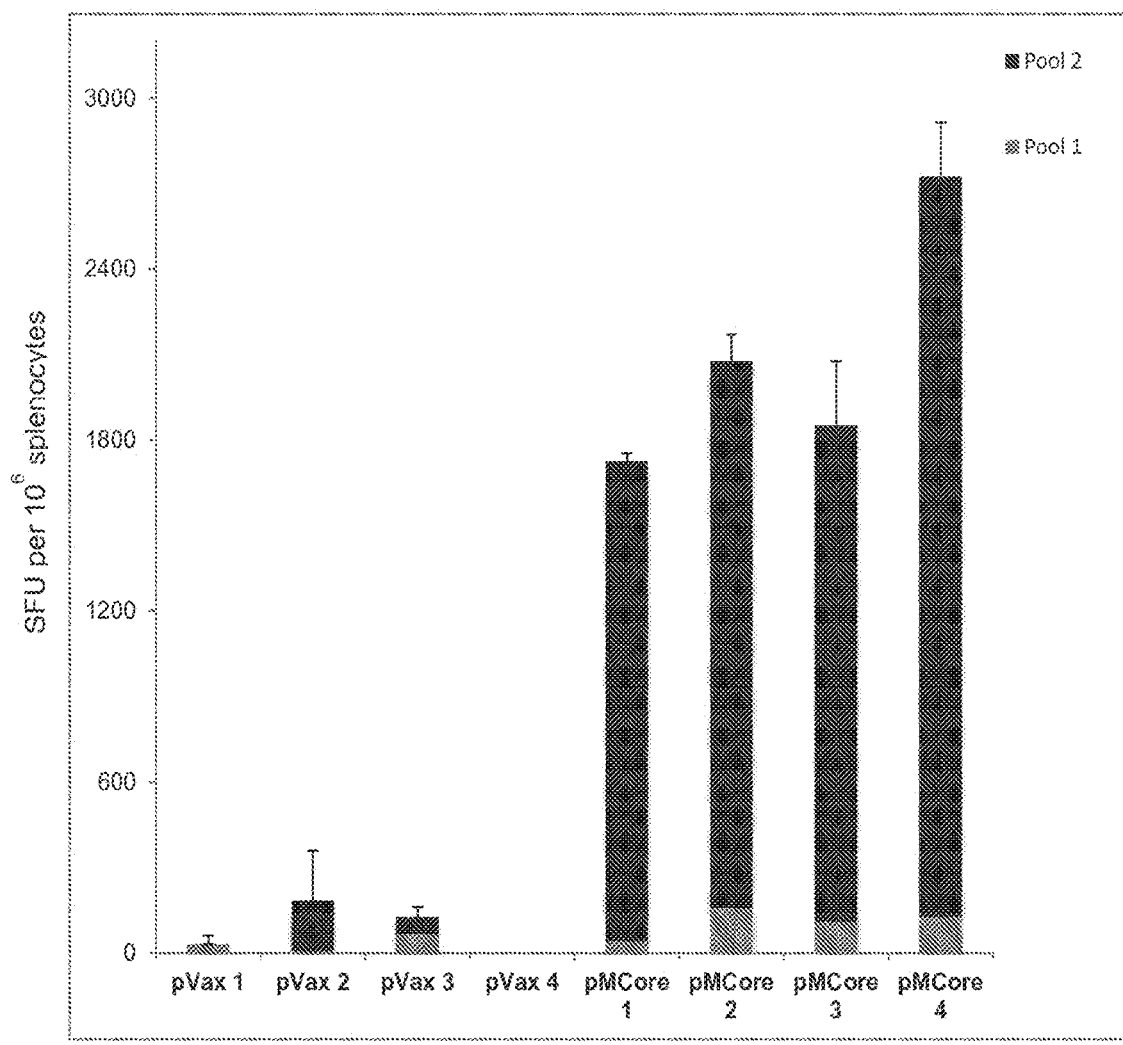
FIG. 31 shows data from ELISPOT assays.

FIG. 31 shows Cellular Immune responses Induced by pM-Core using an Enzyme-linked immunosorbent spot (ELISPOT) assay. Splenocytes were stimulated with two pools of 15-mer peptides spanning the entire length of pMCore and over lapping by 8 amino acids. 200,000 splenocytes in R10 media were plated in a 96 well IFN-γ capture antibody (R&D system) coated plate and stimulated overnight in the presence of a specific peptide pool at 37° C. in 5% $CO_2$. Cells were washed out and plates were incubated overnight with biotinylated anti-mouse IFN-γ detection antibody (R&D system). Streptavidin-alkaline phosphatase and 5-bromo-4-chloro-3'-indolylphosphate p-toluidine salt and nitro blue tetrazolium chloride were subsequently used to develop spots. Spots were counted using an automated ELISPOT reader (CTL Limited). As shown in FIG. 31, immunization with pMCore could induce strong cellular immune responses. Although, the dominant epitopes are yet to be mapped, it was clear from the data that the dominant epitopes were biased towards peptide pool 2. The average HBcAg-specific IFN-γ T cell responses were about 2000 (±210) SFU per million splenocytes.

Figure 32:
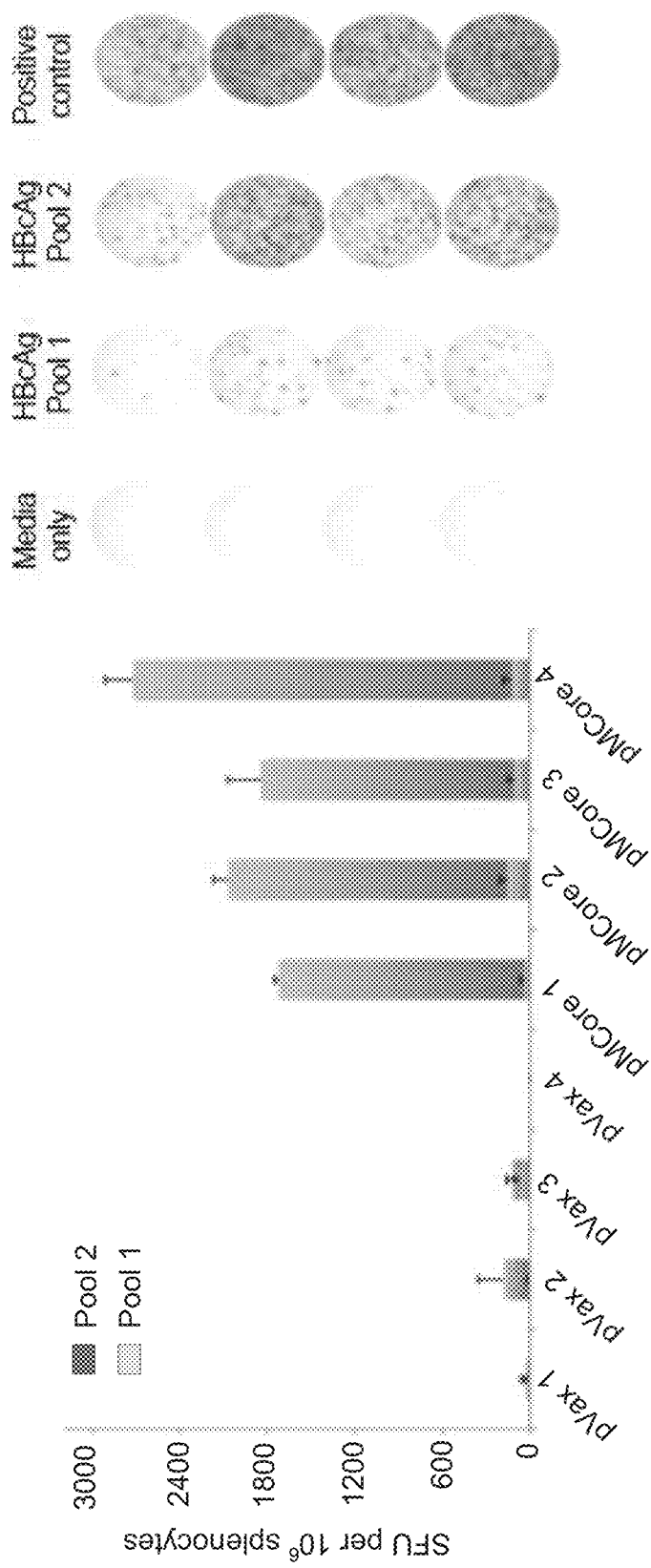
FIG. 32 shows the frequency of HBcAg-specific IFN-γ spot forming units (SFU) per million splenocytes after stimulation of spleen cells from immunized mice.

The ELISPOT assay was used to further examine IFN-γ. Particularly, splenocytes were stimulated with two pools of 15-mer peptides spanning the entire length of HBcAg and over lapping by 8 amino acids. There were 33 total individual peptides, which were pooled randomly with the first 17 peptides going into pool 1 and last 16 in pool 2. The IgELs and HA tag were excluded to make the peptide as close to the natural antigen as possible. 200,000 splenocytes in R10 media were plated in a 96 well IFN-γ capture antibody (R&D system) coated plate and stimulated overnight in the presence of a specific peptide pool at 37° C. in 5% $CO_2$. Cells were washed out and plates were incubated overnight with biotinylated anti-mouse IFN-γ detection antibody (R&D system). Streptavidin-alkaline phosphatase and 5-bromo-4-chloro-3'-indolylphosphate p-toluidine salt and nitro blue tetrazolium chloride were subsequently used to develop spots. Spots were counted using an automated ELISPOT reader (CTL Limited). It was observed that one week after the final immunization, pMCore immunized mice showed evidence of strong HBcAg T cell responses as identified by the IFN-γ ELISPOT assay following ex vivo stimulation. FIG. 32 clearly showed the dominant epitopes are biased towards peptide pool 2.

In vivo cytotoxicity assay studies were performed using carboxyfluorescein diacetate succinimidyl ester (CFSE) labeling combined with flow cytometry. Cell division at among cells of cell populations we assessed. Splenocytes were isolated from naïve mice and divided into two populations. One population, CFSE high labeled, was pulsed with relevant peptide (e.g. HBV core peptides). The other population, CFSE low labeled, was pulsed with irrelevant peptide (e.g. HCV NS3 peptides). The labeled, peptide treated cells were combined and used in adoptive transfer experiments in which flow analysis was performed. The combined populations of treated, labeled target cells were administered to two groups of mice, a control group and an immunized group. Splenocytes were isolated from each group of mice and samples were run on a flow cytometer. The amount of CFSE was measured. Typically, in such experiments, two peaks form, the first being the irrelevant peptide; the second being the immunizing peptide in the peak indicating greater CFSE.

Figure 33:
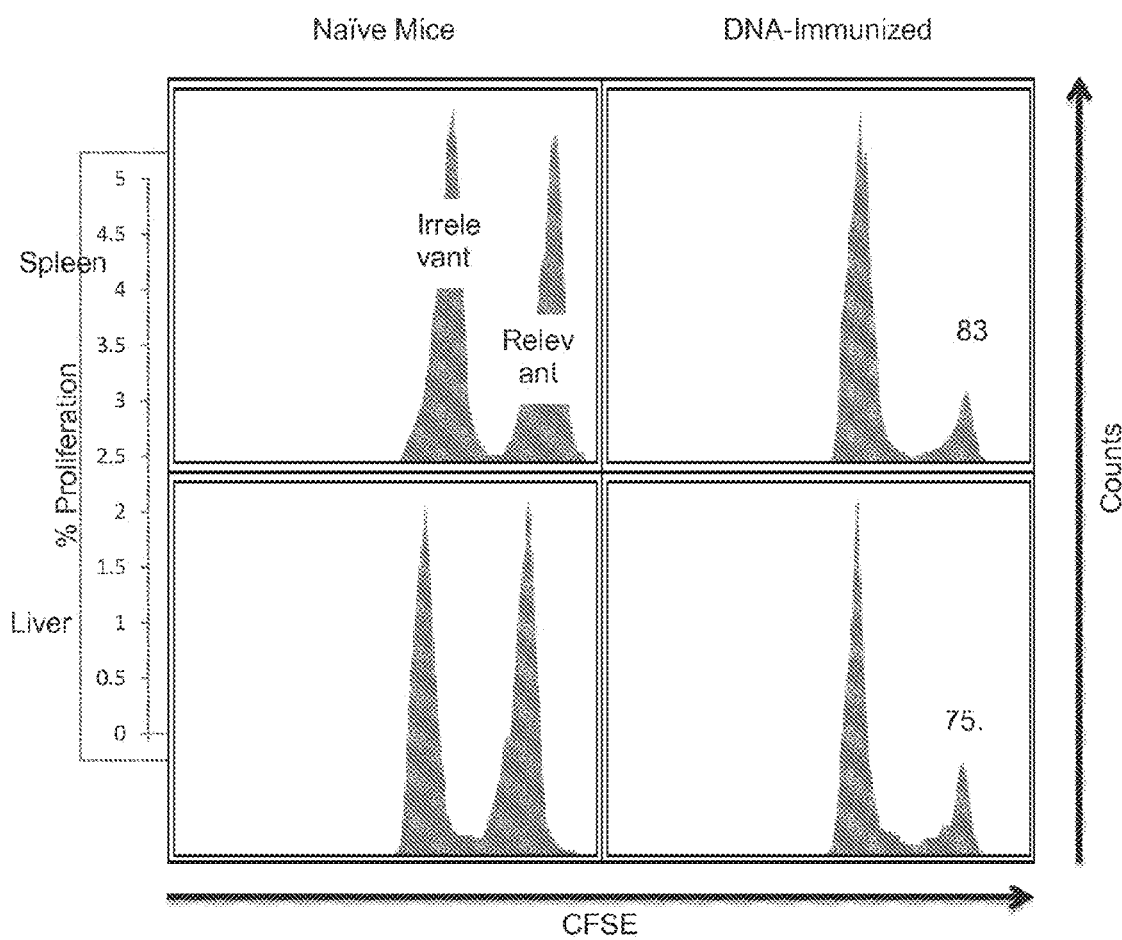
FIG. 33 shows data from experiments using CSFE labeled cells to compare elimination of peptide treated target cells in vivo by CD8 T cells in vaccinated and unvaccinated animals.

FIG. 33 demonstrate that CD8 T cell induced by vaccination can specifically eliminate target cells in vivo. The results demonstrate that samples of spleen and liver from naïve mice contained nearly equal amounts of cells which were in the irrelevant peptide and relevant peptide peaks while the results clearly showed that among immunized groups, the peaks for cells derived from those pulsed with the relevant peptide were significantly less than irrelevant peptide. These data demonstrate that target cells treated with the HBV peptide were specifically eliminated in mice immunized with the HBV vaccine but not in the non-immunized mice. Any elimination of target cells treated with the irrelevant peptide, if it occurred at all, was the same in mice immunized with the HBV vaccine and the non-immunized mice and significantly less than elimination of target cells treated with the HBV peptide.

Figure 34:
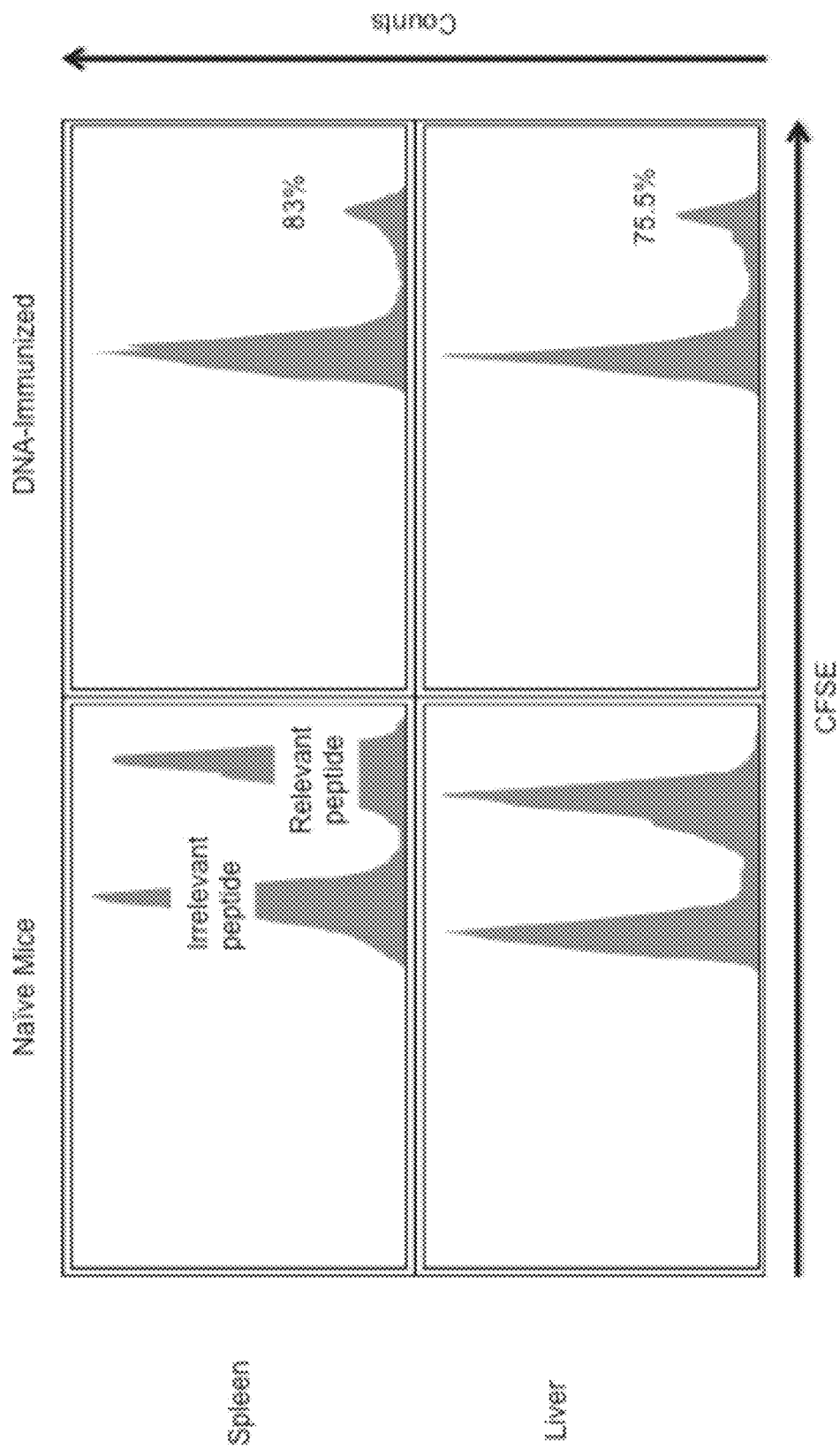
FIG. 34 shows in vivo specific killing. Two groups of mice immunized with either pVax (control) or pMCore received CFSE-labeled target cells (CFSE$^{lo}$ pulsed with irrelevant peptide or CFSE$^{hi}$ pulsed with epitope-specific peptide) through the tail vain. CFSE-labeled cells were recovered and analysis by FACS was utilized to quantify percent killing.

The ability of HBV-specific CD8 T cells induced after DNA immunization to specifically eliminate target cells in vivo was further examined Human CTLs that target the core antigen are important in acute clearance of HBV versus chronic infection. One week after the final immunization, 4 mice from each of the two groups, pVax or pMCore immunized, were adoptively transferred with target splenocytes that had either been pulsed with HBcAg (relevant) or HCV-NS3/4A (irrelevant) peptides. Briefly, splenocytes from naïve mice were stained with either 1 µM or 1 nM CFDA SE (invitrogen). The labeled splenocytes were then coated with indicated peptides (1 µM) and $10^7$ cells of each population intravenously injected into naïve or immunized mice. After 24 or 90 hours cells from the spleen and liver were isolated and analyzed by flow cytometry. The percent killing was calculated as follows: 100−([(% relevant peptide pulsed in infected/% irrelevant peptide pulsed in infected)/(% peptide pulsed in uninfected/% irrelevant peptide pulsed in uninfected)]×100). By gating on CFSE labeled splenocytes to track killing, it was observed that the pMCore vaccinated mice were able to induce strong specific killing of antigen-pulsed target cells as shown in FIG. 34. Average percent killing observed in the spleen was about 83% while the average in the liver was 76%, showing that vaccine-induced CTLs that migrate to and are retained in the liver are capable of killing HBV peptide pulsed target cells. This was the first study to show induction of HBcAg-specific CTL responses in the liver, by any method and specifically by systemic immunization. This data provided evidence that peripheral immunization can induce effector cells that can migrate to the liver and lyses target cells.

Figure 35:
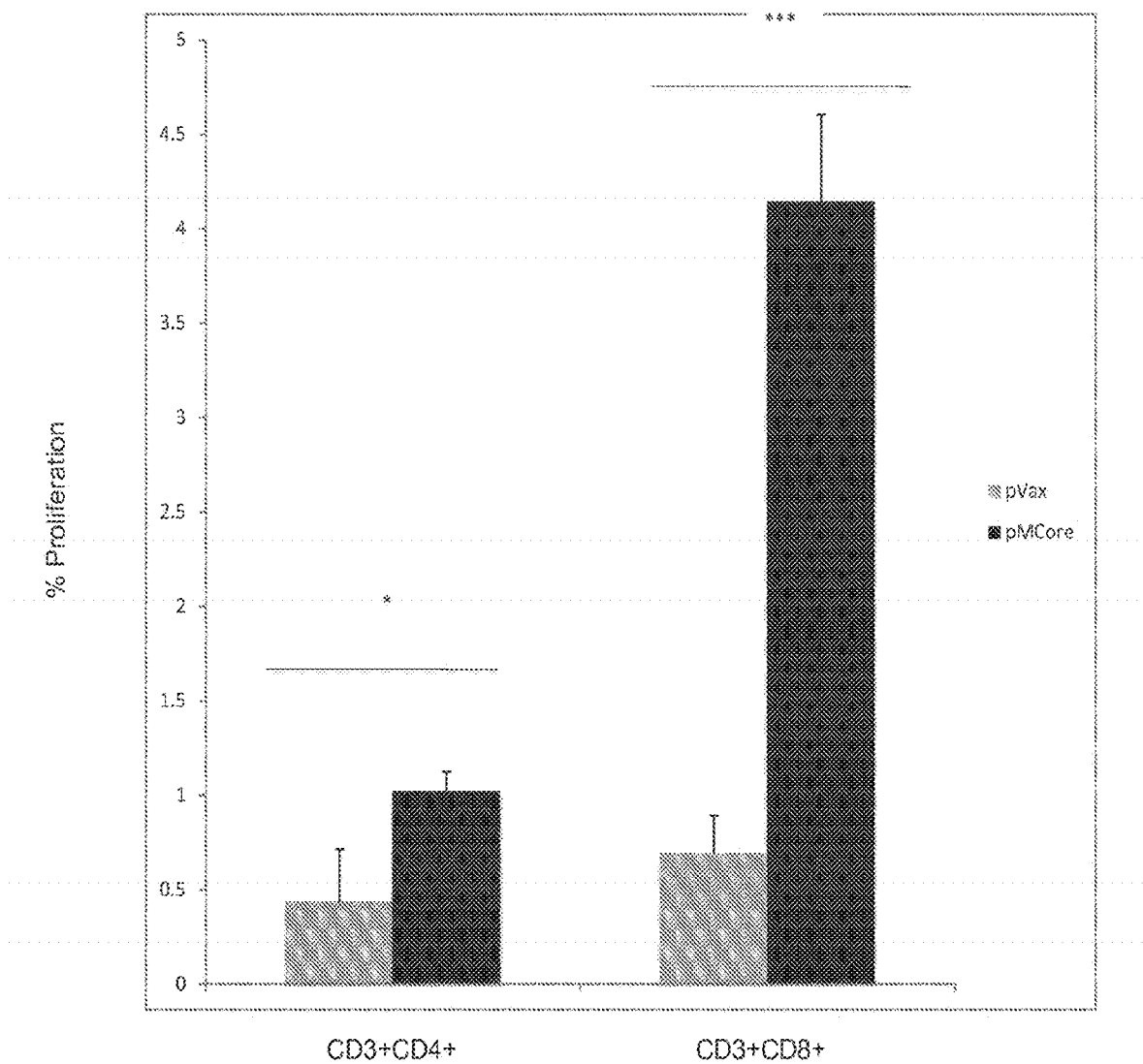
FIG. 35 shows a comparison of percent proliferation of CD3+CD4+ cells and CD3+CD8+ treated with pVax vector (control) or with plasmid pMCore which expresses HBV M-core.

FIG. 35 shows the data collected from the T cell Proliferation Assay using CFSE labeling. Percent proliferation of CD3+CD4+ cells and CD3+CD8+ treated with pVax vector (control) or with plasmid pMCore which expresses HBV M-core were compared. Briefly, the isolated splenocytes were stained with the carboxyfluorescein diacetate, succinimidyl ester (CFDA-SE) Cell Tracer Kit (Invitrogen) per the manufacturer's instructions. Stained cells were washed three times with saline and stimulated with the pMCore-specific overlapping peptides. The cells were incubated at 37° C. for 96 hours. After 48 hours, 50% of the culture media were removed and replaced with fresh R10. At day 4, cells were harvested and stained with CD3, CD4 and CD8-specific monoclonal antibodies (BD Pharmingen). Cells were fixed with PBS with 1% Paraformaldehyde (PFA) and acquired on a FACScalibur (Becton Dickinson). The data were analyses using FlowJo program. CFSE low and CFSE medium population was considered as proliferated cells. As shown in FIG. 35, the CD3+CD8+ T cells isolated from the spleen proliferated more compared to the CD3+CD4+ T cells.

Figure 36:
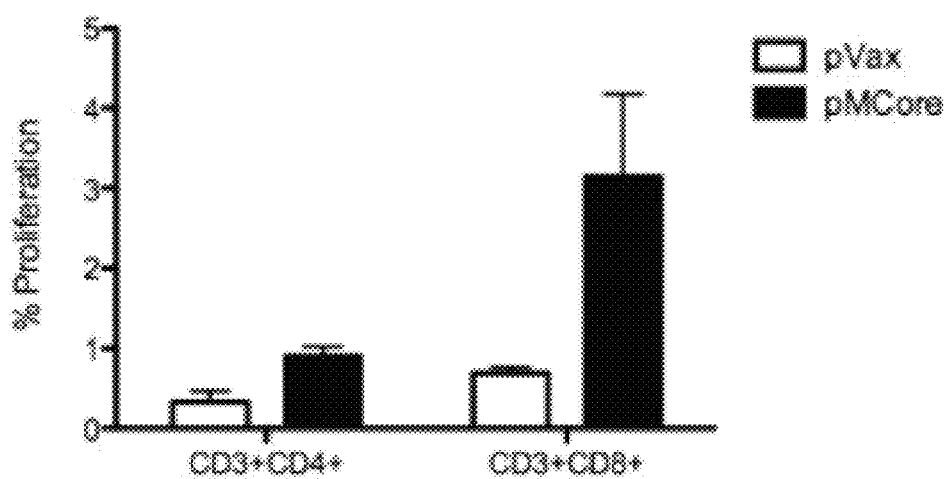
FIG. 36 shows the percent proliferation of CD4 and CD8 T cells.

Further experiments with the T cell proliferation assay also used CFSE labeling. Particularly, isolated splenocytes were stained with the carboxyfluorescein diacetate, succinimidyl ester (CFDA-SE) Cell Tracer Kit (Invitrogen) as per the manufacturer's instructions. Stained cells were washed three times with saline and plated in a 96-well U-bottomed plate in a total volume of 200 µL of media containing HBcAg pooled peptides at a concentration of 1 µg/mL. The cells were incubated at 37° C. for 96 hours. After 48 hours, 50% of the culture media were removed and replaced with fresh R10. The difference in the cytokine production between both CD4 and CD8 T cells as discussed above was comparable to their ultimate proliferation capacity. After 4 days of stimulation with antigen specific peptides, the $CD8^+$ T cells proliferated more than 2 fold higher than the $CD4^+$ cells (FIG. 36) demonstrate a clear CD8 T cell bias in the response.

Figure 37A:
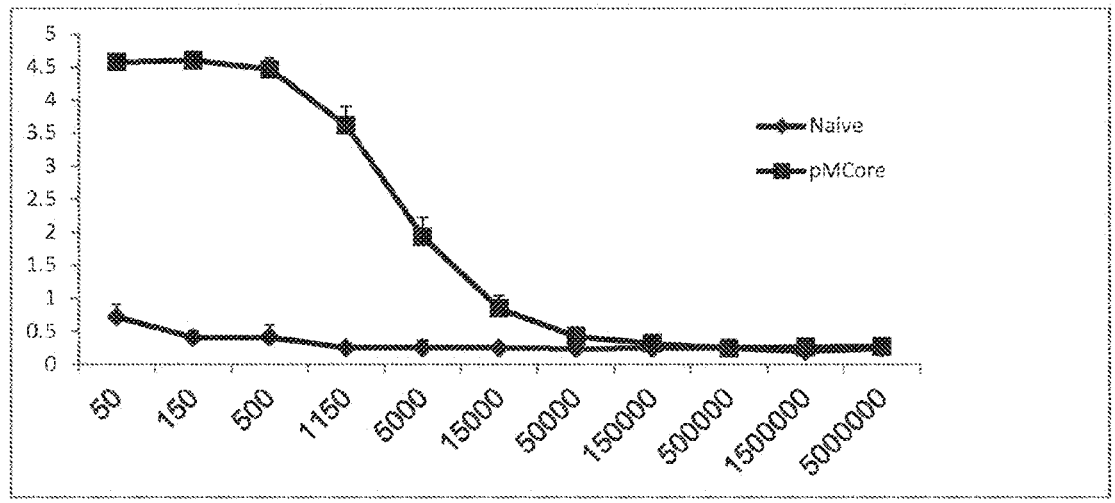
FIGS. 37A and 37B shows a comparison of anti-HBV core antibody in serial dilution of sera from animals treated with pVax vector (control) or with plasmid pMCore which expresses HBV M-core.
Figure 37B:
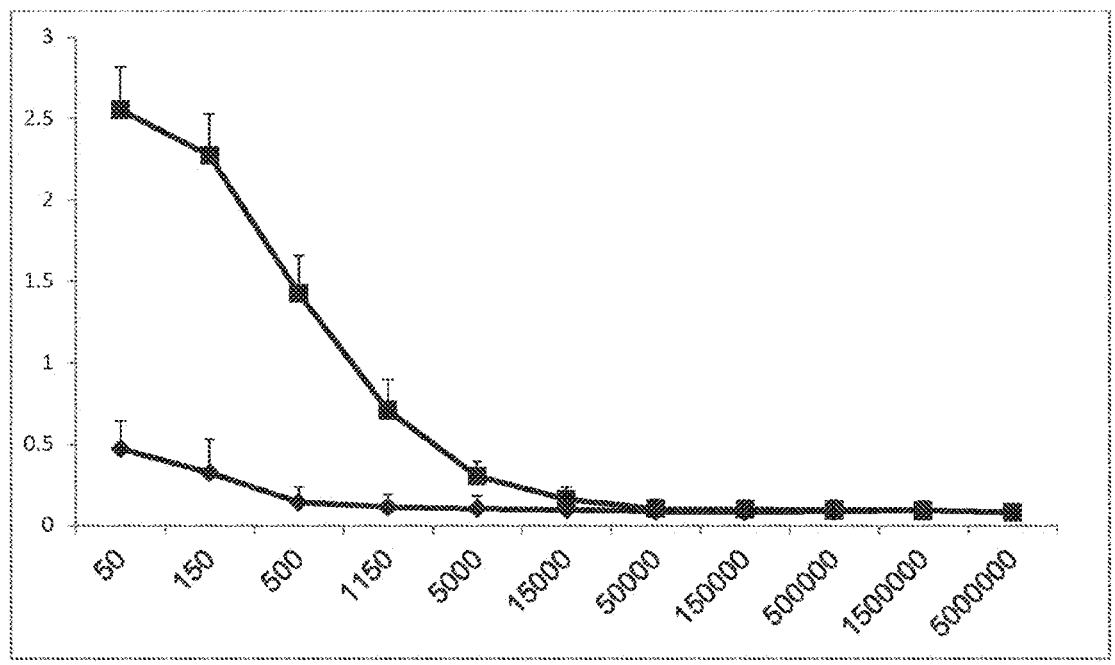

FIGS. 37A and 37B are ELISA data showing a comparison of anti-HBV core antibody in serial dilution of sera from animals treated with pVax vector (control) or with plasmid pMCore which expresses HBV M-core. Briefly, high-binding ELISA plates (Costar, Corning, N.Y.) were coated with 1 µg/ml HBcAg protein in PBS, at 4° C. for 24 h and then were washed with PBS-Tween and blocked with PBS containing 1% BSA for 2 h at room temperature. Serially diluted serum samples were added to the wells and incubated for 1 h at room temperature. After washing, bound serum Antibody was revealed by HRP-labeled goat anti-mouse IgG (FIG. 37A) or IgA (FIG. 37B). The peroxidase-conjugated Abs were detected using tetramethylbenzidine (Sigma-Aldrich) as the substrate, and OD at 450 nm was measured with the Multiscan ELISA Plate Reader. The antigen-specific humoral response in sera collected from immunized mice were observed.

Figure 39:
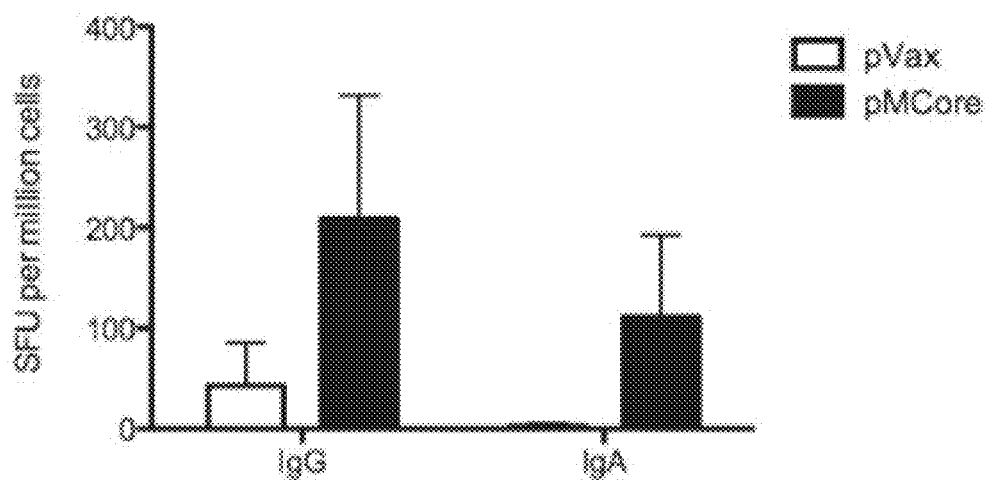
FIG. 39 shows the HBcAg-specific humoral immune response induced by pMCore in the sera and splenocytes. The values are the means±standard error of the mean. Significance was determined by Student's t test.

To further explore the immune response induced in pMCore-immunized mice, antigen-specific IgG and IgA responses were analyzed by B cell ELISpot as well as in ELISA using splenocytes and sera, respectively, collected following vaccination. Splenocytes were isolated and purified as described above. For the ELISAs, high-binding ELBA plates (Costar, Corning, N.Y.) were coated with 1 µg/ml HBcAg protein in PBS, at 4° C. for 24 hours and then were washed with 0.1% PBS-Tween then and blocked with PBS containing 1% BSA for 2 hours at room temperature. Serially diluted serum samples were added to the wells and incubated for 1 hour at room temperature. After washing, bound serum Antibody was revealed by HRP-labeled goat anti-mouse IgA or IgG. The peroxidase-conjugated antibodies were detected using tetramethylbenzidine (Sigma-Aldrich) as the substrate, and OD values at 450 nm were measured with the Multiscan ELISA Plate Reader. A high IgG and IgA titer was observed in the sera of immunized mice when compared to control animals (FIG. 38). B cell ELISpot from immunized mice (FIG. 39) demonstrate HBcAg-specific IgG and IgA at approximately 200 SFU and 100 SFU per million cells, respectively. This illustrated activation of the B cell compartment by immunization with pMCore. The synthetic HBcAg plasmid effectively induced antigen-specific cellular and humoral responses after 3 immunizations.

Figure 40:
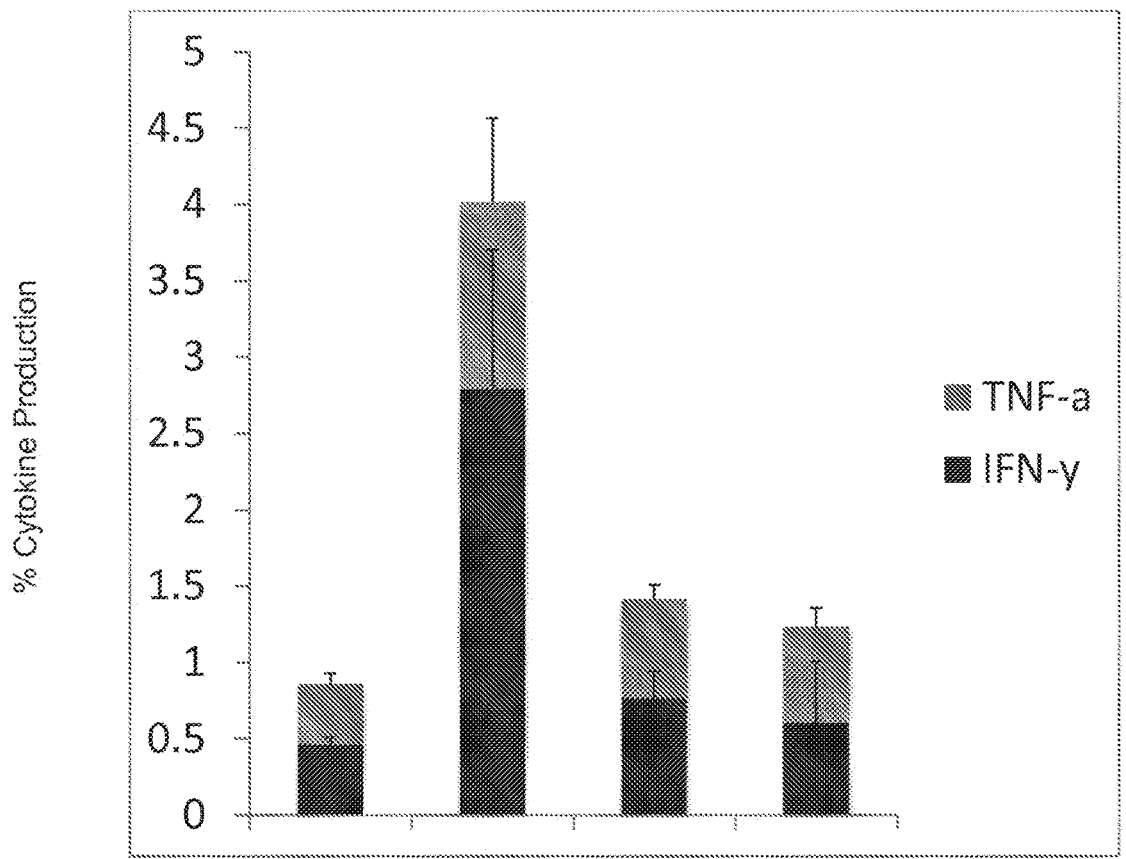
FIG. 40 shows percent TNF-a and IFN-g from CD4+ and CD8+ spleen and liver cells.

FIG. 40 demonstrates percent TNF-α, and IFN-γ from CD4+ and CD8+ spleen and liver cells.

Figure 41:
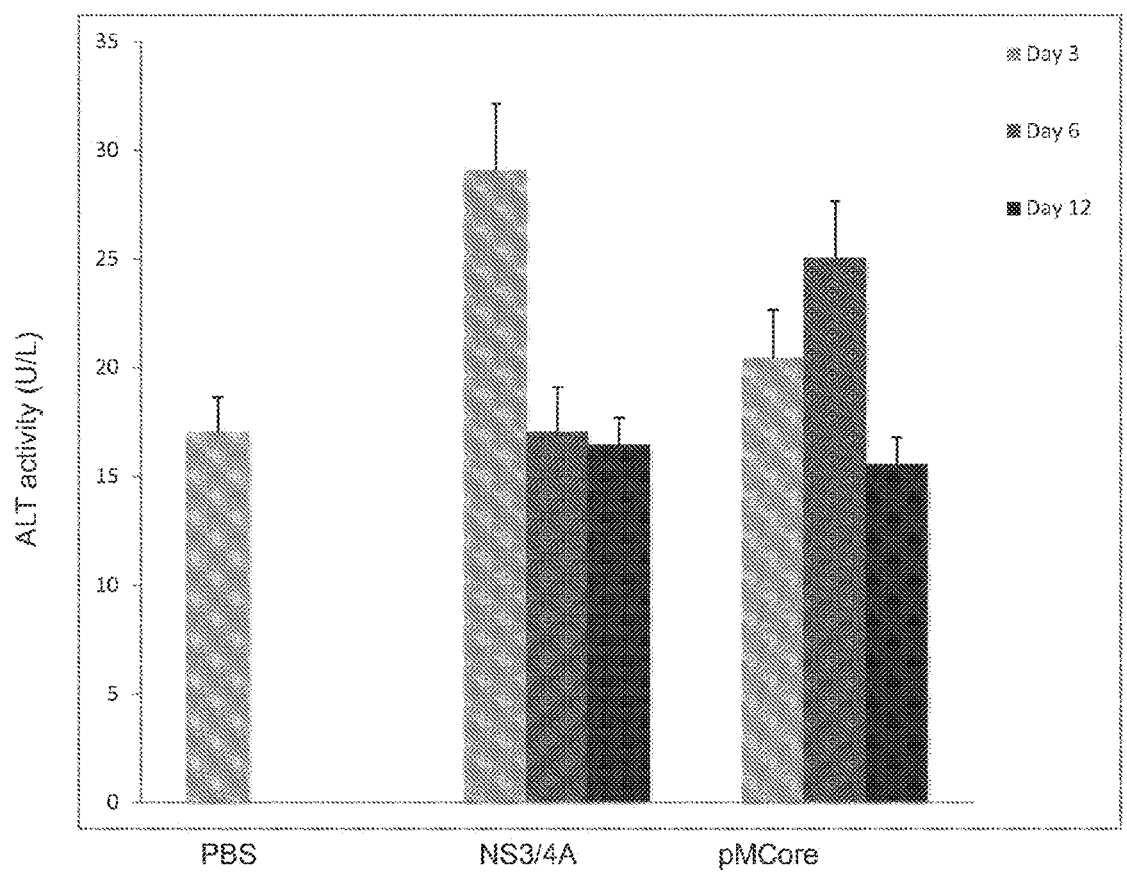
FIG. 41 shows data from experiments to determine if clearance induced by the immunized mice did effects liver by measuring ALT levels in sera.

In the absence of a small animal model for HBV, HBcAg was used to transiently transfect mouse liver through hydrodynamic injection. Immunized mice liver were either transfected with pMCore or HCV NS3/4A. Immunohistochemistry staining three days post transfection showed clearance of HBcAg-transfected hepatocytes as compared to the NS3/4A-transfected ones. ALT levels in sera were measured to ensure that the clearance induced by the immunized mice did not cause any liver damage. Results in FIG. 41 showed clearance induced by the immunized mice did not cause any liver damage.

Figure 42:
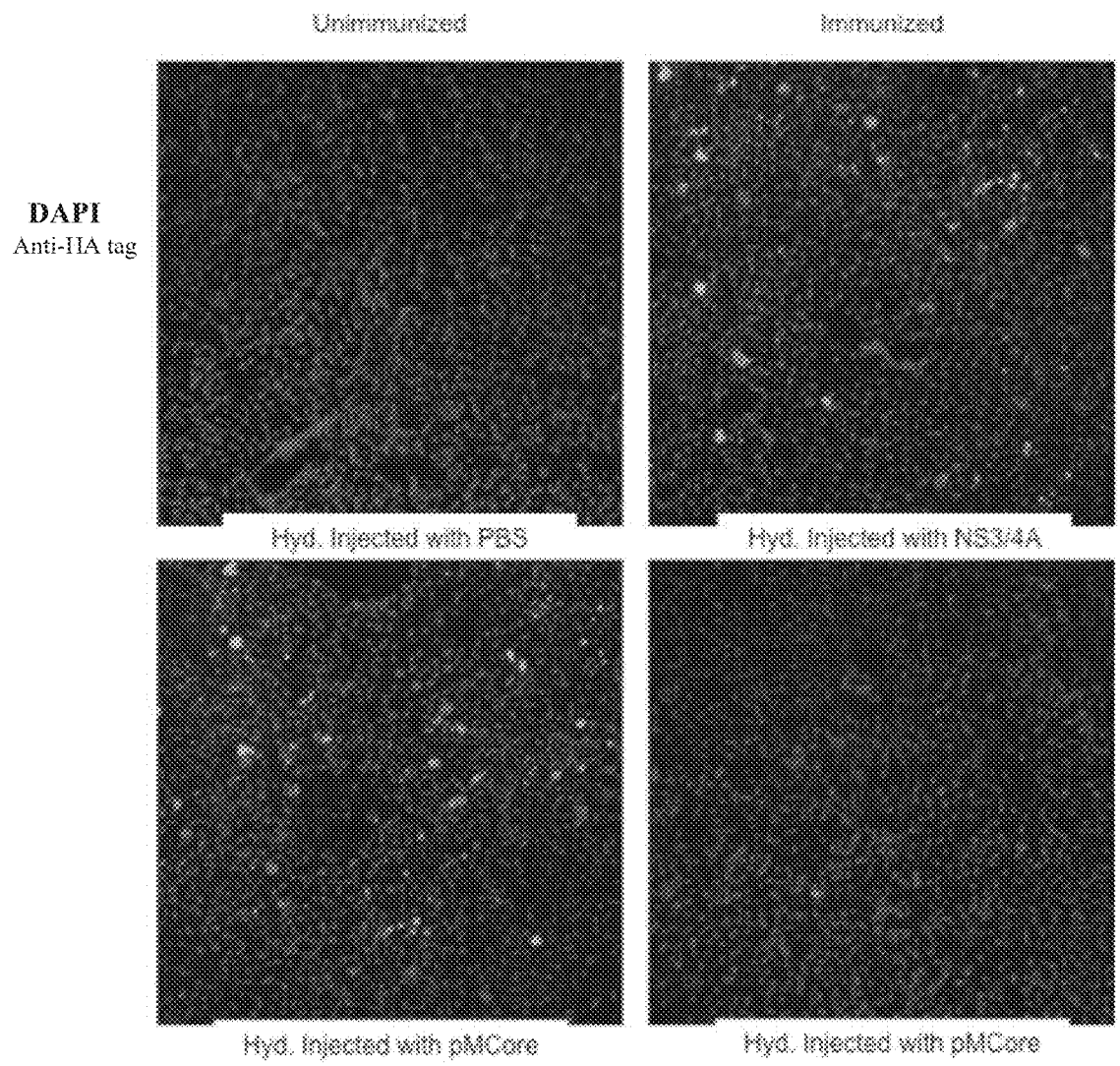
FIG. 42 shows immunostaining of liver sections taken three days after hydrodynamic injection of PBS, pMCore (HBcAg), or pNS3/4A (HCV NS3-4A) from naïve or mice that were immunized with pMcore is shown. Clearance is much higher for the pMCore-immunized liver as compared to the NS3/4a transfected control liver. PMcore or NS3/4A expression detected with an anti-HA antibody (white/light gray cells).
Figure 43:
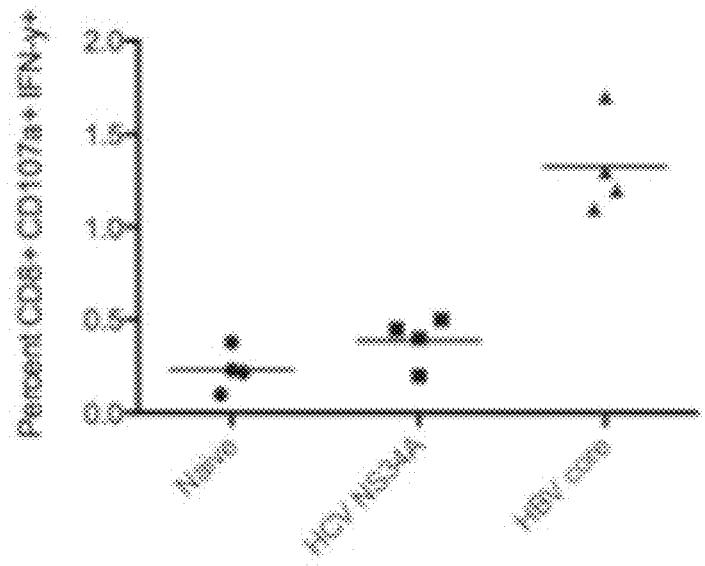
FIG. 43 shows 3 days post transfection, in which cells were analyzed for degranulation marker expression, CD107a, and IFN-γ+ expression following stimulation with HBcAg peptides.

Direct hydrodynamic injection was also used to transiently transfect mouse liver. Here, immunized or naive mouse livers were either transfected with pMCore or an irrelevant plasmid encoding hepatitis C antigens (HCV NS3/4A). Briefly, immunized mice were injected intravenously with 100 µg of plasmid in 2 mL (about 10% volume of the mouse weight) of Ringers solution within a period of 7 seconds to transiently transfect the liver. The expression or clearance of the plasmid was determined by staining the liver with anti-HA monoclonal antibodies. Immunohistochemistry staining three days post transfection (FIG. 42) showed clearance of HBcAg-transfected hepatocytes as compared to the NS3/4A-transfected animal livers. CD8 T cells isolated from the pMCore hydrodynamic injected mice in FIG. 43 showed a higher frequency of IFN-γ$^+$CD107a$^+$, a marker of degranulation, as compared to immunized animals livers transfected with the irrelevant plasmid.

Figure 44:
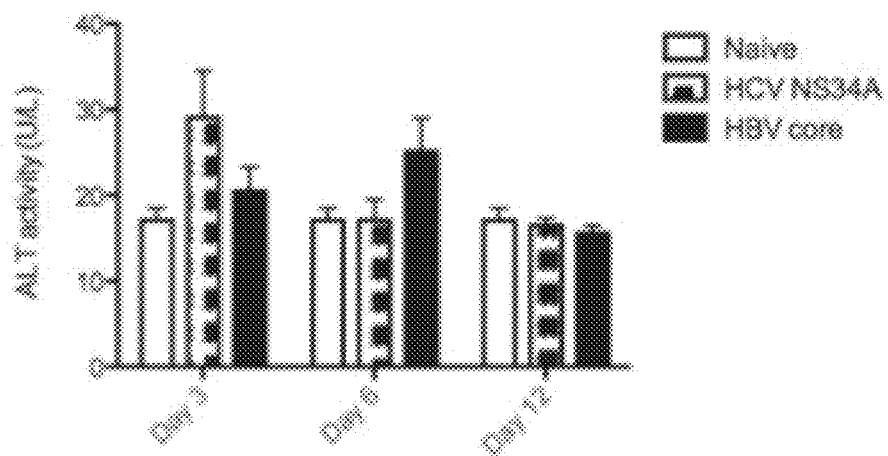
FIG. 44 shows serum ALT levels at day 3, 6, and 12 post transfection were measured and showed no evidence of elevation in relevant vaccinated animals.
Figure 45:
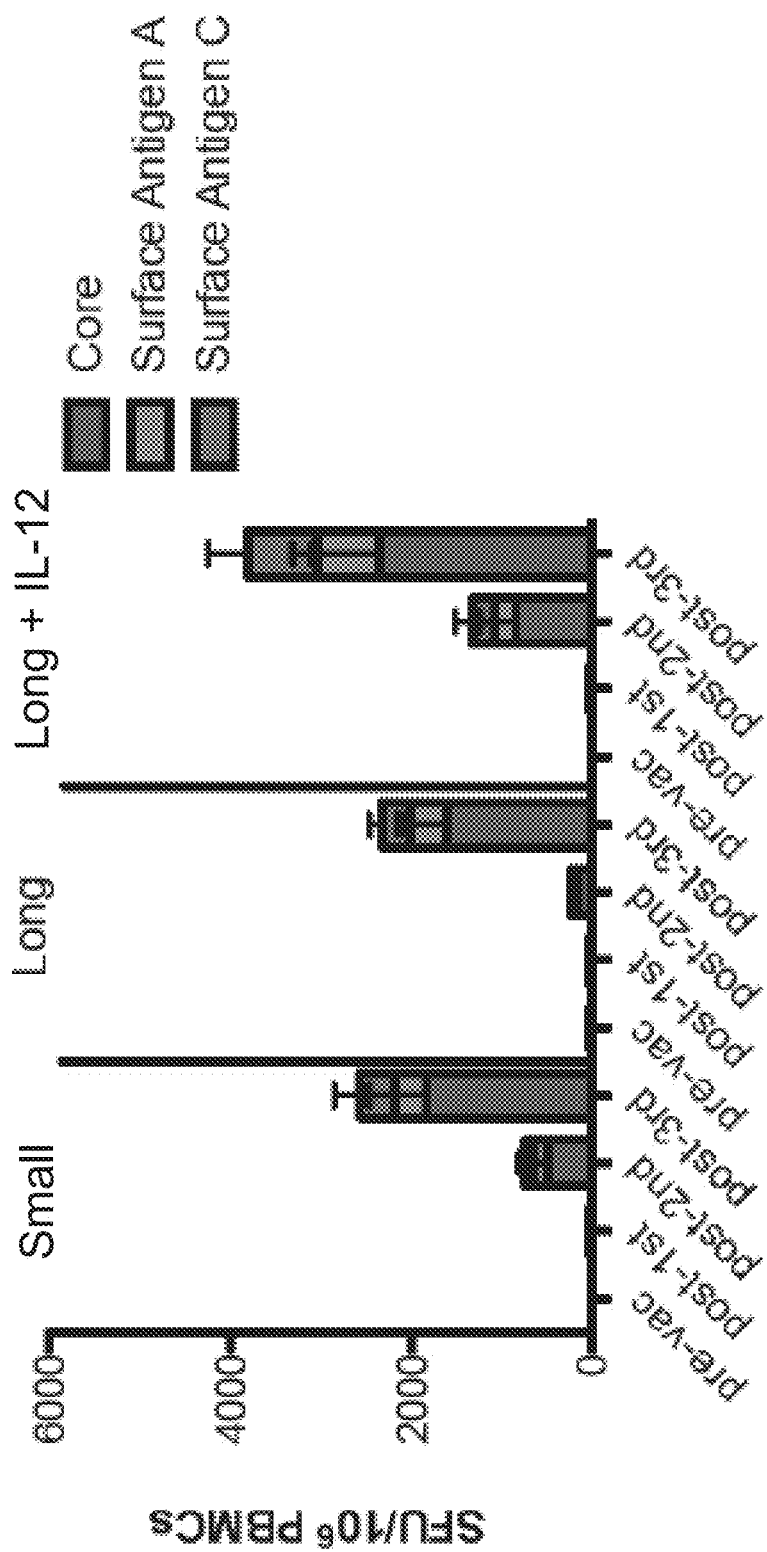
FIG. 45 shows data from ELISPOT assays.
Figure 46:
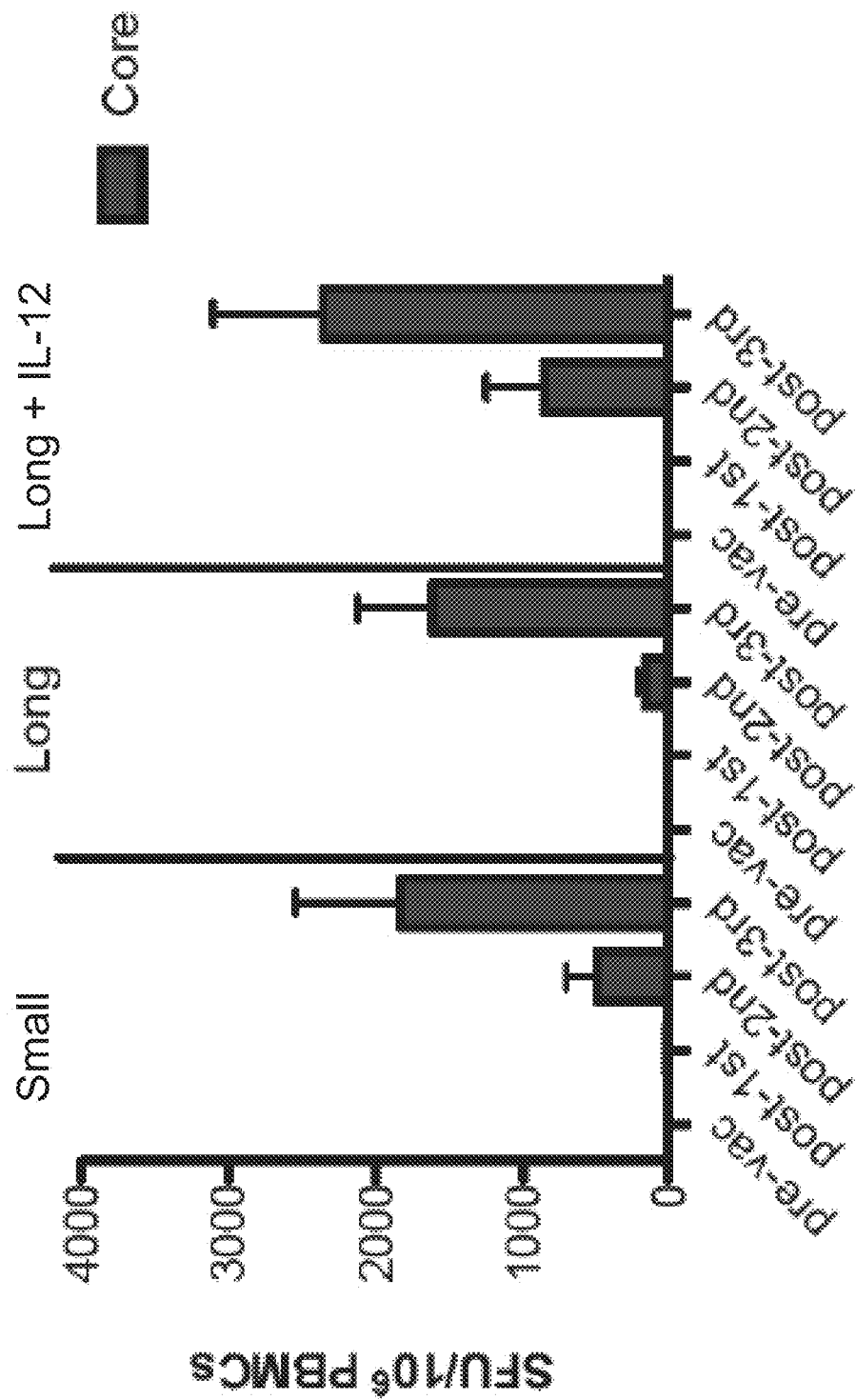
FIG. 46 shows data from ELISPOT assays.
Figure 47:
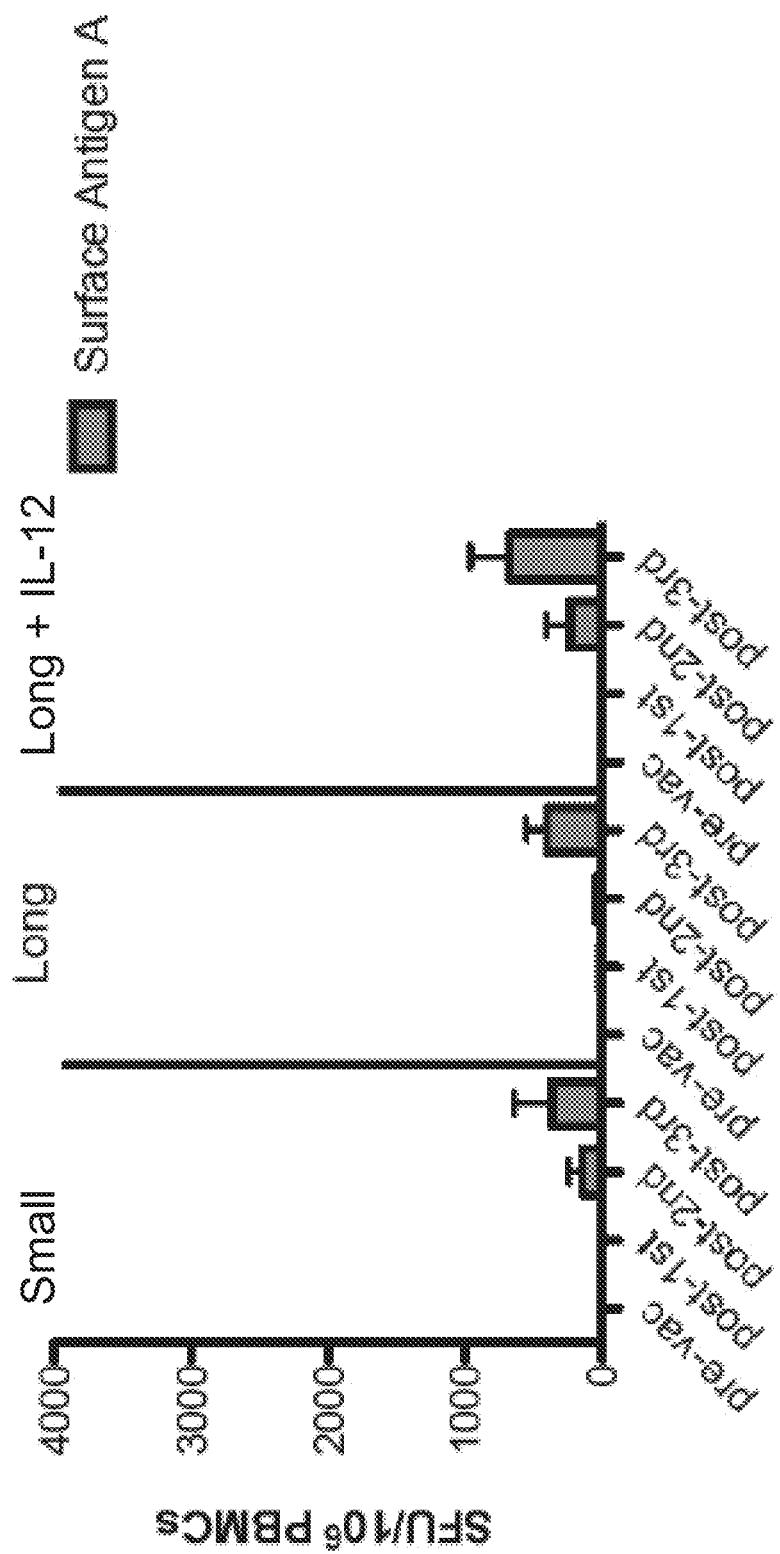
FIG. 47 shows data from ELISPOT assays.
Figure 48:
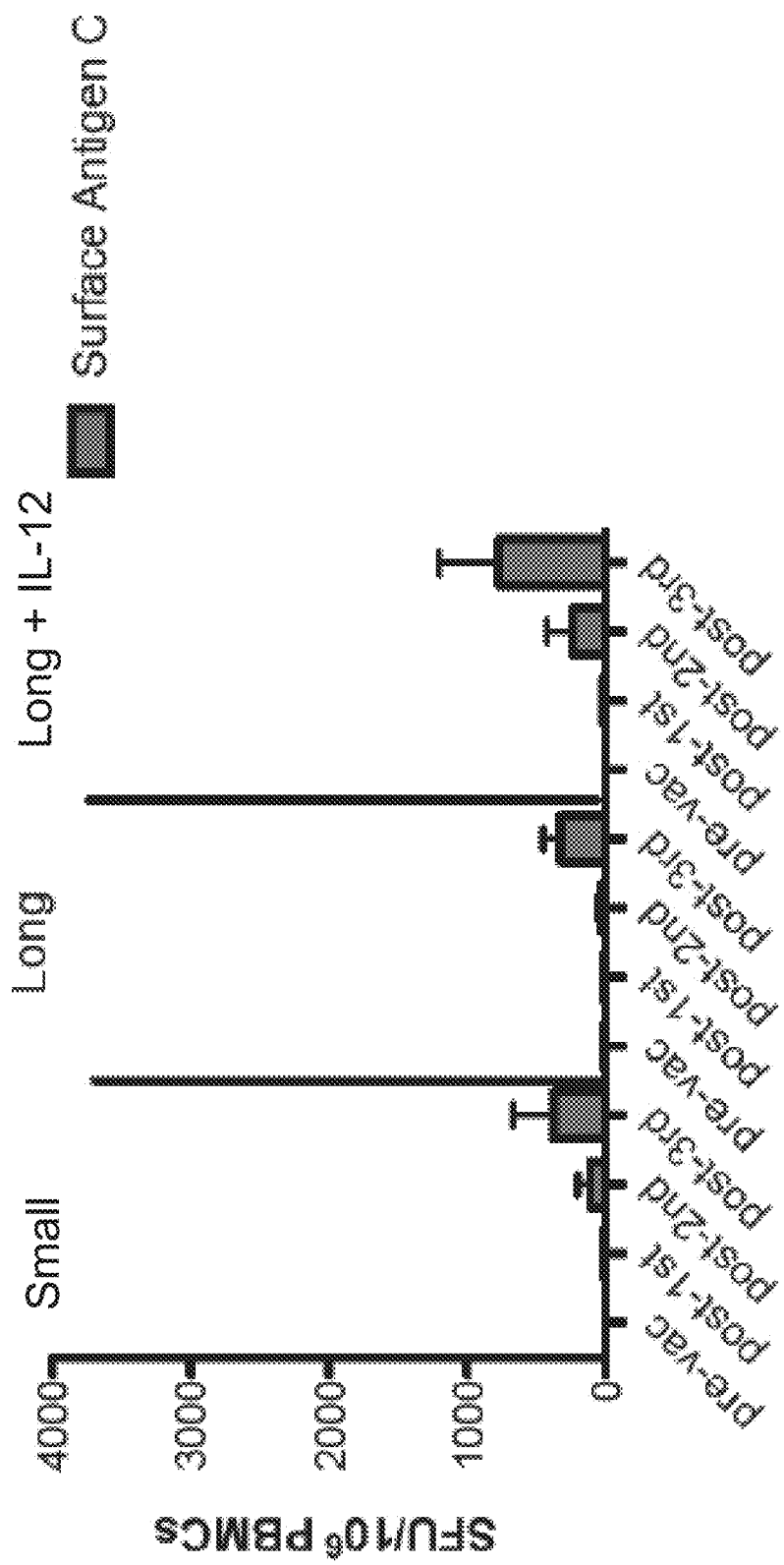
FIG. 48 shows data from ELISPOT assays.
Figure 49:
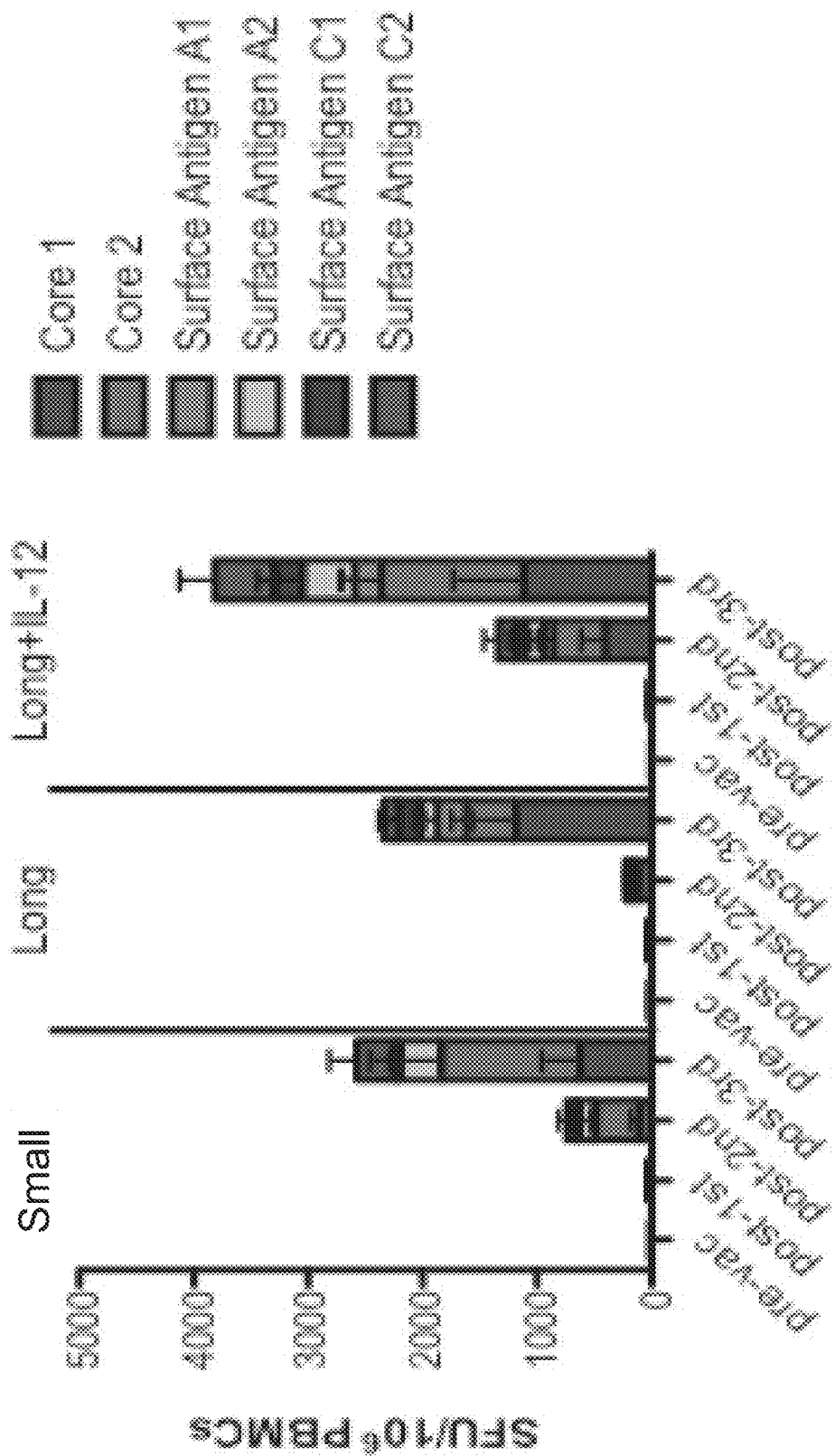
FIG. 49 shows data from ELISPOT assays.

Since the clearance of pMCore-transfected hepatocytes seems to involve degranulation, it was considered that the killing may lead to liver damage. To examine if immunized mice were able to clear the transfected hepatocytes without inducing significant liver damage, an assay measuring the activity of the enzyme alanine aminotransferase (ALT) was used to indicate the presence of liver damage when elevated enzyme levels were in the sera (FIG. 44). Particularly, serum alanine aminotransferase (ALT) activity was measured using an absorbance-based assay (Stanbio Laboratory) on a BioTek Synergy 2 microplate reader. Results are reported as units per liter (U/L) and represent the amount of enzyme that oxidizes one µmol/L of NADH per minute. These studies showed that the specific clearance of HBcAg-transfected hepatocytes did not increase ALT levels in transfected immunized animals beyond the normal range of 5-30U/L (FIG. 44).

Example 2

Consensus HBV surface proteins were designed from epitope sequences from primary isolates of HBV genotype A such that the resulting consensus protein had sequence identities of 94.2 percent to 99.8 percent with the surface proteins of HBV genotype A primary isolates. Particularly, two versions of such a consensus protein were designed (FIG. 4). One included the S protein and is also referred to as SHBs-A, in which SEQ ID NO:13 is the nucleic acid sequence and SEQ ID NO:14 is the amino acid sequence. The second included S protein, pre-S2, and pre-S1 and is also referred to as LHBs-A, in which SEQ ID NO:9 is the nucleic acid sequence and SEQ ID NO:10 is the amino acid sequence.

Consensus HBV surface proteins were also designed from epitope sequences from primary isolates of HBV genotype C such that the resulting consensus protein had sequence identities of 96.5 percent to 99.8 percent with the surface proteins of HBV genotype C primary isolates. Particularly, two versions of such a consensus protein were designed (FIG. 4). One included S protein and is also referred to as SHBs-C, in which SEQ ID NO:15 is the nucleic acid sequence and SEQ ID NO:16 is the amino acid sequence. The second included S protein, pre-S2, and pre-S 1 and is also referred to LHBs-C, in which SEQ ID NO:11 is the nucleic acid sequence and SEQ ID NO:12 is the amino acid sequence.

For the above consensus HBV surface antigens, endoproteolytic cleavage sites were introduced into the consensus HBV surface antigens to provide for proper protein folding and better CTL processing (FIG. 3). The codon usage in the consensus HBV surface antigens was modified to reflect the codon bias of human genes. Additionally, regions of very high (e.g., greater than 80 percent) or very low (e.g., less than 30 percent) GC content were avoided, as where cis-acting motifs such as internal TATA-boxes, repetitive sequences, and structured sequences. A Kozak sequence was introduced into the consensus HBV surface antigens to increase translational initiation and an IgE leader sequence was added to increase protein expression (FIG. 3).

The consensus HBV surface antigens SHBs-A, LHBs-A, SHBs-C, and LHBs-C were cloned into an expression vector to yield the constructs pSHb A, pLHb A, pSHb C, and pLHb C, respectively (FIG. 4).

Rhesus Macaques monkeys were placed in groups, in which each group had 5 monkeys. One group was administered via intramuscular (1M) delivery a vaccine including 1.0 mg of each of the constructs pMCore, pSHb A, and pSHb C; this group is referred to as the 'small' group. A second group was administered via IM delivery a vaccine including 1.0 mg of each of the constructs pMCore, pLHb A, and pLHb C; this group is referred to as the 'long' group. A third group was administered via IM delivery a vaccine including 1.0 mg of each of the constructs pMCore, pLHb A, and pLHb C, and 0.4 mg of prhIL-12; this group is referred to as the 'long+IL-12' group. The construct prhIL-12 encodes the Rhesus macaque IL-12 protein. Particularly, monkeys in the small, long, and long+IL-12 groups were immunized with the respective vaccines at week 0, week 4, and week 12. Samples were harvested from the monkeys prior to immunization at week 0 and also after each immunization (i.e., after weeks 0, 4, and 12).

FIGS. 45-48 show the cellular immune responses induced by vaccines administered to the small, long, and long+IL-12 groups. An enzyme-linked immunosorbent spot (ELISPOT) assay was utilized to determine the cellular immune responses as detailed above in Example 1. As depicted in FIGS. 45-48, the T-cell response was boosted with each vaccination. However, the HBV core antigen was more immunogenic than HBV surface antigen A and HBV surface antigen C. The data also demonstrates that longer consensus HBV surface antigen (i.e., includes S protein, pre-S2, and pre-S1) is as immunogenic as the smaller consensus HBV surface antigen (i.e., includes S protein).

Similar to FIGS. 45-48, FIG. 49 shows the cellular immune responses induced by vaccines administered to the small, long, and long+IL-12 groups as measured by the ELISPOT assay, however, different pools of peptides covering the core antigen, surface antigen A, and surface antigen C were examined Again, the T-cell response was boosted with each vaccination, the addition of IL-12 enhanced the cellular immune response, and the long and short consensus HBV surface antigens were similarly immunogenic.

Figure 50:
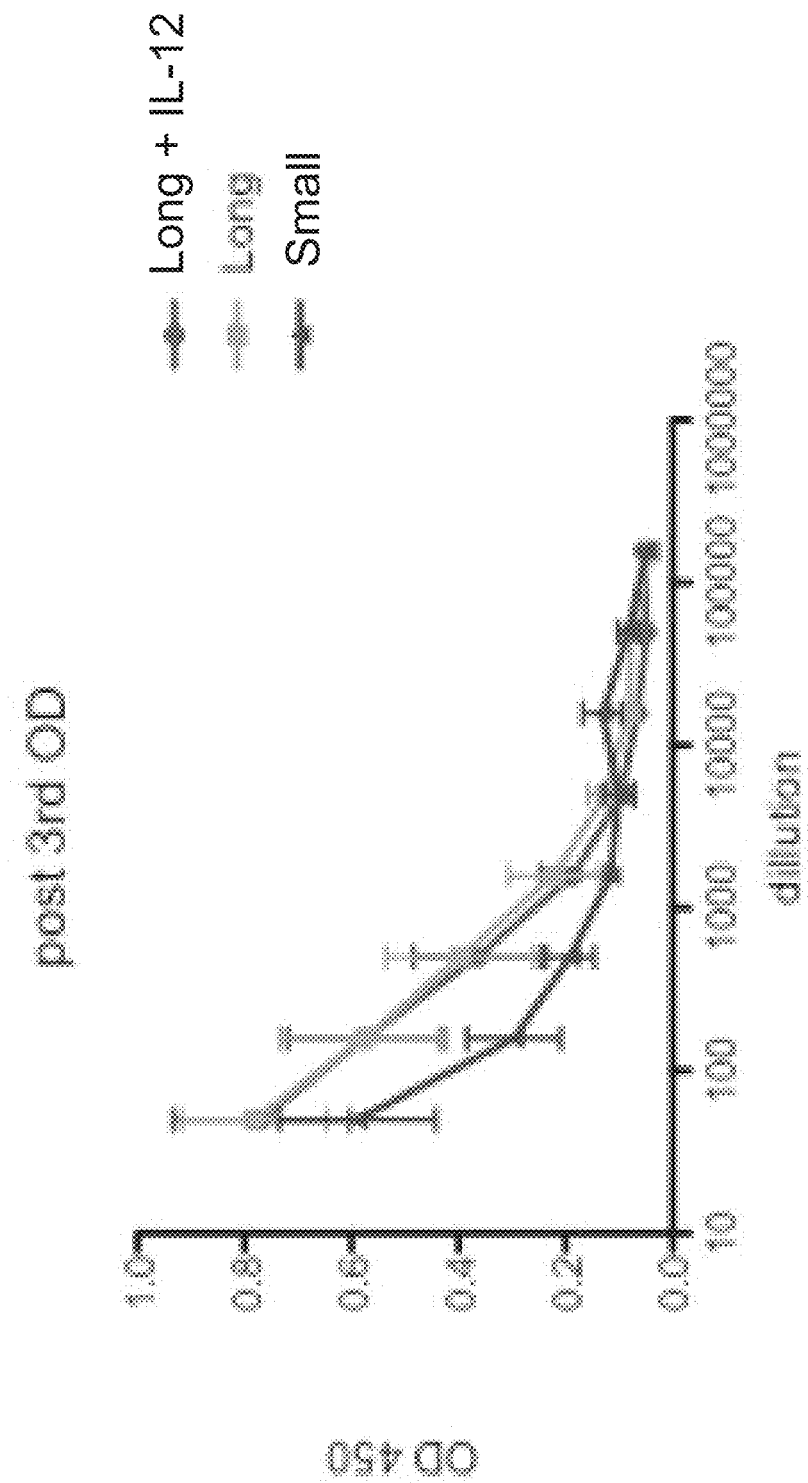
FIG. 50 shows a comparison of anti-HBV antibodies in serial dilution of sera from animals immunized with the small (i.e., pMCore, pSHb A, and pSHb C), long (i.e., pMCore, pLHb A, and pLHb C), and long+IL-12 (i.e., pMCore, pLHb A, pLHb C, and prlIL-12) vaccines.

FIG. 50 shows ELISA data comparing anti-HBV antibody responses for the small, long, and long+IL-12 groups. ELISA's were performed as detailed above in Example 1. Antigen-specific humoral responses in sera collected from the immunized monkeys were observed. Particularly, the vaccines including the long consensus surface antigen (i.e., S protein, pre-S2, and pre-S1 has a better antibody response, which can be due to the extra epitopes present in the vaccine.

Figure 51:
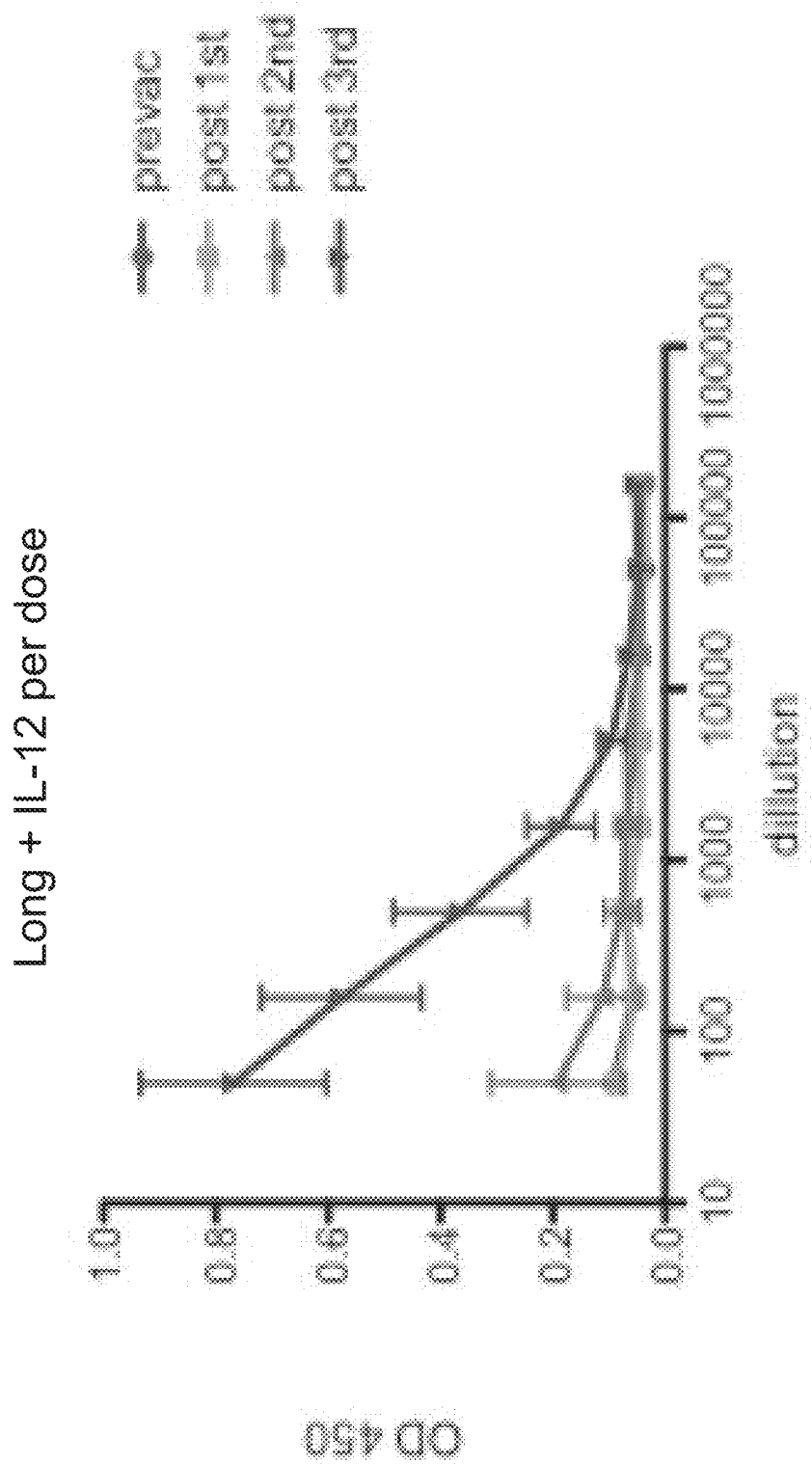
FIG. 51 shows a comparison of anti-HBV antibodies in serial dilution from animals immunized with the long+IL-12 (i.e., pMcore, pHHb A, pLHb C, and prlIL-12) vaccine.

FIG. 51 shows ELISA data comparing anti-HBV antibody responses for the long+IL-12 group prior to immunization (prevac) and after immunization at week 0, week 4, and week 12 (i.e., post 1$^{st}$, post 2$^{nd}$, and post 3$^{rd}$, respectively). ELISAs were performed as described above in Example 1. The data in FIG. 51 demonstrated that 2 immunizations or doses are required for measurable antibody production. Furthermore, a significant boost in the anti-HBV antibody response was observed after the third immunization or dose.

Example 3

Similar to the experiments with mice in Example 2, splenocytes will be isolated from the immunized Rhesus monkeys of Example 2 to examine the levels of INF-γ and TNF-α secretion in response to administration of the combination of consensus core and consensus surface antigens. It will be determined if the CD8 and CD4 T cells of the immunized monkeys from Example 2 have similar characteristics as the mouse CD8 and CD4 T cells studied in Example 1.

CD8 and CD4 T-cells will be taken from the spleens of the Rhesus monkeys of Example 2. The CD8 and CD4 T-cells will be studied via polyfunctional and phenotypic flow analysis to examine the secretion of tumor necrosis factor, interferon gamma, and CD107a from these CD8 and CD4 T-cells.

The Rhesus monkeys of Example 2 will be used in a post-vaccination killing assay.

The invention claimed is:

1. An immunogenic composition comprising:
   (a) a nucleic acid molecule encoding one or more proteins selected from the group consisting of: SEQ ID NO:10 and a protein that is 95% identical to the full length amino acid sequence of SEQ ID NO:10; or
   (b) a nucleic acid molecule encoding one or more proteins selected from the group consisting of: SEQ ID NO: 12 and a protein that is 95% identical to the full length amino acid sequence of SEQ ID NO:12.

2. The immunogenic composition of claim 1, further comprising:
   (c) a nucleic acid molecule encoding SEQ ID NO:2.

3. The immunogenic composition of claim 1, comprising:
   (a) a nucleic acid molecule encoding one or more proteins selected from the group consisting of: SEQ ID NO:10 and a protein that is 95% identical to the full length amino acid sequence of SEQ ID NO:10;
   (b) a nucleic acid molecule encoding one or more proteins selected from the group consisting of: SEQ ID NO: 12 and a protein that is 95% identical to the full length amino acid sequence of SEQ ID NO:12; and
   (c) a nucleic acid molecule encoding SEQ ID NO:2.

4. The immunogenic composition of claim 3, wherein the nucleic acid molecules comprise one or more nucleotide sequences selected from the group consisting of: SEQ ID NO:1, SEQ ID NO:3, SEQ ID NO:5, SEQ ID NO:9, and SEQ ID NO:11.

5. The immunogenic composition of claim 1, wherein the nucleic acid molecules are plasmids.

6. The immunogenic composition of claim 1, wherein the nucleic acid molecules are incorporated into viral particles.

7. The immunogenic composition of claim 1 further comprising an adjuvant molecule.

8. The immunogenic composition of claim 7, wherein the adjuvant is IL-12, IL-15, IL-28, or RANTES.

9. A method of inducing an immune response against an HBV antigen comprising administering the immunogenic composition of claim 1 to a subject.

* * * * *

SEQUENCE LISTING

```
<160> NUMBER OF SEQ ID NOS: 21

<210> SEQ ID NO 1
<211> LENGTH: 552
<212> TYPE: DNA
<213> ORGANISM: Artificial Sequence
<220> FEATURE:
<223> OTHER INFORMATION: nucleic acid sequence M-core
<220> FEATURE:
<221> NAME/KEY: misc_feature
<222> LOCATION: (1)..(3)
<223> OTHER INFORMATION: n is a, c, g, or t

<400> SEQUENCE: 1
nnngacatcg acccctacaa agaattcggc gccaccgtgg aactgctgag cttcctgccc      60
agcgacttct tcccctccgt gcgggacctg ctggataccg ccagcgccct gtacagagag     120
gccctggaaa gccccgagca ctgcagccct caccacacag ccctgcggca ggccatcctg     180
tgctggggcg agctgatgac cctggccacc tgggtcggaa gcaacctgga agatcccgcc     240
agccgggacc tggtggtgtc ctacgtgaac accaacatgg gcctgaagat ccggcagctg     300
ctgtggttcc acatctcctg cctgaccttc ggccgggaaa ccgtgctgga atacctggtg     360
tccttcggcg tgtggatcag aacccccccct gcctacagac cccccaacgc ccctatcctg     420
agcaccctgc ccgagacaac cgtggtccgc agacggggca gaagcccag aagaagaacc      480 cccagcccta gacggcggag atctcagagc cccaggcgga gaagatccca gagccgcgag     540
agccagtgct ga                                                        552

<210> SEQ ID NO 2
<211> LENGTH: 183
<212> TYPE: PRT
<213> ORGANISM: Artificial Sequence
<220> FEATURE:
<223> OTHER INFORMATION: Amino Acid Sequence of M-Core
<220> FEATURE:
<221> NAME/KEY: MISC_FEATURE
<222> LOCATION: (1)..(1)
<223> OTHER INFORMATION: Xaa can be any naturally occurring amino acid

<400> SEQUENCE: 2

Xaa Asp Ile Asp Pro Tyr Lys Glu Phe Gly Ala Thr Val Glu Leu Leu
  1               5                  10                  15

Ser Phe Leu Pro Ser Asp Phe Phe Pro Ser Val Arg Asp Leu Leu Asp
                 20                  25                  30

Thr Ala Ser Ala Leu Tyr Arg Glu Ala Leu Glu Ser Pro Glu His Cys
             35                  40                  45

Ser Pro His His Thr Ala Leu Arg Gln Ala Ile Leu Cys Trp Gly Glu
         50                  55                  60
```

```
Leu Met Thr Leu Ala Thr Trp Val Gly Ser Asn Leu Glu Asp Pro Ala
 65                  70                  75                  80

Ser Arg Asp Leu Val Val Ser Tyr Val Asn Thr Asn Met Gly Leu Lys
                 85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Asn Ala Pro Ile Leu Ser Thr Leu Pro
    130                 135                 140

Glu Thr Thr Val Val Arg Arg Gly Arg Ser Pro Arg Arg Thr
145                 150                 155                 160

Pro Ser Pro Arg Arg Arg Ser Gln Ser Pro Arg Arg Arg Ser
                165                 170                 175

Gln Ser Arg Glu Ser Gln Cys
            180
```

```
<210> SEQ ID NO 3
<211> LENGTH: 603
<212> TYPE: DNA
<213> ORGANISM: Artificial Sequence
<220> FEATURE:
<223> OTHER INFORMATION: nucleic acid sequence IgE leader - M-Core

<400> SEQUENCE: 3
atggactgga cctggattct gttcctggtg ccgctgcca caagggtgca cagcgacatc      60
gaccctaca aagaattcgg cgccaccgtg aactgctga gcttcctgcc cagcgacttc     120
ttcccctccg tgcgggacct gctggatacc gccagcgccc tgtacagaga ggccctggaa   180
agccccgagc actgcagccc tcaccacaca gccctgcggc aggccatcct gtgctggggc   240
gagctgatga ccctggccac ctgggtcgga agcaacctgg aagatcccgc cagccgggac   300
ctggtggtgt cctacgtgaa caccaacatg ggcctgaaga tccggcagct gctgtggttc   360
cacatctcct gcctgacctt cggccgggaa accgtgctgg aatacctggt gtccttcggc   420
gtgtggatca gaaccccccc tgcctacaga cccccaacg cccctatcct gagcaccctg    480
cccgagacaa ccgtggtccg cagacggggc agaagcccca agaagaac ccccagccct     540
agacggcgga gatctcagag ccccaggcgg agaagatccc agagccgcga gagccagtgc   600
tga                                                                   603
```

```
<210> SEQ ID NO 4
<211> LENGTH: 200
<212> TYPE: PRT
<213> ORGANISM: Artificial Sequence
<220> FEATURE:
<223> OTHER INFORMATION: Amino Acid Sequence of IgE leader - M-Core

<400> SEQUENCE: 4

Met Asp Trp Thr Trp Ile Leu Phe Leu Val Ala Ala Thr Arg Val
  1               5                  10                  15

His Ser Asp Ile Asp Pro Tyr Lys Glu Phe Gly Ala Thr Val Glu Leu
             20                  25                  30

Leu Ser Phe Leu Pro Ser Asp Phe Pro Ser Val Arg Asp Leu Leu
         35                  40                  45

Asp Thr Ala Ser Ala Leu Tyr Arg Glu Ala Leu Glu Ser Pro Glu His
 50                  55                  60

Cys Ser Pro His His Thr Ala Leu Arg Gln Ala Ile Leu Cys Trp Gly
```

```
                65                  70                  75                  80
Glu Leu Met Thr Leu Ala Thr Trp Val Gly Ser Asn Leu Glu Asp Pro
                            85                  90                  95
Ala Ser Arg Asp Leu Val Val Ser Tyr Val Asn Thr Asn Met Gly Leu
                100                 105                 110
Lys Ile Arg Gln Leu Leu Trp Phe His Ile Ser Cys Leu Thr Phe Gly
                115                 120                 125
Arg Glu Thr Val Leu Gly Tyr Leu Val Ser Phe Gly Val Trp Ile Arg
        130                 135                 140
Thr Pro Pro Ala Tyr Arg Pro Pro Asn Ala Pro Ile Leu Ser Thr Leu
145                 150                 155                 160
Pro Glu Thr Thr Val Val Arg Arg Arg Gly Arg Ser Pro Arg Arg Arg
                    165                 170                 175
Thr Pro Ser Pro Arg Arg Arg Ser Gln Ser Pro Arg Arg Arg
        180                 185                 190
Ser Gln Ser Arg Glu Ser Gln Cys
            195                 200

<210> SEQ ID NO 5
<211> LENGTH: 630
<212> TYPE: DNA
<213> ORGANISM: Artificial Sequence
<220> FEATURE:
<223> OTHER INFORMATION: nucleic acid sequence IgE leader - M-Core + HA
      Tag

<400> SEQUENCE: 5
atggactgga cctggattct gttcctggtg gccgctgcca caagggtgca cagcgacatc       60
gaccc ctaca aagaattcgg cgccaccgtg gaactgctga gcttcctgcc cagcgacttc     120
ttcccctccg tgcgggacct gctggatacc gccagcgccc tgtacagaga ggccctggaa     180
agccccgagc actgcagccc tcaccacaca gccctgcggc aggccatcct gtgctggggc     240
gagctgatga ccctggccac ctgggtcgga agcaacctgg aagatcccgc cagccgggac     300
ctggtggtgt cctacgtgaa caccaacatg ggcctgaaga tccggcagct gctgtggttc     360
cacatctcct gcctgacctt cggccgggaa accgtgctgg aatacctggt gtccttcggc     420
gtgtggatca gaaccccccc tgcctacaga ccccccaacg cccctatcct gagcaccctg     480
cccgagacaa ccgtggtccg cagacggggc agaagcccca agaagaac cccagcccct       540
agacggcgga gatctcagag ccccaggcgg agaagatccc agagccgcga gagccagtgc     600
taccectacg acgtgcccga ctacgcctga                                       630

<210> SEQ ID NO 6
<211> LENGTH: 209
<212> TYPE: PRT
<213> ORGANISM: Artificial Sequence
<220> FEATURE:
<223> OTHER INFORMATION: Amino Acid Sequence of IgE leader - M-Core + HA
      Tag

<400> SEQUENCE: 6

Met Asp Trp Thr Trp Ile Leu Phe Leu Val Ala Ala Thr Arg Val
1               5                   10                  15

His Ser Asp Ile Asp Pro Tyr Lys Glu Phe Gly Ala Thr Val Glu Leu
                20                  25                  30

Leu Ser Phe Leu Pro Ser Asp Phe Pro Ser Val Arg Asp Leu Leu
            35                  40                  45
```

```
Asp Thr Ala Ser Ala Leu Tyr Arg Glu Ala Leu Glu Ser Pro Glu His
        50                  55                  60

Cys Ser Pro His His Thr Ala Leu Arg Gln Ala Ile Leu Cys Trp Gly
 65                  70                  75                  80

Glu Leu Met Thr Leu Ala Thr Trp Val Gly Ser Asn Leu Glu Asp Pro
                85                  90                  95

Ala Ser Arg Asp Leu Val Val Ser Tyr Val Asn Thr Asn Met Gly Leu
                100                 105                 110

Lys Ile Arg Gln Leu Leu Trp Phe His Ile Ser Cys Leu Thr Phe Gly
                115                 120                 125

Arg Glu Thr Val Leu Gly Tyr Leu Val Ser Phe Gly Val Trp Ile Arg
        130                 135                 140

Thr Pro Pro Ala Tyr Arg Pro Pro Asn Ala Pro Ile Leu Ser Thr Leu
145                 150                 155                 160

Pro Glu Thr Thr Val Val Arg Arg Arg Gly Arg Ser Pro Arg Arg Arg
                165                 170                 175

Thr Pro Ser Pro Arg Arg Arg Ser Gln Ser Pro Arg Arg Arg
                180                 185                 190

Ser Gln Ser Arg Glu Ser Gln Cys Tyr Pro Tyr Asp Val Pro Asp Tyr
        195                 200                 205

Ala

<210> SEQ ID NO 7
<211> LENGTH: 18
<212> TYPE: PRT
<213> ORGANISM: Artificial Sequence
<220> FEATURE:
<223> OTHER INFORMATION: IgE leader amino acid sequence

<400> SEQUENCE: 7

Met Asp Trp Thr Trp Ile Leu Phe Leu Val Ala Ala Thr Arg Val
1               5                   10                  15

His Ser

<210> SEQ ID NO 8
<211> LENGTH: 9
<212> TYPE: PRT
<213> ORGANISM: Artificial Sequence
<220> FEATURE:
<223> OTHER INFORMATION: HA Tag amino acid sequence

<400> SEQUENCE: 8

Tyr Pro Tyr Asp Val Pro Asp Tyr Ala
1               5

<210> SEQ ID NO 9
<211> LENGTH: 1317
<212> TYPE: DNA
<213> ORGANISM: Artificial Sequence
<220> FEATURE:
<223> OTHER INFORMATION: Synthetic (LHBs-A)

<400> SEQUENCE: 9
ggatccgcca ccatggattg gacttggatt ctgttcctgg tcgccgctgc tacacgggtg      60
cattcagggg gctggtcttc aaaacctaga aaaggcatgg gcaccaacct gagcgtgccc     120
aatcctctgg ggttctttcc agaccaccag ctggaccccg ctttcggcgc aaactccaac     180
aatcctgact gggacttcaa cccaatcaaa gaccactggc cagcagctaa ccaagtggga    240
gtcggagctt tcggaccagg actgactccc cctcatggcg ggattctggg ctggtctccc    300
```

```
caggctcagg gcatcctgac cacagtgagc actattccac ccctgcaag caccaacagg     360 cagtccggac gccagccaac cccaatctca ccaccctgc agacagcca ccctcaggcc     420 agaggcagga acggagatc tatgcagtgg aatagtacag ccttccatca ggctctgcag     480 gaccccggg tgcggggact gtactttcca gccggaggca gctcctctgg cactgtcaac     540
cctgcaccaa atatcgcctc ccacatcagt tcaatttctg ctcgaactgg agaccccgtg     600
accaaccggg gcagaaagag gcgcagtatg gagaatatta cctcagggtt cctgggacct     660
ctgctggtcc tgcaggcagg cttctttctg ctgacccgca tcctgacaat tcctcagtca     720
ctggatagct ggtggaccag cctgaacttc ctgggcggca gccccgtgtg cctgggacag     780
aactctcaga gtcctacctc caatcattct ccaacaagtt gtcctccaat ctgcccaggc     840
tacagatgga tgtgcctgcg acggttcatc attttcctgt ttatcctgct gctgtgcctg     900
atttttctgc tggtgctgct ggactatcag gcatgctgc cagtctgccc cctgattcct     960
gggtccacta ccacatctac aggacccctgt aagacttgca ctaccctgc caggggaac    1020 agtatgtttc catcatgctg ttgcacaaaa cccactgatg gaaattgtac atgcatcccc    1080
attcctagct cctgggcatt cgccaagtat ctgtgggaat gggcaagcgt gaggttttca    1140
tggctgagcc tgctggtgcc cttcgtccag tggtttgtgg gactgagccc taccgtctgg    1200
ctgtccgcca tctggatgat gtggtactgg gggcccagcc tgtattcaat cgtgtctcca    1260
ttcatccccc tgctgccaat cttctttttgt ctgtgggtct acatttgata actcgag      1317
```

<210> SEQ ID NO 10
<211> LENGTH: 431
<212> TYPE: PRT
<213> ORGANISM: Artificial Sequence
<220> FEATURE:
<223> OTHER INFORMATION: Synthetic (LHBs-A)

<400> SEQUENCE: 10

```
Met Asp Trp Thr Trp Ile Leu Phe Leu Val Ala Ala Thr Arg Val
 1               5                  10                  15

His Ser Gly Gly Trp Ser Ser Lys Pro Arg Lys Gly Met Gly Thr Asn
                20                  25                  30

Leu Ser Val Pro Asn Pro Leu Gly Phe Phe Pro Asp His Gln Leu Asp
            35                  40                  45

Pro Ala Phe Gly Ala Asn Ser Asn Asn Pro Asp Trp Asp Phe Asn Pro
        50                  55                  60

Ile Lys Asp His Trp Pro Ala Ala Asn Gln Val Gly Val Gly Ala Phe
 65                  70                  75                  80

Gly Pro Gly Leu Thr Pro Pro His Gly Gly Ile Leu Gly Trp Ser Pro
                85                  90                  95

Gln Ala Gln Gly Ile Leu Thr Thr Val Ser Thr Ile Pro Pro Pro Ala
            100                 105                 110

Ser Thr Asn Arg Gln Ser Gly Arg Gln Pro Thr Pro Ile Ser Pro Pro
        115                 120                 125

Leu Arg Asp Ser His Pro Gln Ala Arg Gly Arg Lys Arg Arg Ser Met
    130                 135                 140

Gln Trp Asn Ser Thr Ala Phe His Gln Ala Leu Gln Asp Pro Arg Val
145                 150                 155                 160

Arg Gly Leu Tyr Phe Pro Ala Gly Gly Ser Ser Ser Gly Thr Val Asn
                165                 170                 175

Pro Ala Pro Asn Ile Ala Ser His Ile Ser Ser Ile Ser Ala Arg Thr
```

```
                180                 185                 190
Gly Asp Pro Val Thr Asn Arg Gly Arg Lys Arg Ser Met Glu Asn
                195                 200                 205

Ile Thr Ser Gly Phe Leu Gly Pro Leu Leu Val Leu Gln Ala Gly Phe
                210                 215                 220

Phe Leu Leu Thr Arg Ile Leu Thr Ile Pro Gln Ser Leu Asp Ser Trp
225                 230                 235                 240

Trp Thr Ser Leu Asn Phe Leu Gly Gly Ser Pro Val Cys Leu Gly Gln
                245                 250                 255

Asn Ser Gln Ser Pro Thr Ser Asn His Ser Pro Thr Ser Cys Pro Pro
                260                 265                 270

Ile Cys Pro Gly Tyr Arg Trp Met Cys Leu Arg Arg Phe Ile Ile Phe
                275                 280                 285

Leu Phe Ile Leu Leu Leu Cys Leu Ile Phe Leu Leu Val Leu Leu Asp
                290                 295                 300

Tyr Gln Gly Met Leu Pro Val Cys Pro Leu Ile Pro Gly Ser Thr Thr
305                 310                 315                 320

Thr Ser Thr Gly Pro Cys Lys Thr Cys Thr Thr Pro Ala Gln Gly Asn
                325                 330                 335

Ser Met Phe Pro Ser Cys Cys Cys Thr Lys Pro Thr Asp Gly Asn Cys
                340                 345                 350

Thr Cys Ile Pro Ile Pro Ser Ser Trp Ala Phe Ala Lys Tyr Leu Trp
                355                 360                 365

Glu Trp Ala Ser Val Arg Phe Ser Trp Leu Ser Leu Leu Val Pro Phe
                370                 375                 380

Val Gln Trp Phe Val Gly Leu Ser Pro Thr Val Trp Leu Ser Ala Ile
385                 390                 395                 400

Trp Met Met Trp Tyr Trp Gly Pro Ser Leu Tyr Ser Ile Val Ser Pro
                405                 410                 415

Phe Ile Pro Leu Leu Pro Ile Phe Phe Cys Leu Trp Val Tyr Ile
                420                 425                 430

<210> SEQ ID NO 11
<211> LENGTH: 1319
<212> TYPE: DNA
<213> ORGANISM: Artificial Sequence
<220> FEATURE:
<223> OTHER INFORMATION: Synthetic (LHBs-C)

<400> SEQUENCE: 11
gaattcgcca ccatggattg acatggatt  ctgtttctgg tcgccgccgc aacccgcgtg      60
cactcagggg gatggtcatc aaaacctaga cagggaatgg gcactaacct gagtgtgccc     120
aatcctctgg ggttctttcc cgaccaccag ctggatcctg ccttcggcgc taactctaac     180
aatccagact gggacttcaa ccccaataag gaccactggc ctgaggcaaa tcaagtggga     240
gcaggagcct tcggaccagg ctttacaccc cctcatggcg gactgctggg atggtccccct     300 caggctcagg ggatcctgac cacagtccca gcagctccac cccctgcaag tactaacagg     360
cagtcaggac gccagccaac ccccatttct ccacccctga gggacagtca ccctcaggcc     420
agaggcagga agcggagaag catgcagtgg aacagcacta ccttccatca ggcactgctg     480
gatccacgcg tgcgaggact gtactttcca gccggaggca gctcctctgg aaccgtgaac     540
cctgtcccaa caactgcctc cccaatcagt tcaattttct ctcggacagg agaccccgct     600
cctaatcggg gcagaaaaag gcgctcaatg gaaagcacca catccgggtt tctgggacca     660
```

```
ctgctggtgc tgcaggcagg cttctttctg ctgaccagaa tcctgacaat tccccagtct    720
ctggatagtt ggtggaccag cctgaacttc ctgggcggcg ccctacttg tccaggacag     780 aactctcaga gtccaacatc aaatcatagc cccacttcct gtcctccaat ctgccctggc    840
taccgctgga tgtgcctgcg acggttcatc attttcctgt ttatcctgct gctgtgcctg    900
atttttctgc tggtgctgct ggactatcag ggaatgctgc ccgtctgccc tctgctgcca    960
gggacttcta ctaccagtac cggaccttgt aagacatgca ctattccagc tcaggggacc   1020
tccatgttcc cctcttgctg ttgcaccaaa cctagcgatg gaaattgtac atgcatccca   1080
attcccagct cctgggcttt cgcacgattt ctgtgggagt gggccagcgt gcgcttttca   1140
tggctgagcc tgctggtgcc cttcgtccag tggtttgtcg gcctgtcacc taccgtgtgg   1200
ctgagcgtca tctggatgat gtggtactgg gggcccagcc tgtataatat cctgtcacca   1260
ttcctgccac tgctgccaat cttctttttgt ctgtgggtct acatttgata agcggccgc   1319
```

<210> SEQ ID NO 12
<211> LENGTH: 431
<212> TYPE: PRT
<213> ORGANISM: Artificial Sequence
<220> FEATURE:
<223> OTHER INFORMATION: Synthetic (LHBs-C)

<400> SEQUENCE: 12

```
Met Asp Trp Thr Trp Ile Leu Phe Leu Val Ala Ala Thr Arg Val
1               5                   10                  15

His Ser Gly Gly Trp Ser Ser Lys Pro Arg Gln Gly Met Gly Thr Asn
            20                  25                  30

Leu Ser Val Pro Asn Pro Leu Gly Phe Phe Pro Asp His Gln Leu Asp
        35                  40                  45

Pro Ala Phe Gly Ala Asn Ser Asn Asn Pro Asp Trp Asp Phe Asn Pro
    50                  55                  60

Asn Lys Asp His Trp Pro Glu Ala Asn Gln Val Gly Ala Gly Ala Phe
65                  70                  75                  80

Gly Pro Gly Phe Thr Pro Pro His Gly Gly Leu Leu Gly Trp Ser Pro
                85                  90                  95

Gln Ala Gln Gly Ile Leu Thr Thr Val Pro Ala Ala Pro Pro Pro Ala
            100                 105                 110

Ser Thr Asn Arg Gln Ser Gly Arg Gln Pro Thr Pro Ile Ser Pro Pro
        115                 120                 125

Leu Arg Asp Ser His Pro Gln Ala Arg Gly Arg Lys Arg Arg Ser Met
    130                 135                 140

Gln Trp Asn Ser Thr Thr Phe His Gln Ala Leu Leu Asp Pro Arg Val
145                 150                 155                 160

Arg Gly Leu Tyr Phe Pro Ala Gly Gly Ser Ser Ser Gly Thr Val Asn
                165                 170                 175

Pro Val Pro Thr Thr Ala Ser Pro Ile Ser Ser Ile Phe Ser Arg Thr
            180                 185                 190

Gly Asp Pro Ala Pro Asn Arg Gly Arg Lys Arg Arg Ser Met Glu Ser
        195                 200                 205

Thr Thr Ser Gly Phe Leu Gly Pro Leu Leu Val Leu Gln Ala Gly Phe
    210                 215                 220

Phe Leu Leu Thr Arg Ile Leu Thr Ile Pro Gln Ser Leu Asp Ser Trp
225                 230                 235                 240

Trp Thr Ser Leu Asn Phe Leu Gly Gly Ala Pro Thr Cys Pro Gly Gln
                245                 250                 255
```

-continued

Asn Ser Gln Ser Pro Thr Ser Asn His Ser Pro Thr Ser Cys Pro Pro
            260                 265                 270

Ile Cys Pro Gly Tyr Arg Trp Met Cys Leu Arg Arg Phe Ile Ile Phe
        275                 280                 285

Leu Phe Ile Leu Leu Leu Cys Leu Ile Phe Leu Leu Val Leu Leu Asp
    290                 295                 300

Tyr Gln Gly Met Leu Pro Val Cys Pro Leu Leu Pro Gly Thr Ser Thr
305                 310                 315                 320

Thr Ser Thr Gly Pro Cys Lys Thr Cys Thr Ile Pro Ala Gln Gly Thr
                325                 330                 335

Ser Met Phe Pro Ser Cys Cys Thr Lys Pro Ser Asp Gly Asn Cys
            340                 345                 350

Thr Cys Ile Pro Ile Pro Ser Ser Trp Ala Phe Ala Arg Phe Leu Trp
        355                 360                 365

Glu Trp Ala Ser Val Arg Phe Ser Trp Leu Ser Leu Leu Val Pro Phe
    370                 375                 380

Val Gln Trp Phe Val Gly Leu Ser Pro Thr Val Trp Leu Ser Val Ile
385                 390                 395                 400

Trp Met Met Trp Tyr Trp Gly Pro Ser Leu Tyr Asn Ile Leu Ser Pro
                405                 410                 415

Phe Leu Pro Leu Leu Pro Ile Phe Phe Cys Leu Trp Val Tyr Ile
            420                 425                 430

<210> SEQ ID NO 13
<211> LENGTH: 753
<212> TYPE: DNA
<213> ORGANISM: Artificial Sequence
<220> FEATURE:
<223> OTHER INFORMATION: Synthetic (SHBs-A)

<400> SEQUENCE: 13

```
ggatccgcca ccatggactg gacctggatt ctgttcctgg tggctgccgc tacacgggtg      60
cattctgaaa atatcacatc tggattcctg ggacctctgc tggtgctgca ggctgggttc     120
tttctgctga caagaatcct gactattccc cagtcactgg acagctggtg acatctctg     180
aacttcctgg gcgggagtcc tgtctgtctg gacagaact ctcagagtcc tacttccaat     240
cactctccaa ccagttgtcc ccctatctgc caggctacc gctggatgtg cctgcgaga      300
ttcatcattt tcctgtttat cctgctgctg tgcctgattt ttctgctggt gctgctggac     360
tatcagggca tgctgcctgt ctgcccactg attcccggca gcaccacaac ttctaccggc     420
ccctgtaaga catgcaccac acctgcccag gggaacagta tgtttccatc atgctgttgc     480
actaaaccca ccgatggaaa ttgtacatgc atcccaattc ccagctcctg gccttcgct      540
aagtacctgt gggagtgggc aagcgtgcga ttttcatggc tgagcctgct ggtgcctttc     600
gtccagtggt ttgtgggcct gagcccaact gtctggctgt ccgccatctg gatgatgtgg     660
tactggggc ccagcctgta ttccatcgtg tcaccattca ttccccctgct gccaatcttt     720
ttctgcctgt gggtctacat ctgataactc gag                                  753
```

<210> SEQ ID NO 14
<211> LENGTH: 243
<212> TYPE: PRT
<213> ORGANISM: Artificial Sequence
<220> FEATURE:
<223> OTHER INFORMATION: Synthetic (SHBs-A)

<400> SEQUENCE: 14

```
Met Asp Trp Thr Trp Ile Leu Phe Leu Val Ala Ala Thr Arg Val
1               5                   10                  15

His Ser Glu Asn Ile Thr Ser Gly Phe Leu Gly Pro Leu Val Leu
            20                  25                  30

Gln Ala Gly Phe Phe Leu Leu Thr Arg Ile Leu Thr Ile Pro Gln Ser
        35                  40                  45

Leu Asp Ser Trp Trp Thr Ser Leu Asn Phe Leu Gly Gly Ser Pro Val
    50                  55                  60

Cys Leu Gly Gln Asn Ser Gln Ser Pro Thr Ser Asn His Ser Pro Thr
65                  70                  75                  80

Ser Cys Pro Pro Ile Cys Pro Gly Tyr Arg Trp Met Cys Leu Arg Arg
                85                  90                  95

Phe Ile Ile Phe Leu Phe Ile Leu Leu Leu Cys Leu Ile Phe Leu Leu
                100                 105                 110

Val Leu Leu Asp Tyr Gln Gly Met Leu Pro Val Cys Pro Leu Ile Pro
        115                 120                 125

Gly Ser Thr Thr Thr Ser Thr Gly Pro Cys Lys Thr Cys Thr Thr Pro
    130                 135                 140

Ala Gln Gly Asn Ser Met Phe Pro Ser Cys Cys Cys Thr Lys Pro Thr
145                 150                 155                 160

Asp Gly Asn Cys Thr Cys Ile Pro Ile Pro Ser Ser Trp Ala Phe Ala
                165                 170                 175

Lys Tyr Leu Trp Glu Trp Ala Ser Val Arg Phe Ser Trp Leu Ser Leu
            180                 185                 190

Leu Val Pro Phe Val Gln Trp Phe Val Gly Leu Ser Pro Thr Val Trp
        195                 200                 205

Leu Ser Ala Ile Trp Met Met Trp Tyr Trp Gly Pro Ser Leu Tyr Ser
    210                 215                 220

Ile Val Ser Pro Phe Ile Pro Leu Leu Pro Ile Phe Phe Cys Leu Trp
225                 230                 235                 240

Val Tyr Ile

<210> SEQ ID NO 15
<211> LENGTH: 755
<212> TYPE: DNA
<213> ORGANISM: Artificial Sequence
<220> FEATURE:
<223> OTHER INFORMATION: Synthetic (SHBs-C)

<400> SEQUENCE: 15
gaattcgcca ccatggattg acatggatt ctgttcctgg tcgccgccgc aacacgagtg      60
cattctgaaa gtacaacctc tggcttcctg ggccccctgc tggtgctgca ggcagggttc    120
tttctgctga cacgaatcct gactattcca cagtcactgg acagctggtg gaccagcctg    180
aacttcctgg gcgggccccc tacatgtcca ggacagaact ctcagagtcc cacttccaat    240
cactctccta ccagttgtcc ccctatctgc cccggctaca gatggatgtg cctgcgcaga    300
ttcatcattt tcctgtttat cctgctgctg tgcctgattt ttctgctggt gctgctggac    360
tatcagggaa tgctgcccgt ctgccctctg ctgccaggaa cctcaaccac aagcacaggc    420
ccttgtaaga cttgcaccat tcccgctcag gggactagta tgttcccttc atgctgttgc    480
acaaaaccat ctgatggaaa ttgtacttgc atcccaattc ccagctcctg ggccttcgct    540
aggtttctgt gggagtgggc cagtgtgcgc ttttcctggc tgtctctgct ggtgcccttc    600
gtccagtggt ttgtcggcct gagccctaca gtgtggctgt ccgtcatctg gatgatgtgg    660
``` tactggggc ctagcctgta taatatcctg tcaccatttc tgccactgct gccaatcttc    720
ttttgcctgt gggtctacat ctgataagcg ccgc    755

<210> SEQ ID NO 16
<211> LENGTH: 243
<212> TYPE: PRT
<213> ORGANISM: Artificial Sequence
<220> FEATURE:
<223> OTHER INFORMATION: Synthetic (SHBs-C)

<400> SEQUENCE: 16

Met Asp Trp Thr Trp Ile Leu Phe Leu Val Ala Ala Thr Arg Val
1               5                   10                  15

His Ser Glu Ser Thr Thr Ser Gly Phe Leu Gly Pro Leu Leu Val Leu
                20                  25                  30

Gln Ala Gly Phe Phe Leu Leu Thr Arg Ile Leu Thr Ile Pro Gln Ser
            35                  40                  45

Leu Asp Ser Trp Trp Thr Ser Leu Asn Phe Leu Gly Gly Ala Pro Thr
    50                  55                  60

Cys Pro Gly Gln Asn Ser Gln Ser Pro Thr Ser Asn His Ser Pro Thr
65                  70                  75                  80

Ser Cys Pro Pro Ile Cys Pro Gly Tyr Arg Trp Met Cys Leu Arg Arg
                85                  90                  95

Phe Ile Ile Phe Leu Phe Ile Leu Leu Leu Cys Leu Ile Phe Leu Leu
                100                 105                 110

Val Leu Leu Asp Tyr Gln Gly Met Leu Pro Val Cys Pro Leu Leu Pro
            115                 120                 125

Gly Thr Ser Thr Thr Ser Thr Gly Pro Cys Lys Thr Cys Thr Ile Pro
    130                 135                 140

Ala Gln Gly Thr Ser Met Phe Pro Ser Cys Cys Cys Thr Lys Pro Ser
145                 150                 155                 160

Asp Gly Asn Cys Thr Cys Ile Pro Ile Pro Ser Ser Trp Ala Phe Ala
                165                 170                 175

Arg Phe Leu Trp Glu Trp Ala Ser Val Arg Phe Ser Trp Leu Ser Leu
                180                 185                 190

Leu Val Pro Phe Val Gln Trp Phe Val Gly Leu Ser Pro Thr Val Trp
            195                 200                 205

Leu Ser Val Ile Trp Met Met Trp Tyr Trp Gly Pro Ser Leu Tyr Asn
    210                 215                 220

Ile Leu Ser Pro Phe Leu Pro Leu Leu Pro Ile Phe Phe Cys Leu Trp
225                 230                 235                 240

Val Tyr Ile

<210> SEQ ID NO 17
<211> LENGTH: 3585
<212> TYPE: DNA
<213> ORGANISM: Artificial Sequence
<220> FEATURE:
<223> OTHER INFORMATION: Synthetic (pGX1801 HepB - MCore)

<400> SEQUENCE: 17
gactcttcgc gatgtacggg ccagatatac gcgttgacat tgattattga ctagttatta    60
atagtaatca attacggggt cattagttca tagcccatat atggagttcc gcgttacata    120
acttacggta aatggcccgc ctggctgacc gcccaacgac cccgcccat tgacgtcaat    180 aatgacgtat gttcccatag taacgccaat agggactttc cattgacgtc aatgggtgga    240

```
ctatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg cccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccac catggactgg acctggattc tgttcctggt ggccgctgcc    780
acaagggtgc acagcgacat cgacccctac aaagaattcg cgccaccgt ggaactgctg    840 agcttcctgc ccagcgactt cttcccctcc gtgcgggacc tgctggatac cgccagcgcc    900
ctgtacagag aggccctgga aagccccgag cactgcagcc ctcaccacac agccctgcgg    960
caggccatcc tgtgctgggg cgagctgatg accctggcca cctgggtcgg aagcaacctg   1020
gaagatcccg ccagccggga cctggtggtg tcctacgtga acaccaacat gggcctgaag   1080
atccggcagc tgctgtggtt ccacatctcc tgcctgacct cggccggga accgtgctg    1140 gaatacctgt tgtccttcgg cgtgtggatc agaacccccc ctgcctacag acccccccaac   1200 gcccctatcc tgagcaccct gcccgagaca accgtggtcc gcagacgggg cagaagcccc   1260
agaagaagaa cccccagccc tagacggcgg agatctcaga gccccaggcg agaagatcc    1320 cagagccgcg agagccagtg ctaccctac gacgtgcccg actacgcctg actcgagtct   1380
agagggcccg tttaaacccg ctgatcagcc tcgactgtgc cttctagttg ccagccatct   1440
gttgtttgcc cctcccccgt gccttccttg accctggaag gtgccactcc cactgtcctt   1500
tcctaataaa atgaggaaat tgcatcgcat tgtctgagta ggtgtcattc tattctgggg   1560 ggtgggggtgg ggcaggacag caaggggggag gattgggaag acaatagcag gcatgctggg   1620
gatgcggtgg gctctatggc ttctactggg cggttttatg acagcaagc gaaccggaat   1680 tgccagctgg ggcgccctct ggtaaggttg ggaagccctg caaagtaaac tggatggctt   1740
tctcgccgcc aaggatctga tggcgcaggg gatcaagctc tgatcaagag acaggatgag   1800
gatcgtttcg catgattgaa caagatggat tgcacgcagg ttctccggcc gcttgggtgg   1860
agaggctatt cggctatgac tgggcacaac agacaatcgg ctgctctgat gccgccgtgt   1920
tccggctgtc agcgcagggg cgcccggttc ttttttgtcaa gaccgacctg tccggtgccc   1980
tgaatgaact gcaagacgag gcagcgcggc tatcgtggct ggccacgacg gcgttccctt   2040
gcgcagctgt gctcgacgtt gtcactgaag cgggaaggga ctggctgcta ttgggcgaag   2100
tgccggggca ggatctcctg tcatctcacc ttgctcctgc cgagaaagta ccatcatgg   2160 ctgatgcaat gcggcggctg catacgcttg atccggctac ctgcccattc gaccaccaag   2220
cgaaacatcg catcgagcga gcacgtactc ggatggaagc cggtcttgtc gatcaggatg   2280
atctggacga agagcatcag gggctcgcgc cagccgaact gttcgccagg ctcaaggcga   2340
gcatgcccga cggcgaggat ctcgtcgtga cccatggcga tgcctgcttg ccgaatatca   2400
tggtggaaaa tggccgcttt tctggattca tcgactgtgg ccggctgggt gtggcggacc   2460
gctatcagga catagcgttg gctacccgtg atattgctga agagcttggc ggcgaatggg   2520
ctgaccgctt cctcgtgctt tacggtatcg ccgctcccga ttcgcagcgc atcgccttct   2580
```

```
atcgccttct tgacgagttc ttctgaatta ttaacgctta caatttcctg atgcggtatt    2640
ttctccttac gcatctgtgc ggtatttcac accgcataca ggtggcactt ttcggggaaa    2700
tgtgcgcgga accccatttt gtttattttt ctaaatacat tcaaatatgt atccgctcat    2760
gagacaataa ccctgataaa tgcttcaata atagcacgtg ctaaaacttc attttttaatt   2820 taaaaggatc taggtgaaga tcctttttga atatctcatg accaaaatcc cttaacgtga    2880
gttttcgttc cactgagcgt cagaccccgt agaaaagatc aaaggatctt cttgagatcc    2940 ttttttttctg cgcgtaatct gctgcttgca acaaaaaaa ccaccgctac cagcggtggt     3000
ttgtttgccg gatcaagagc taccaactct ttttccgaag gtaactggct tcagcagagc    3060
gcagatacca atactgtcc ttctagtgta gccgtagtta ggccaccact tcaagaactc     3120
tgtagcaccg cctacatacc tcgctctgct aatcctgtta ccagtggctg ctgccagtgg    3180
cgataagtcg tgtcttaccg ggttggactc aagacgatag ttaccggata aggcgcagcg    3240
gtcgggctga acgggggggtt cgtgcacaca gcccagcttg gagcgaacga cctacaccga   3300
actgagatac ctacagcgtg agctatgaga aagcgccacg cttcccgaag ggagaaaggc    3360
ggacaggtat ccggtaagcg gcagggtcgg aacaggagag cgcacgaggg agcttccagg    3420
gggaaacgcc tggtatcttt atagtcctgt cgggtttcgc cacctctgac ttgagcgtcg    3480 attttttgtga tgctcgtcag gggggcggag cctatggaaa aacgccagca acgcggcctt   3540
tttacggttc ctgggctttt gctggccttt tgctcacatg ttctt                    3585
```

<210> SEQ ID NO 18
<211> LENGTH: 4254
<212> TYPE: DNA
<213> ORGANISM: Artificial Sequence
<220> FEATURE:
<223> OTHER INFORMATION: Synthetic (pGX1802 HepB pLHBs-A)

<400> SEQUENCE: 18

```
gactcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac ccccgcccat tgacgtcaat    180
aatgacgtat gttcccatag taacgccaat agggactttc cattgacgtc aatgggtgga    240
ctatttacgg taaactgccc acttggcagt acatcaagtg tatcatatgc caagtacgcc    300
ccctattgac gtcaatgacg gtaaatggcc cgcctggcat tatgcccagt acatgacctt    360
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccac catggattgg acttggattc tgttcctggt cgccgctgct    780
acacgggtgc attcagggg ctggtcttca aaacctagaa aaggcatggg caccaacctg     840
agcgtgccca atcctctggg gttctttcca gaccaccagc tggaccccgc tttcggcgca    900
aactccaaca atcctgactg ggacttcaac ccaatcaaag accactggcc agcagctaac    960
caagtgggag tcggagcttt cggaccagga ctgactcccc tcatggcgg gattctgggc     1020 tggtctcccc aggctcaggg catcctgacc acagtgagca ctattccacc ccctgcaagc   1080
```

```
accaacaggc agtccggacg ccagccaacc ccaatctcac caccccctgcg agacagccac   1140 cctcaggcca gaggcaggaa acggagatct atgcagtgga atagtacagc cttccatcag   1200
gctctgcagg accccccggt gcggggactg tactttccag ccggaggcag ctcctctggc   1260
actgtcaacc ctgcaccaaa tatcgcctcc cacatcagtt caatttctgc tcgaactgga   1320
gaccccgtga ccaaccgggg cagaaagagg cgcagtatgg agaatattac ctcagggttc   1380
ctgggacctc tgctggtcct gcaggcaggc ttctttctgc tgacccgcat cctgacaatt   1440
cctcagtcac tggatagctg gtggaccagc ctgaacttcc tgggcggcag ccccgtgtgc   1500
ctgggacaga actctcagag tcctacctcc aatcattctc caacaagttg tcctccaatc   1560
tgcccaggct acagatggat gtgcctgcga cggttcatca ttttcctgtt tatcctgctg   1620
ctgtgcctga ttttctgct ggtgctgctg gactatcagg gcatgctgcc agtctgcccc   1680
ctgattcctg gtccactac cacatctaca ggaccctgta agacttgcac taccccctgcc   1740 caggggaaca gtatgtttcc atcatgctgt tgcacaaaac ccactgatgg aaattgtaca   1800
tgcatcccca ttcctagctc ctgggcattc gccaagtatc tgtgggaatg ggcaagcgtg   1860
aggttttcat ggctgagcct gctggtgccc ttcgtccagt ggtttgtggg actgagccct   1920
accgtctggc tgtccgccat ctggatgatg tggtactggg ggcccagcct gtattcaatc   1980
gtgtctccat tcatccccct gctgccaatc ttcttttgtc tgtgggtcta catttgataa   2040
ctcgagtcta gagggcccgt ttaaacccgc tgatcagcct cgactgtgcc ttctagttgc   2100
cagccatctg ttgtttgccc ctcccccgtg ccttccttga ccctggaagg tgccactccc   2160
actgtccttt cctaataaaa tgaggaaatt gcatcgcatt gtctgagtag gtgtcattct   2220
attctggggg gtggggtggg gcaggacagc aaggggggagg attgggaaga caatagcagg   2280
catgctgggg atgcggtggg ctctatggct tctactgggc ggttttatgg acagcaagcg   2340
aaccggaatt gccagctggg gcgccctctg gtaaggttgg gaagccctgc aaagtaaact   2400
ggatggcttt ctcgccgcca aggatctgat ggcgcagggg atcaagctct gatcaagaga   2460
caggatgagg atcgttttcgc atgattgaac aagatggatt gcacgcaggt tctccggccg   2520
cttgggtgga gaggctattc ggctatgact gggcacaaca gacaatcggc tgctctgatg   2580
ccgccgtgtt ccggctgtca gcgcaggggc gcccggttct ttttgtcaag accgacctgt   2640
ccggtgccct gaatgaactg caagacgagg cagcgcggct atcgtggctg gccacgacgg   2700
gcgttccttg cgcagctgtg ctcgacgttg tcactgaagc gggaagggac tggctgctat   2760
tgggcgaagt gccggggcag gatctcctgt catctcacct tgctcctgcc gagaaagtat   2820
ccatcatggc tgatgcaatg cggcggctgc atacgcttga tccggctacc tgcccattcg   2880
accaccaagc gaaacatcgc atcgagcgag cacgtactcg gatggaagcc ggtcttgtcg   2940
atcaggatga tctggacgaa gagcatcagg ggctcgcgcc agccgaactg ttcgccaggc   3000
tcaaggcgag catgcccgac ggcgaggatc tcgtcgtgac ccatggcgat gcctgcttgc   3060
cgaatatcat ggtggaaaat ggccgctttt ctggattcat cgactgtggc cggctgggtg   3120
tggcggaccg ctatcaggac atagcgttgg ctacccgtga tattgctgaa gagcttggcg   3180
gcgaatgggc tgaccgcttc ctcgtgcttt acggtatcgc cgctcccgat tcgcagcgca   3240
tcgccttcta tcgccttctt gacgagttct tctgaattat taacgcttac aatttcctga   3300
tgcggtattt tctccttacg catctgtgcg gtatttcaca ccgcatacag gtggcacttt   3360
tcggggaaat gtgcgcggaa cccctatttg tttatttttc taaatacatt caaatatgta   3420
```

-continued

| | |
|---|---|
| tccgctcatg agacaataac cctgataaat gcttcaataa tagcacgtgc taaaacttca | 3480 |
| tttttaattt aaaaggatct aggtgaagat cctttttgat aatctcatga ccaaaatccc | 3540 |
| ttaacgtgag ttttcgttcc actgagcgtc agaccccgta gaaaagatca aggatcttc | 3600 |
| ttgagatcct tttttctgc gcgtaatctg ctgcttgcaa acaaaaaaac caccgctacc | 3660 |
| agcggtggtt tgtttgccgg atcaagagct accaactctt tttccgaagg taactggctt | 3720 |
| cagcagagcg cagataccaa atactgtcct tctagtgtag ccgtagttag gccaccactt | 3780 |
| caagaactct gtagcaccgc ctacatacct cgctctgcta atcctgttac cagtggctgc | 3840 |
| tgccagtggc gataagtcgt gtcttaccgg gttggactca agacgatagt taccggataa | 3900 |
| ggcgcagcgg tcgggctgaa cggggggttc gtgcacacag cccagcttgg agcgaacgac | 3960 |
| ctacaccgaa ctgagatacc tacagcgtga gctatgagaa agcgccacgc ttcccgaagg | 4020 |
| gagaaaggcg gacaggtatc cggtaagcgg cagggtcgga acaggagagc gcacgaggga | 4080 |
| gcttccaggg ggaaacgcct ggtatcttta tagtcctgtc gggtttcgcc acctctgact | 4140 |
| tgagcgtcga ttttgtgat gctcgtcagg ggggcggagc ctatgaaaaa cgccagcaa | 4200 |
| cgcggccttt ttacggttcc tgggcttttg ctggccttttt gctcacatgt tctt | 4254 |

<210> SEQ ID NO 19
<211> LENGTH: 4284
<212> TYPE: DNA
<213> ORGANISM: Artificial Sequence
<220> FEATURE:
<223> OTHER INFORMATION: Synthetic (pGX1803 HepB pLHBs-C)

<400> SEQUENCE: 19

| | |
|---|---|
| gactcttcgc gatgtacggg ccagatatac gcgttgacat tgattattga ctagttatta | 60 |
| atagtaatca attacggggt cattagttca tagcccatat atggagttcc gcgttacata | 120 |
| acttacggta aatggcccgc ctggctgacc gcccaacgac ccccgcccat tgacgtcaat | 180 |
| aatgacgtat gttcccatag taacgccaat agggactttc cattgacgtc aatgggtgga | 240 |
| ctatttacgg taaactgccc acttggcagt acatcaagtg tatcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |
| tctccacccc attgacgtca atgggagttt gttttggcac caaaatcaac gggactttcc | 540 |
| aaaatgtcgt aacaactccg ccccattgac gcaaatgggc ggtaggcgtg tacggtggga | 600 |
| ggtctatata agcagagctc tctggctaac tagagaaccc actgcttact ggcttatcga | 660 |
| aattaatacg actcactata gggagaccca agctggctag cgtttaaact taagcttggt | 720 |
| accgagctcg gatccactag tccagtgtgg tggaattcgc caccatggat tggacatgga | 780 |
| ttctgttct ggtcgccgcc gcaacccgcg tgcactcagg gggatggtca tcaaaaccta | 840 |
| gacagggaat gggcactaac ctgagtgtgc ccaatcctct ggggttcttt cccgaccacc | 900 |
| agctggatcc tgccttcggc gctaactcta caatccaga ctgggacttc aaccccaata | 960 |
| aggaccactg gcctgaggca aatcaagtgg agcaggagc cttcggacca ggctttacac | 1020 |
| cccctcatgg cggactgctg ggatggtccc ctcaggctca ggggatcctg accacagtcc | 1080 |
| cagcagctcc accccctgca agtactaaca ggcagtcagg acgccagcca accccattt | 1140 |
| ctccacccct gagggacagt caccctcagg ccagaggcag gaagcggaga agcatgcagt | 1200 |
| ggaacagcac taccttccat caggcactgc tggatccacg cgtgcgagga ctgtacttc | 1260 |

```
cagccggagg cagctcctct ggaaccgtga accctgtccc aacaactgcc tccccaatca    1320
gttcaatttt ctctcggaca ggagacccccg ctcctaatcg gggcagaaaa aggcgctcaa    1380
tggaaagcac cacatccggg tttctgggac cactgctggt gctgcaggca ggcttctttc    1440
tgctgaccag aatcctgaca attccccagt ctctggatat ttggtggacc agcctgaact    1500
tcctgggcgg cgcccctact tgtccaggac agaactctca gagtccaaca tcaaatcata    1560
gccccacttc ctgtcctcca atctgccctg ctaccgctg gatgtgcctg cgacggttca    1620 tcatttttcct gtttatcctg ctgctgtgcc tgattttttct gctggtgctg ctggactatc    1680
agggaatgct gcccgtctgc cctctgctgc cagggacttc tactaccagt accgaccttt    1740
gtaagacatg cactattcca gctcagggga cctccatgtt cccctcttgc tgttgcacca    1800
aacctagcga tggaaattgt acatgcatcc caattcccag ctcctgggct ttcgcacgat    1860
ttctgtggga gtgggccagc gtgcgctttt catggctgag cctgctggtg cccttcgtcc    1920
agtggtttgt cggcctgtca cctaccgtgt ggctgagcgt catctggatg atgtggtact    1980
gggggcccag cctgtataat atcctgtcac cattcctgcc actgctgcca atcttctttt    2040
gtctgtgggt ctacatttga taagcggccg ctcgagtcta gagggcccgt ttaaacccgc    2100
tgatcagcct cgactgtgcc ttctagttgc cagccatctg ttgtttgccc ctcccccgtg    2160
ccttccttga ccctggaagg tgccactccc actgtccttt cctaataaaa tgaggaaatt    2220
gcatcgcatt gtctgagtag gtgtcattct attctggggg gtgggggtggg gcaggacagc    2280 aaggggagg attgggaaga caatagcagg catgctgggg atgcggtggg ctctatggct    2340
tctactgggc ggttttatgg acagcaagcg aaccggaatt gccagctggg gcgccctctg    2400
gtaaggttgg gaagccctgc aaagtaaact ggatggcttt ctcgccgcca aggatctgat    2460
ggcgcagggg atcaagctct gatcaagaga caggatgagg atcgtttcgc atgattgaac    2520
aagatggatt gcacgcaggt tctccggccg cttgggtgga gaggctattc ggctatgact    2580
gggcacaaca gacaatcggc tgctctgatg ccgccgtgtt ccggctgtca gcgcaggggc    2640
gcccggttct ttttgtcaag accgacctgt ccggtgccct gaatgaactg caagacgagg    2700
cagcgcggct atcgtggctg gccacgacgg gcgttccttg cgcagctgtg ctcgacgttg    2760
tcactgaagc gggaagggac tggctgctat tgggcgaagt gccggggcag gatctcctgt    2820
catctcacct tgctcctgcc gagaaagtat ccatcatggc tgatgcaatg cggcggctgc    2880
atacgcttga tccggctacc tgcccattcg accaccaagc gaaacatcgc atcgagcgag    2940
cacgtactcg gatggaagcc ggtcttgtcg atcaggatga tctggacgaa gagcatcagg    3000
ggctcgcgcc agccgaactg ttcgccaggc tcaaggcgag catgcccgac ggcgaggatc    3060
tcgtcgtgac ccatggcgat gcctgcttgc cgaatatcat ggtggaaaat ggccgctttt    3120
ctggattcat cgactgtggc cggctgggtg tggcggaccg ctatcaggac atagcgttgg    3180
ctacccgtga tattgctgaa gagcttggcg gcgaatgggc tgaccgcttc ctcgtgcttt    3240
acggtatcgc cgctcccgat tcgcagcgca tcgccttcta tcgccttctt gacgagttct    3300
tctgaattat taacgcttac aatttcctga tgcggtattt tctccttacg catctgtgcg    3360
gtatttcaca ccgcatacag gtggcacttt tcggggaaat gtgcgcggaa cccctatttg    3420 tttattttttc taaatacatt caaatatgta tccgctcatg agacaataac cctgataaat    3480
gcttcaataa tagcacgtgc taaaacttca tttttaattt aaaaggatct aggtgaagat    3540
cctttttgat aatctcatga ccaaaatccc ttaacgtgag ttttcgttcc actgagcgtc    3600
```

| | |
|---|---|
| agaccccgta gaaaagatca aaggatcttc ttgagatcct ttttttctgc gcgtaatctg | 3660 |
| ctgcttgcaa acaaaaaaac caccgctacc agcggtggtt tgtttgccgg atcaagagct | 3720 |
| accaactctt tttccgaagg taactggctt cagcagagcg cagataccaa atactgtcct | 3780 |
| tctagtgtag ccgtagttag gccaccactt caagaactct gtagcaccgc ctacatacct | 3840 |
| cgctctgcta atcctgttac cagtggctgc tgccagtggc gataagtcgt gtcttaccgg | 3900 |
| gttggactca agacgatagt taccggataa ggcgcagcgg tcgggctgaa cggggggttc | 3960 |
| gtgcacacag cccagcttgg agcgaacgac ctacaccgaa ctgagatacc tacagcgtga | 4020 |
| gctatgagaa agcgccacgc ttcccgaagg gagaaaggcg gacaggtatc cggtaagcgg | 4080 |
| cagggtcgga acaggagagc gcacgaggga gcttccaggg ggaaacgcct ggtatcttta | 4140 |
| tagtcctgtc gggtttcgcc acctctgact tgagcgtcga ttttgtgat gctcgtcagg | 4200 |
| ggggcggagc ctatggaaaa acgccagcaa cgcggccttt ttacggttcc tgggcttttg | 4260 |
| ctggcctttt gctcacatgt tctt | 4284 |

<210> SEQ ID NO 20
<211> LENGTH: 3690
<212> TYPE: DNA
<213> ORGANISM: Artificial Sequence
<220> FEATURE:
<223> OTHER INFORMATION: Synthetic (pGX1804 HepB pSHBs-A)

<400> SEQUENCE: 20

| | |
|---|---|
| gactcttcgc gatgtacggg ccagatatac gcgttgacat tgattattga ctagttatta | 60 |
| atagtaatca attacggggt cattagttca tagcccatat atggagttcc gcgttacata | 120 |
| acttacggta aatggcccgc ctggctgacc gcccaacgac ccccgcccat tgacgtcaat | 180 |
| aatgacgtat gttcccatag taacgccaat agggactttc cattgacgtc aatgggtgga | 240 |
| ctatttacgg taaactgccc acttggcagt acatcaagtg tatcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |
| tctccacccc attgacgtca atgggagttt gttttggcac caaaatcaac gggactttcc | 540 |
| aaaatgtcgt aacaactccg ccccattgac gcaaatgggc ggtaggcgtg tacggtggga | 600 |
| ggtctatata agcagagctc tctggctaac tagagaaccc actgcttact ggcttatcga | 660 |
| aattaatacg actcactata gggagaccca agctggctag cgtttaaact taagcttggt | 720 |
| accgagctcg gatccgccac catggactgg acctggattc tgttcctggt ggctgccgct | 780 |
| acacgggtgc attctgaaaa tatcacatct ggattcctgg acctctgct ggtgctgcag | 840 |
| gctgggttct ttctgctgac aagaatcctg actattcccc agtcactgga cagctggtgg | 900 |
| acatctctga cttcctgggg cgggagtcct gtctgtctgg acagaactc tcagagtcct | 960 |
| acttccaatc actctccaac cagttgtccc cctatctgcc caggctaccg ctggatgtgc | 1020 |
| ctgcggagat tcatcatttt cctgtttatc ctgctgctgt gcctgatttt tctgctggtg | 1080 |
| ctgctggact atcagggcat gctgcctgtc tgcccactga ttcccggcag caccacaact | 1140 |
| tctaccggcc cctgtaagac atgcaccaca cctgcccagg gaacagtat gtttccatca | 1200 |
| tgctgttgca ctaaacccac cgatggaaat tgtacatgca tcccaattcc cagctcctgg | 1260 |
| gccttcgcta agtacctgtg ggagtgggca agcgtgcgat tttcatggct gagcctgctg | 1320 |
| gtgcctttcg tccagtggtt tgtgggcctg agcccaactg tctggctgtc cgccatctgg | 1380 |

```
atgatgtggt actgggggcc cagcctgtat ccatcgtgt caccattcat tccctgctg      1440
ccaatcttt tctgcctgtg gtctacatc tgataactcg agtctagagg gcccgtttaa      1500
acccgctgat cagcctcgac tgtgccttct agttgccagc catctgttgt ttgcccctcc    1560
cccgtgcctt ccttgaccct ggaaggtgcc actcccactg tcctttccta ataaaatgag   1620
gaaattgcat cgcattgtct gagtaggtgt cattctattc tggggggtgg ggtggggcag   1680
gacagcaagg gggaggattg gaagacaat agcaggcatg ctgggatgc ggtgggctct     1740
atggcttcta ctgggcggtt ttatggacag caagcgaacc ggaattgcca gctggggcgc   1800
cctctggtaa ggttgggaag ccctgcaaag taaactggat ggctttctcg ccgccaagga   1860
tctgatggcg caggggatca agctctgatc aagagacagg atgaggatcg tttcgcatga   1920
ttgaacaaga tggattgcac gcaggttctc cggccgcttg ggtggagagg ctattcggct   1980
atgactgggc acaacagaca atcggctgct ctgatgccgc cgtgttccgg ctgtcagcgc   2040
aggggcgccc ggttcttttt gtcaagaccg acctgtccgg tgccctgaat gaactgcaag   2100
acgaggcagc gcggctatcg tggctggcca cgacgggcgt tccttgcgca gctgtgctcg   2160
acgttgtcac tgaagcggga agggactggc tgctattggg cgaagtgccg gggcaggatc   2220
tcctgtcatc tcaccttgct cctgccgaga agtatccat catggctgat gcaatgcggc   2280
ggctgcatac gcttgatccg gctacctgcc cattcgacca ccaagcgaaa catcgcatcg   2340
agcgagcacg tactcggatg aagccggtc ttgtcgatca ggatgatctg gacgaagagc    2400
atcagggct cgcgccagcc gaactgttcg ccaggctcaa ggcgagcatg cccgacggcg   2460
aggatctcgt cgtgacccat ggcgatgcct gcttgccgaa tatcatggtg gaaaatggcc   2520
gcttttctgg attcatcgac tgtggccggc tgggtgtggc ggaccgctat caggacatag   2580
cgttggctac ccgtgatatt gctgaagagc ttggcggcga atgggctgac cgcttcctcg   2640
tgctttacgg tatcgccgct cccgattcgc agcgcatcgc cttctatcgc cttcttgacg   2700
agttcttctg aattattaac gcttacaatt tcctgatgcg gtattttctc cttacgcatc   2760
tgtgcggtat ttcacaccgc atacaggtgg cacttttcgg ggaaatgtgc gcggaacccc   2820
tatttgttta ttttttctaaa tacattcaaa tatgtatccg ctcatgagac aataaccctg   2880
ataaatgctt caataatagc acgtgctaaa acttcatttt taatttaaaa ggatctaggt   2940
gaagatcctt tttgataatc tcatgaccaa atcccttaa cgtgagtttt cgttccactg    3000
agcgtcagac cccgtagaaa agatcaaagg atcttcttga tcctttttt ttctgcgcgt    3060
aatctgctgc ttgcaaacaa aaaaaccacc gctaccagcg gtggtttgtt tgccggatca   3120
agagctacca actctttttc cgaaggtaac tggcttcagc agagcgcaga taccaaatac   3180
tgtccttcta gtgtagccgt agttaggcca ccacttcaag aactctgtag caccgcctac   3240
atacctcgct ctgctaatcc tgttaccagt ggctgctgcc agtggcgata agtcgtgtct   3300
taccgggttg gactcaagac gatagttacc ggataaggcg cagcggtcgg gctgaacggg   3360
gggttcgtgc acacagccca gcttggagcg aacgacctac accgaactga gatacctaca   3420
gcgtgagcta tgagaaagcg ccacgcttcc cgaagggaga aaggcggaca ggtatccggt   3480
aagcggcagg gtcggaacag gagagcgcac gagggagctt ccaggggaa acgcctggta    3540
```

-continued

| | |
|---|---|
| tctttatagt cctgtcgggt ttcgccacct ctgacttgag cgtcgatttt tgtgatgctc | 3600 |
| gtcagggggg cggagcctat ggaaaaacgc cagcaacgcg gcctttttac ggttcctggg | 3660 |
| cttttgctgg cctttttgctc acatgttctt | 3690 |

<210> SEQ ID NO 21
<211> LENGTH: 3720
<212> TYPE: DNA
<213> ORGANISM: Artificial Sequence
<220> FEATURE:
<223> OTHER INFORMATION: Synthetic (pGX1805 HepB SHBs-C)

<400> SEQUENCE: 21

| | |
|---|---|
| gactcttcgc gatgtacggg ccagatatac gcgttgacat tgattattga ctagttatta | 60 |
| atagtaatca attacggggt cattagttca tagcccatat atggagttcc gcgttacata | 120 |
| acttacggta aatggcccgc ctggctgacc gcccaacgac ccccgcccat tgacgtcaat | 180 |
| aatgacgtat gttcccatag taacgccaat agggactttc cattgacgtc aatgggtgga | 240 |
| ctatttacgg taaactgccc acttggcagt acatcaagtg tatcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |
| tctccacccc attgacgtca atgggagttt gttttggcac caaaatcaac gggactttcc | 540 |
| aaaatgtcgt aacaactccg ccccattgac gcaaatgggc ggtaggcgtg tacggtggga | 600 |
| ggtctatata agcagagctc tctggctaac tagagaaccc actgcttact ggcttatcga | 660 |
| aattaatacg actcactata gggagaccca agctggctag cgtttaaact taagcttggt | 720 |
| accgagctcg gatccactag tccagtgtgg tggaattcgc caccatggat tggacatgga | 780 |
| ttctgttcct ggtcgccgcc gcaacacgag tgcattctga agtacaaacc tctggcttcc | 840 |
| tgggcccccct gctggtgctg caggcagggt ctttctgct gacacgaatc ctgactattc | 900 |
| cacagtcact ggacagctgg tggaccagcc tgaacttcct gggcggggcc cctacatgtc | 960 |
| caggacagaa ctctcagagt cccacttcca atcactctcc taccagttgt ccccctatct | 1020 |
| gccccggcta cagatggatg tgcctgcgga gattcatcat tttcctgttt atcctgctgc | 1080 |
| tgtgcctgat ttttctgctg gtgctgctgg actatcaggg aatgctgccc gtctgccctc | 1140 |
| tgctgccagg aacctcaacc acaagcacag gcccttgtaa gacttgcacc attcccgctc | 1200 |
| agggggactag tatgttccct tcatgctgtt gcacaaaaacc atctgatgga aattgtactt | 1260 |
| gcatcccaat tcccagctcc tgggccttcg ctaggttttct gtgggagtgg gccagtgtgc | 1320 |
| gcttttcctg gctgtctctg ctggtgccct tcgtccagtg gtttgtcggc ctgagcccta | 1380 |
| cagtgtggct gtccgtcatc tggatgatgt ggtactgggg gcctagcctg tataatatcc | 1440 |
| tgtcaccatt tctgccactg ctgccaatct tcttttgcct gtgggtctac atctgataag | 1500 |
| cggccgctcg agtctagagg gcccgtttaa acccgctgat cagcctcgac tgtgccttct | 1560 |
| agttgccagc catctgttgt ttgccccctcc ccgtgcctt ccttgaccct ggaaggtgcc | 1620 |
| actcccactg tcctttccta ataaaatgag gaaattgcat cgcattgtct gagtaggtgt | 1680 |
| cattctattc tggggggtgg ggtggggcag gacagcaagg gggaggattg ggaagacaat | 1740 |
| agcaggcatg ctggggatgc ggtgggctct atgcttcta ctgggcggtt ttatggacag | 1800 |
| caagcgaacc ggaattgcca gctggggcgc cctctggtaa ggttgggaag ccctgcaaag | 1860 |
| taaactggat ggctttctcg ccgccaagga tctgatggcg caggggatca agctctgatc | 1920 |

```
aagagacagg atgaggatcg tttcgcatga ttgaacaaga tggattgcac gcaggttctc    1980
cggccgcttg ggtggagagg ctattcggct atgactgggc acaacagaca atcggctgct    2040
ctgatgccgc cgtgttccgg ctgtcagcgc aggggcgccc ggttctttt gtcaagaccg     2100
acctgtccgg tgccctgaat gaactgcaag acgaggcagc gcggctatcg tggctggcca    2160
cgacgggcgt tccttgcgca gctgtgctcg acgttgtcac tgaagcggga agggactggc    2220
tgctattggg cgaagtgccg gggcaggatc tcctgtcatc tcaccttgct cctgccgaga    2280
aagtatccat catggctgat gcaatgcggc ggctgcatac gcttgatccg gctacctgcc    2340
cattcgacca ccaagcgaaa catcgcatcg agcgagcacg tactcggatg gaagccggtc    2400
ttgtcgatca ggatgatctg gacgaagagc atcaggggct cgcgccagcc gaactgttcg    2460
ccaggctcaa ggcgagcatg cccgacgcg aggatctcgt cgtgacccat ggcgatgcct     2520
gcttgccgaa tatcatggtg gaaaatggcc gcttttctgg attcatcgac tgtggccggc    2580
tgggtgtggc ggaccgctat caggacatag cgttggctac ccgtgatatt gctgaagagc    2640
ttggcggcga atgggctgac cgcttcctcg tgctttacgg tatcgccgct cccgattcgc    2700
agcgcatcgc cttctatcgc cttcttgacg agttcttctg aattattaac gcttacaatt    2760
tcctgatgcg gtatttctc cttacgcatc tgtgcggtat ttcacaccgc atacaggtgg     2820
cacttttcgg ggaaatgtgc gcggaacccc tatttgttta tttttctaaa tacattcaaa    2880
tatgtatccg ctcatgagac aataaccctg ataaatgctt caataatagc acgtgctaaa    2940
acttcatttt taatttaaaa ggatctaggt gaagatcctt tttgataatc tcatgaccaa    3000
aatcccttaa cgtgagtttt cgttccactg agcgtcagac cccgtagaaa agatcaaagg    3060
atcttcttga gatcctttt ttctgcgcgt aatctgctgc ttgcaaacaa aaaaaccacc     3120
gctaccagcg gtggtttgtt tgccggatca agagctacca actcttttc cgaaggtaac    3180
tggcttcagc agagcgcaga taccaaatac tgtccttcta gtgtagccgt agttaggcca    3240
ccacttcaag aactctgtag caccgcctac atacctcgct ctgctaatcc tgttaccagt    3300
ggctgctgcc agtggcgata agtcgtgtct taccgggttg gactcaagac gatagttacc    3360
ggataaggcg cagcggtcgg gctgaacggg gggttcgtgc acacagccca gcttggagcg    3420
aacgacctac accgaactga gatacctaca gcgtgagcta tgagaaagcg ccacgcttcc    3480
cgaagggaga aaggcggaca ggtatccggt aagcggcagg gtcggaacag gagagcgcac    3540
gagggagctt ccagggggaa acgcctggta tctttatagt cctgtcgggt ttcgccacct    3600
ctgacttgag cgtcgatttt tgtgatgctc gtcaggggg cggagcctat ggaaaaacgc     3660
cagcaacgcg gccttttac ggttcctggg cttttgctgg ccttttgctc acatgttctt     3720
```